(12) United States Patent
Thompson et al.

(10) Patent No.: US 7,700,599 B2
(45) Date of Patent: Apr. 20, 2010

(54) GPR38 RECEPTOR AGONISTS

(75) Inventors: Mervyn Thompson, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 23 days.

(21) Appl. No.: 11/768,339

(22) Filed: Jun. 26, 2007

(65) Prior Publication Data
US 2008/0027065 A1 Jan. 31, 2008

(30) Foreign Application Priority Data
Jun. 28, 2006 (GB) .................. 0612844.1
Jun. 14, 2007 (GB) .................. 0711525.6

(51) Int. Cl.
*A61K 31/497* (2006.01)
*C07D 401/00* (2006.01)
(52) U.S. Cl. .................. 514/253.12; 544/365
(58) Field of Classification Search ........... 514/253.12; 544/365
See application file for complete search history.

(56) References Cited

U.S. PATENT DOCUMENTS

| | | | |
|---|---|---|---|
| 5,912,235 A | 6/1999 | Hoeltje et al. | 514/28 |
| 6,165,985 A | 12/2000 | Jasserand et al. | 514/28 |
| 7,223,788 B2 * | 5/2007 | Schwink et al. | 514/426 |
| 2003/0203922 A1 | 10/2003 | Patel et al. | |
| 2004/0152732 A1 | 8/2004 | Jasserand et al. | |
| 2005/0065156 A1 | 2/2005 | Li et al. | |

FOREIGN PATENT DOCUMENTS

| | | |
|---|---|---|
| DE | 198 05 822 B4 | 2/2009 |
| EP | EP 0 838 469 B1 | 1/2002 |
| JP | 1994211886 A | 8/1994 |
| JP | 09249620 | 9/1997 |
| WO | WO 94/10185 | 11/1994 |
| WO | WO 01/85694 A2 | 11/2001 |
| WO | WO02092592 A1 | 11/2002 |
| WO | WO2005027637 A1 | 3/2005 |
| WO | WO2005115986 A1 | 12/2005 |
| WO | WO2007007018 A1 | 1/2007 |
| WO | WO2007012479 A2 | 2/2007 |
| WO | WO 07/144400 | 12/2007 |

OTHER PUBLICATIONS

"Motilin agonists . . . may be able to maintain long-term efficacy for the treatment of Gi hypomotility disorders." (Emphasis added). Li, et al., Discovery of a Potent and Novel Motilin Agonist, J. of Med. Chem., 47 (7), 1704-1708 (2004).*
Chemical Abstracts Service, Caplus, XP002452868, 2005:612264. Li, et al. "Discovery of a Potent and Novel Motilin Agonist". J. Med. Chem., 47(7): 1704-1708 (2004).
Susan M. Westaway, et al. J. Med. Chem., 52 (4): 1180-1189 (2009).
McCallum, et al. Aliment Pharmacol. Ther., 26: 1121-1130 (2007).
A study to evaluate safety, side effects, muscle activity and speed of gastric emptying of GSK962040. http://clinicaltrials.gov/ct2/show/nct00562848 ClinicalTrials.gov (2007).

* cited by examiner

*Primary Examiner*—James O Wilson
*Assistant Examiner*—Erich A Leeser
(74) *Attorney, Agent, or Firm*—Kathryn L. Sieburth; Lorraine Ling

(57) ABSTRACT

The invention relates to compounds of formula (I)

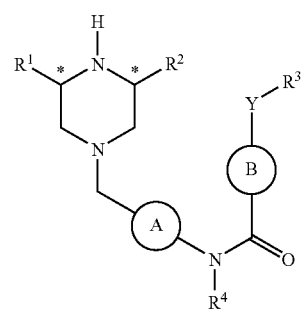

(I)

processes for their preparation, pharmaceutical compositions containing them and their use in the treatment of conditions or disorders which are mediated via the GPR38 receptor.

35 Claims, No Drawings

GPR38 RECEPTOR AGONISTS

This application claims the benefit of GB application No. GB0612844.1 filed 28 Jun. 2006 and GB0711525.6 filed 14 Jun. 2007.

FIELD OF THE INVENTION

The present invention relates to novel benzylpiperazine derivatives having pharmacological activity, processes for their preparation, pharmaceutical compositions containing them and their use in the treatment of various disorders.

BACKGROUND OF THE INVENTION

GPR38 is a 7-transmembrane, G-protein coupled receptor, with high affinity for the peptide motilin [Feighner et al., Science 1999, 284, 2184], suggesting that endogenous motilin exerts all or most of its activity via this receptor.

Motilin is a 22 amino acid peptide found in large amounts within endocrine-like cells of the gastrointestinal tract, and especially in the duodenum-jejunum areas. During fasting, the peptide is known to be associated with the onset of Phase III migrating complex activity within the stomach [Boivin et al., Dig. Dis. Sci. 1992, 37, 1562], suggesting a role in the mechanisms of prokinetic activity. Motilin is also released from the gut during feeding, sham feeding, gastric distension or by oral or intravenous nutrient application [Christofides et al., Gut 1979, 20, 102; Bormans et al., Scand. J. Gastroenterol. 1987, 22, 781], suggesting additional roles for this peptide in the modulation of motility patterns during feeding.

In animals or in man, motilin has long been known to increase gastrointestinal motility, and promote gastric emptying and intestinal propulsion in an anal direction, during both fasting and fed conditions. This activity is thought to be primarily due to a facilitation of at least the cholinergic excitatory function of the gut [Van Assche et al., Eur. J. Pharmacol. 1997, 337, 267], perhaps also involving the activation of the vagus nerve [Mathis & Malbert, Am. J. Physiol. 1998, 274, G80]. In addition, higher concentrations of motilin directly evoke a small contraction of the muscle [Van Assche et al., Eur. J. Pharmacol. 1997, 337, 267].

The antibiotic erythromycin was shown to mimic the gastrointestinal activity of motilin, in addition to its previously-described antibiotic properties [see Peeters, in *Problems of the Gastrointestinal Tract in Anaesthesia* Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., Analyt. Biochem. 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disorders (GERD). Finally, erythromycin has been used to promote intestinal propulsive activity, finding clinical utility in the treatment of pseudo-obstruction and in conditions with impaired colonic motility [Peeters, in *Problems of the Gastrointestinal Tract in Anaesthesia* Ed., Herbert M K et al. Springer-Verlag, Berlin, Heidelberg 1999, pp 39-51].

Consequently it is expected that agonists at the GPR38 receptor will mimic the activity of motilin or of other substances acting at this receptor, such as erythromycin, and find clinical utility in the treatment of gastrointestinal disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs, or in enterally fed patients. Interestingly, the ability of motilin or erythromycin to activate the vagus nerve, the association of this nerve with changes in feeding behaviour [e.g. Furness et al., Auton. Neurosci. 2001, 92, 28] and the chromosomal location of GPR38 [based on Ensembl: 13q21.1 (58.46-59.46 Mb)] within the markers (D13S257-13q14.11 to D13S258 at 13q21.33) of a locus associated with obesity [Feitosa et al, Am. J. Hum. Genet. 2002, 70, 72] also suggests that agonists active at the GPR38 receptor will, in addition to promoting gastrointestinal motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote gastrointestinal motility, the association of motilin gene polymorphism with Crohn's disease [Annese et al., *Dig. Dis. Sci.* 1998, 43, 715-710] and the changes in motilin receptor density during colitis [Depoortere et al., *Neurogastroenterol. Motil.* 2001, 13, 55] suggests a utility for agonists at the motilin receptor for the treatment of inflammatory bowel conditions in general.

Finally, GPR38 is also found in regions outside the gastrointestinal tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the gastrointestinal and feeding utilities already mentioned, but in addition, suggests an involvement of the receptor in a greater spectrum of vagal-hypothalamic functions.

WO9410185, EP838469, WO9823629, DE19805822, and U.S. Pat. No. 6,165,985 claim erythromycin derivatives targeting GPR38 for use in disorders relating to gastrointestinal motility. WO9921846, WO0185694, WO0168620, WO0168621, and WO0168622 disclose a series of small molecule antagonists of the GPR38 receptor. JP07138284 and EP807639 disclose peptide agonists. JP09249620, WO02092592, WO05027637, US2005065156 and Li et al., (2004, Journal of Medicinal Chemistry, 47(7) p 1704-1708) disclose series of small molecule agonists. WO 05012331 and WO 05012332 disclose macrocyclic compounds which are agonists or antagonists of mammalian motilin or ghrelin receptors. WO 06127252 discloses erythromycin derivatives.

WO07/007,018 describes compounds of formula (A), which have activity as agonists of the GPR38 receptor

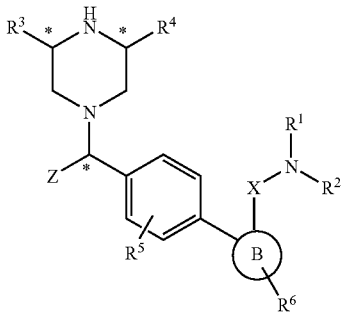

(A)

WO07/012,479 describes compounds of formula (B), which have activity as agonists of the GPR38 receptor

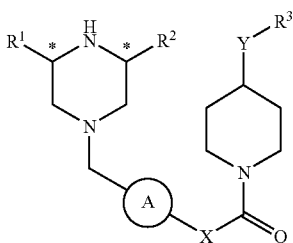

(B)

A structurally novel class of compounds has now been found which provides agonists of the GPR38 receptor.

DETAILED DESCRIPTION OF THE INVENTION

The present invention therefore provides compounds of formula (I) and salts thereof (hereinafter known as "compounds of the invention"):

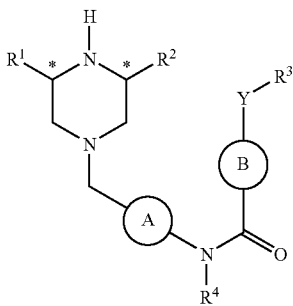

(I)

wherein
A is phenyl or a 6-membered heteroaryl ring, optionally substituted with one susbsituent selected from halogen, $C_{(1-4)}$ alkyl and $C_{(1-4)}$alkoxy;
$R^1$ and $R^2$ are independently H or $C_{(1-4)}$alkyl;
$R^3$ is an optionally substituted phenyl, heteroaryl ring, or heterocyclic ring;
B is an optionally substituted phenyl, 6-membered heteroaryl ring or 6-membered heterocyclic ring connected to the amide carbon via a carbon atom;
Y is a bond, NH, N—$C_{(1-4)}$alkyl, O, C=O, or $CH_2$;
$R^4$ is hydrogen, $C_{(1-4)}$ alkyl or $C_{(1-4)}$alkoxyalkyl.

The present invention also provides compounds of formula (IA) or a pharmaceutically acceptable salt or solvate thereof:

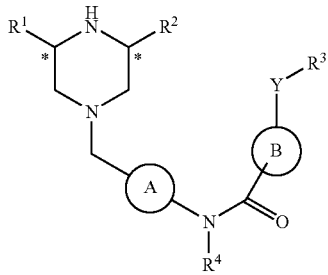

(I)

wherein
A is phenyl or a 6-membered heteroaryl ring, optionally substituted with halogen, $C_{(1-4)}$alkyl or $C_{(1-4)}$alkoxy;
$R^1$ and $R^2$ are independently H or $C_{(1-4)}$ alkyl;
$R^3$ is an optionally substituted phenyl, heteroaryl ring, or heterocyclic ring;
B is an optionally substituted phenyl, a 6-membered heteroaryl ring or a 6-membered heterocyclic ring connected to the amide carbon via a carbon atom;
Y is a bond, NH, N—$C_{(1-4)}$alkyl, O, C=O, or $CH_2$;
$R^4$ is hydrogen or $C_{(1-4)}$ alkyl.

When $R^3$ or B is substituted, it may have 1, 2 or 3 substituents, each independently selected from halogen, $C_{(1-4)}$alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^5$, $NR^5R^6$, $NHCOR^5$, $NHSO_2R^5$, $C(O)CF_3$, $C(O)C_{(1-4)}$alkyl, $C(O)C_{(3-7)}$cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^5$, $CONR^5R^6$, $SOR^6$, $SO_2CF_3$, $SO_2R^6$, $OSO_2R^6$, $OSO_2CF_3$, $SO_2NH_2$, $SO_2NHR^5$, $SO_2NR^5R^6$, where $R^5$ and $R^6$ may be the same or different and represent $C_{(1-4)}$ alkyl, phenyl optionally substituted with halogen or 5 or 6 membered heteroaryl optionally substituted with halogen.

In one embodiment $R^3$ is substituted by fluorine, chlorine, cyano, $CONH_2$, methyl, methoxy or trifluoromethoxy.

In one embodiment B is substituted by methyl.

The term "alkyl" as a group or part of a group e.g. alkoxy or hydroxyalkyl refers to a straight or branched alkyl group in all isomeric forms. The term "$C_{(1-4)}$ alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, or tert-butyl, Examples of such alkoxy groups include methoxy, ethoxy, propoxy, iso-propoxy, butoxy, iso-butoxy, sec-butoxy and tert-butoxy.

Suitable $C_{(3-7)}$cycloalkyl groups include cyclopropyl, cyclobutyl, cyclopentyl and cyclohexyl, cycloheptyl.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl ring" represents a 5 or 6 membered unsaturated aromatic ring which comprises one or more heteroatoms. When the term heteroaryl represents a 5 membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

The term "heterocyclic ring" represents a saturated or partially saturated 5 or 6 membered ring which comprises one or more heteroatoms selected from nitrogen, oxygen and sulphur. Examples of such heterocyclyl groups include pyrrolidinyl, piperidinyl, piperazinyl and morpholinyl.

In one embodiment of the invention A is optionally substituted phenyl or pyridyl.

In one embodiment of the invention $R^1$ is hydrogen or methyl.

In one embodiment of the invention $R^2$ is hydrogen or methyl.

In one embodiment of the invention $R^3$ is optionally substituted phenyl, morpholinyl, piperidinyl, oxadiazolyl, pyridyl, pyrimidinyl, imidazolyl, pyrrolyl. In a further embodiment $R^3$ is optionally substituted phenyl, morpholinyl or piperidinyl.

In one embodiment of the invention B is optionally substituted phenyl, piperidinyl, pyrimidinyl or pyridyl.

In one embodiment of the invention Y is NH, O, $CH_2$, C=O or a bond.

In one embodiment of the invention $R^4$ is hydrogen, methyl, ethyl, methoxyethyl or isopropyl. In a further embodiment $R^4$ is methyl.

In one embodiment of the invention,
A is optionally substituted phenyl or pyridyl; and/or
$R^1$ is hydrogen or methyl; and/or
$R^2$ is hydrogen or methyl; and/or
$R^3$ is optionally substituted phenyl, morpholinyl or piperidinyl; and/or
B is optionally substituted phenyl, piperidinyl, pyrimidinyl or pyridyl; and/or
Y is NH, O, $CH_2$, C=O or a bond; and/or
$R^4$ is methyl; and salts thereof.

In another embodiment of the invention,
A is optionally substituted phenyl or pyridyl; and/or
$R^1$ is hydrogen or methyl; and/or
$R^2$ is hydrogen or methyl; and/or
$R^3$ is optionally substituted phenyl, morpholinyl, piperidinyl, oxadiazolyl, pyridyl, pyrimidinyl, imidazolyl, pyrrolyl; and/or
B is optionally substituted phenyl, piperidinyl, pyrimidinyl or pyridyl; and/or
Y is NH, O, $CH_2$, C=O or a bond; and/or
$R^4$ is hydrogen, methyl, ethyl, methoxyethyl or isopropyl; and salts thereof.

It is to be understood that the present invention covers all combinations of the substituent groups described hereinabove.

In a further embodiment of the invention the (piperazinyl)methylene group and [—N($R^4$)—C(=O)—B—Y—$R^3$] group are para- to each other across ring A and, where B represents optionally substituted phenyl or pyridyl, the [(piperazinyl)methylene-A-N($R^4$)—C(=O)—] group and [—Y—$R^3$] group are either para- or meta- to each other across ring B.

In certain of the compounds of formula (I), dependent upon the nature of the substituent there are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses. Preferred compounds of formula (I) wherein $R^1$ and $R^2$ are both methyl are those wherein the piperazine C* carbons have the 3R,5S-configuration. Preferred compounds of formula (I) wherein one of $R^1$ and $R^2$ is methyl and the other is hydrogen are those wherein the piperazine C* carbon has the S-configuration Certain of the compounds herein can exist in various tautomeric forms and it is to be understood that the invention encompasses all such tautomeric forms.

Suitable compounds of the invention are:
6-(3-fluorophenyl)-N-methyl-N-(4-{[(3S)-3-methyl-1-piperazinyl]methyl}phenyl)-3-pyridinecarboxamide (E1)
6-[(4-fluorophenyl)oxy]-N-methyl-N-(4-{[(3S)-3-methyl-1-piperazinyl]methyl}phenyl)-3-pyridinecarboxamide (E2)
1-(4-fluorophenyl)-N-methyl-N-(4-{[(3S)-3-methyl-1-piperazinyl]methyl}phenyl)-4-piperidinecarboxamide (E3)
6-(4-fluorophenyl)-N,2-dimethyl-N-(4-{[(3S)-3-methyl-1-piperazinyl]methyl}phenyl)-3-pyridinecarboxamide (E4)
6-(4-fluorophenyl)-N-methyl-N-(4-{[(3S)-3-methyl-1-piperazinyl]methyl}phenyl)-3-pyridinecarboxamide (E5)
N-methyl-N-(4-{[(3S)-3-methyl-1-piperazinyl]methyl}phenyl)-6-(4-morpholinyl)-3-pyridinecarboxamide (E6)
4'-fluoro-N-methyl-N-(4-{[(3S)-3-methyl-1-piperazinyl]methyl}phenyl)-4-biphenylcarboxamide (E7)
6-(4-fluorophenyl)-2-methyl-N-(4-{[(3S)-3-methyl-1-piperazinyl]methyl}phenyl)-3-pyridinecarboxamide (E8)
1-[(3-fluorophenyl)carbonyl]-N-methyl-N-(4-{[(3S)-3-methyl-1-piperazinyl]methyl}phenyl)-4-piperidinecarboxamide (E9)
1-[(3-fluorophenyl)methyl]-N-methyl-N-(4-{[(3S)-3-methyl-1-piperazinyl]methyl}phenyl)-4-piperidinecarboxamide (E10)
1-(4-chlorophenyl)-N-methyl-N-(4-{[(3S)-3-methyl-1-piperazinyl]methyl}phenyl)-4-piperidinecarboxamide (E11)
N-methyl-N-(4-{[(3S)-3-methyl-1-piperazinyl]methyl}phenyl)-6-(1-piperidinyl)-3-pyridinecarboxamide (E12)
6-(2-fluorophenyl)-N-methyl-N-(4-{[(3S)-3-methyl-1-piperazinyl]methyl}phenyl)-3-pyridinecarboxamide (E13)
6-(2,4-difluorophenyl)-N,2-dimethyl-N-(4-{[(3S)-3-methyl-1-piperazinyl]methyl}phenyl)-3-pyridinecarboxamide (E14)
6-(3,4-difluorophenyl)-N,2-dimethyl-N-(4-{[(3S)-3-methyl-1-piperazinyl]methyl}phenyl)-3-pyridinecarboxamide (E15)
6-(3-fluorophenyl)-N,2-dimethyl-N-(4-{[(3S)-3-methyl-1-piperazinyl]methyl}phenyl)-3-pyridinecarboxamide (E16)
4-[(3-fluorophenyl)oxy]-N-methyl-N-(4-{[(3S)-3-methyl-1-piperazinyl]methyl}phenyl)benzamide (E17)
6-(3-cyanophenyl)-N,2-dimethyl-N-(4-{[(3S)-3-methyl-1-piperazinyl]methyl}phenyl)-3-pyridinecarboxamide (E18)
6-(4-cyanophenyl)-N,2-dimethyl-N-(4-{[(3S)-3-methyl-1-piperazinyl]methyl}phenyl)-3-pyridinecarboxamide (E19)
4-[(4-fluorophenyl)oxy]-N-methyl-N-(4-{[(3S)-3-methyl-1-piperazinyl]methyl}phenyl)benzamide (E20)
N-(4-{[(3R,5S)-3,5-dimethyl-1-piperazinyl]methyl}phenyl)-6-(4-fluorophenyl)-N,2-dimethyl-3-pyridinecarboxamide (E21)
2-[(4-fluorophenyl)oxy]-N-methyl-N-(4-{[(3S)-3-methyl-1-piperazinyl]methyl}phenyl)benzamide (E22)
N-(4-{[(3R,5S)-3,5-dimethyl-1-piperazinyl]methyl}phenyl)-6-(4-fluorophenyl)-N-methyl-3-pyridinecarboxamide (E23)

4-[(2-fluorophenyl)oxy]-N-methyl-N-(4-{[(3S)-3-methyl-1-piperazinyl]methyl}phenyl)benzamide (E24)

3-[(4-fluorophenyl)oxy]-N-methyl-N-(4-{[(3S)-3-methyl-1-piperazinyl]methyl}phenyl)benzamide (E25)

3-[(3-fluorophenyl)oxy]-N-methyl-N-(4-{[(3S)-3-methyl-1-piperazinyl]methyl}phenyl)benzamide (E26)

6-[(4-fluorophenyl)amino]-N-methyl-N-(4-{[(3S)-3-methyl-1-piperazinyl]methyl}phenyl)-3-pyridinecarboxamide (E27)

2-(4-fluorophenyl)-N,4-dimethyl-N-(4-{[(3S)-3-methyl-1-piperazinyl]methyl}phenyl)-5-pyrimidinecarboxamide (E28)

2-(4-fluorophenyl)-N-methyl-N-(4-{[(3S)-3-methyl-1-piperazinyl]methyl}phenyl)-5-pyrimidinecarboxamide (E29)

6-(4-fluorophenyl)-N,2-dimethyl-N-(4-{[(3R)-3-methyl-1-piperazinyl]methyl}phenyl)-3-pyridinecarboxamide (E30)

6-(4-fluorophenyl)-N-methyl-N-(4-{[(3R)-3-methyl-1-piperazinyl]methyl}phenyl)-3-pyridinecarboxamide (E31)

4'-fluoro-N-methyl-N-(4-{[(3S)-3-methyl-1-piperazinyl]methyl}phenyl)-3-biphenylcarboxamide (E32)

4'-fluoro-N-methyl-N-(4-{[(3S)-3-methyl-1-piperazinyl]methyl}phenyl)-2-biphenylcarboxamide (E33)

6-(3-fluorophenyl)-N-methyl-N-[4-(1-piperazinylmethyl)phenyl]-3-pyridinecarboxamide (E34)

6-[(3-fluorophenyl)oxy]-N-methyl-N-(4-{[(3S)-3-methyl-1-piperazinyl]methyl}phenyl)-3-pyridinecarboxamide (E35)

6-[(2-fluorophenyl)oxy]-N-methyl-N-(4-{[(3S)-3-methyl-1-piperazinyl]methyl}phenyl)-3-pyridinecarboxamide (E36)

6-(3-fluorophenyl)-N,2-dimethyl-N-[4-(1-piperazinylmethyl)phenyl]-3-pyridinecarboxamide (E37)

6-(2-cyanophenyl)-N,2-dimethyl-N-(4-{[(3S)-3-methyl-1-piperazinyl]methyl}phenyl)-3-pyridinecarboxamide (E38)

6-[2-(aminocarbonyl)phenyl]-N,2-dimethyl-N-(4-{[(3S)-3-methyl-1-piperazinyl]methyl}phenyl)-3-pyridinecarboxamide (E39)

6-(2-cyanophenyl)-N-methyl-N-(4-{[(3S)-3-methyl-1-piperazinyl]methyl}phenyl)-3-pyridinecarboxamide (E40)

6-(3-fluorophenyl)-N-methyl-N-(3-methyl-4-{[(3S)-3-methyl-1-piperazinyl]methyl}phenyl)-3-pyridinecarboxamide (E41)

6-(3-fluorophenyl)-N-methyl-N-(4-{[(3S)-3-methyl-1-piperazinyl]methyl}phenyl)-3-pyridinecarboxamide (E42)

6-[(3-cyanophenyl)oxy]-N-methyl-N-(4-{[(3S)-3-methyl-1-piperazinyl]methyl}phenyl)-3-pyridinecarboxamide (E43)

N-(2-fluoro-4-{[(3S)-3-methyl-1-piperazinyl]methyl}phenyl)-6-(3-fluorophenyl)-N-methyl-3-pyridinecarboxamide (E44)

5-[(4-fluorophenyl)oxy]-N-methyl-N-(4-{[(3S)-3-methyl-1-piperazinyl]methyl}phenyl)-2-pyridinecarboxamide (E45)

5-[(3-fluorophenyl)oxy]-N-methyl-N-(4-{[(3S)-3-methyl-1-piperazinyl]methyl}phenyl)-2-pyridinecarboxamide (E46)

N-(2-fluoro-4-{[(3S)-3-methyl-1-piperazinyl]methyl}phenyl)-6-[(4-fluorophenyl)oxy]-N-methyl-3-pyridinecarboxamide (E47)

5-[(3-cyanophenyl)oxy]-N-methyl-N-(4-{[(3S)-3-methyl-1-piperazinyl]methyl}phenyl)-2-pyridinecarboxamide (E48)

5-[(4-fluorophenyl)amino]-N-methyl-N-(4-{[(3S)-3-methyl-1-piperazinyl]methyl}phenyl)-2-pyridinecarboxamide (E49)

1-[(3,4-difluorophenyl)methyl]-N-methyl-N-(4-{[(3S)-3-methyl-1-piperazinyl]methyl}phenyl)-4-piperidinecarboxamide (E50)

1-[(4-fluorophenyl)methyl]-N-methyl-N-(4-{[(3S)-3-methyl-1-piperazinyl]methyl}phenyl)-4-piperidinecarboxamide (E51)

N-(3-fluoro-4-{[(3S)-3-methyl-1-piperazinyl]methyl}phenyl)-6-(3-fluorophenyl)-N-methyl-3-pyridinecarboxamide (E52)

N-(3-fluoro-4-{[(3S)-3-methyl-1-piperazinyl]methyl}phenyl)-6-[(4-fluorophenyl)oxy]-N-methyl-3-pyridinecarboxamide (E53)

1-[(3-cyanophenyl)methyl]-N-methyl-N-(4-{[(3S)-3-methyl-1-piperazinyl]methyl}phenyl)-4-piperidinecarboxamide (E54)

1-[(4-cyanophenyl)methyl]-N-methyl-N-(4-{[(3S)-3-methyl-1-piperazinyl]methyl}phenyl)-4-piperidinecarboxamide (E55)

6-(3-fluorophenyl)-N-(1-methylethyl)-N-(4-{[(3S)-3-methyl-1-piperazinyl]methyl}phenyl)-3-pyridinecarboxamide (E56)

N-ethyl-6-(3-fluorophenyl)-N-(4-{[(3S)-3-methyl-1-piperazinyl]methyl}phenyl)-3-pyridinecarboxamide (E57)

6-(3-fluorophenyl)-N-[2-(methyloxy)ethyl]-N-(4-{[(3S)-3-methyl-1-piperazinyl]methyl}phenyl)-3-pyridinecarboxamide (E58)

6-[(4-fluorophenyl)oxy]-N-methyl-N-(3-methyl-4-{[(3S)-3-methyl-1-piperazinyl]methyl}phenyl)-3-pyridinecarboxamide (E59)

6-(3-fluorophenyl)-N-methyl-N-(5-{[(3S)-3-methyl-1-piperazinyl]methyl}-2-pyridinyl)-3-pyridinecarboxamide (E60)

6-[(4-fluorophenyl)oxy]-N-methyl-N-(5-{[(3S)-3-methyl-1-piperazinyl]methyl}-2-pyridinyl)-3-pyridinecarboxamide (E61)

6-[(4-fluorophenyl)oxy]-N-methyl-N-(4-{[(3S)-3-methyl-1-piperazinyl]methyl}phenyl)-2-pyridinecarboxamide (E62)

6-(4-fluoro-1-piperidinyl)-N-methyl-N-(4-{[(3S)-3-methyl-1-piperazinyl]methyl}phenyl)-3-pyridinecarboxamide (E63)

6-(3-fluorophenyl)-N-methyl-N-(4-{[(3S)-3-methyl-1-piperazinyl]methyl}phenyl)-2-pyridinecarboxamide (E64)

N-methyl-4-(3-methyl-1,2,4-oxadiazol-5-yl)-N-(4-{[(3S)-3-methyl-1-piperazinyl]methyl}phenyl)benzamide (E65)

N-ethyl-6-[(4-fluorophenyl)oxy]-N-(4-{[(3S)-3-methyl-1-piperazinyl]methyl}phenyl)-3-pyridinecarboxamide (E66)

N-methyl-N-(4-{[(3S)-3-methyl-1-piperazinyl]methyl}phenyl)-6-(3-pyridinyloxy)-3-pyridinecarboxamide (E67)

6-[(3-fluorophenyl)oxy]-N-methyl-N-(4-{[(3S)-3-methyl-1-piperazinyl]methyl}phenyl)-2-pyridinecarboxamide (E68)

6-(4,4-difluoro-1-piperidinyl)-N-methyl-N-(4-{[(3S)-3-methyl-1-piperazinyl]methyl}phenyl)-3-pyridinecarboxamide (E69)

6-[(4-fluorophenyl)oxy]-N-methyl-N-(6-{[(3S)-3-methyl-1-piperazinyl]methyl}-3-pyridinyl)-3-pyridinecarboxamide (E70)

5-(4-fluorophenyl)-N-methyl-N-(4-{[(3S)-3-methyl-1-piperazinyl]methyl}phenyl)-2-pyridinecarboxamide (E71)

5-(3-cyanophenyl)-N-methyl-N-(4-{[(3S)-3-methyl-1-piperazinyl]methyl}phenyl)-2-pyridinecarboxamide (E72)

N-methyl-5-[3-(methyloxy)phenyl]-N-(4-{[(3S)-3-methyl-1-piperazinyl]methyl}phenyl)-2-pyridinecarboxamide (E73)

N-methyl-5-[4-(methyloxy)phenyl]-N-(4-{[(3S)-3-methyl-1-piperazinyl]methyl}phenyl)-2-pyridinecarboxamide (E74)

5-(3-fluorophenyl)-N-methyl-N-(4-{[(3S)-3-methyl-1-piperazinyl]methyl}phenyl)-2-pyridinecarboxamide (E75)

6-(4-fluorophenyl)-N-methyl-N-(6-{[(3S)-3-methyl-1-piperazinyl]methyl}-3-pyridinyl)-3-pyridinecarboxamide (E76)

6-[(4-fluorophenyl)oxy]-N-methyl-N-(4-methyl-5-{[(3S)-3-methyl-1-piperazinyl]methyl}-2-pyridinyl)-3-pyridinecarboxamide (E77)

N,2'-dimethyl-N-(4-{[(3S)-3-methyl-1-piperazinyl]methyl}phenyl)-3,4'-bipyridine-6-carboxamide (E78)

6-[(4-fluorophenyl)oxy]-N-[2-(methyloxy)ethyl]-N-(4-{[(3S)-3-methyl-1-piperazinyl]methyl}phenyl)-3-pyridinecarboxamide (E79)

N-(3-chloro-4-{[(3S)-3-methyl-1-piperazinyl]methyl}phenyl)-6-[(4-fluorophenyl)oxy]-N-methyl-3-pyridinecarboxamide (E80)

N,2'-dimethyl-N-(4-{[(3S)-3-methyl-1-piperazinyl]methyl}phenyl)-2,4'-bipyridine-5-carboxamide (E81)

N-methyl-N-(4-{[(3S)-3-methyl-1-piperazinyl]methyl}phenyl)-4-(2-pyridinyl)benzamide (E82)

N-methyl-N-(4-{[(3S)-3-methyl-1-piperazinyl]methyl}phenyl)-4-(2-pyrimidinyl)benzamide (E83)

N-methyl-N-(4-{[(3S)-3-methyl-1-piperazinyl]methyl}phenyl)-4-(1H-pyrazol-1-yl)benzamide (E84)

N-methyl-N-(4-{[(3S)-3-methyl-1-piperazinyl]methyl}phenyl)-6-(1H-pyrrol-1-yl)-3-pyridinecarboxamide (E85)

N-methyl-N-(4-{[(3S)-3-methyl-1-piperazinyl]methyl}phenyl)-4-{[4-(trifluoromethyl)phenyl]carbonyl}benzamide (E86)

5-(4-cyanophenyl)-N-methyl-N-(4-{[(3S)-3-methyl-1-piperazinyl]methyl}phenyl)-2-pyridinecarboxamide (E87)

6-(4-fluorophenyl)-N-methyl-N-(4-{[(3S)-3-methyl-1-piperazinyl]methyl}phenyl)-2-pyridinecarboxamide (E88)

N-methyl-N-(4-{[(3S)-3-methyl-1-piperazinyl]methyl}phenyl)-4-(6-methyl-3-pyridinyl)benzamide (E89)

N-methyl-N-(4-{[(3S)-3-methyl-1-piperazinyl]methyl}phenyl)-4-(2-pyrazinyl)benzamide (E90)

6-(4-fluorophenyl)-N-methyl-N-(5-{[(3S)-3-methyl-1-piperazinyl]methyl}-2-pyridinyl)-2-pyridinecarboxamide (E91)

6-(3-fluorophenyl)-N-methyl-N-(5-{[(3S)-3-methyl-1-piperazinyl]methyl}-2-pyridinyl)-2-pyridinecarboxamide (E92)

2-[(3-fluorophenyl)oxy]-N-methyl-N-(4-{[(3S)-3-methyl-1-piperazinyl]methyl}phenyl)benzamide (E93)

and salts thereof.

One embodiment of the invention is 6-[(4-fluorophenyl)oxy]-N-methyl-N-(4-{[(3S)-3-methyl-1-piperazinyl]methyl}phenyl)-3-pyridinecarboxamide or a salt thereof.

A further embodiment of the invention is 6-[(4-fluorophenyl)oxy]-N-methyl-N-(4-{[(3S)-3-methyl-1-piperazinyl]methyl}phenyl)-3-pyridinecarboxamide fumarate salt.

One embodiment of the invention is 6-[(4-fluorophenyl)oxy]-N-methyl-N-(4-methyl-5-{[(3S)-3-methyl-1-piperazinyl]methyl}-2-pyridinyl)-3-pyridinecarboxamide or a salt thereof.

Included within the scope of the "compounds of the invention" are all salts, solvates, hydrates, complexes, polymorphs, prodrugs, radiolabelled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

In a further aspect, this invention provides a process for the preparation of a compound of formula (I)

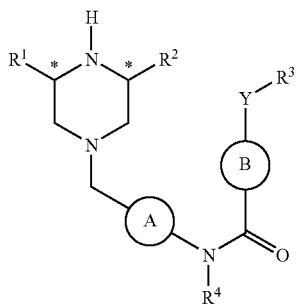
(I)

as defined above or a salt thereof, which process comprises reacting of a compound of formula (II)

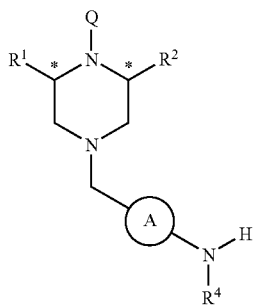
(II)

wherein $R^1$, $R^2$, A and $R^4$ are as defined above and Q is hydrogen or a suitable nitrogen protecting group such as tert-butyloxycarbonyl (Boc) or benzyloxycarbonyl (Cbz), and a compound of formula $R^3$—Y—B—C(=O)-$L^1$ wherein $R^3$, B and Y are as defined above and $L^1$ is a leaving group such as halogen, alkanoyloxy or sulfonyloxy, using conditions suitable for the formation of an amide bond. For example, where $L^1$ represents halogen, the reaction may be carried out using a suitable base such as triethylamine in an inert solvent such as dichloromethane.

And thereafter optionally carrying out one or more of the following reactions:
 a) Converting one compound of formula (I) into another compound of formula (I);
 b) Removing any protecting group;
 c) Forming a suitable pharmaceutically acceptable salt or solvate of the compound so formed.

Alternatively, a compound of formula (I) as defined above or a salt thereof, may be prepared by a process which comprises reacting a compound of formula (II) as defined above with a compound of formula $R^3$—Y—B—C(=O)—OH where $R^3$, B and Y are defined above in the presence of a suitable coupling reagent such as N,N'-dicyclohexylcarbodiimide (DCC), N-benzyl-N'-cyclohexylcarbodiimide resin or 1-(3-dimethylaminopropyl)-3-ethylcarbodiimide (EDC); optionally in the presence of 1-hydroxybenzotriazole (HOBt); in a suitable solvent such as dichloromethane, dimethylformamide or mixtures thereof.

And thereafter optionally carrying out one or more of the following reactions:
 a) Converting one compound of formula (I) into another compound of formula (I);
 b) Removing any protecting group;
 c) Forming a suitable pharmaceutically acceptable salt or solvate of the compound so formed.

Compounds of formula (II) where A represents a 1,4-phenylene group may be prepared by reaction of a compound of formula (III)

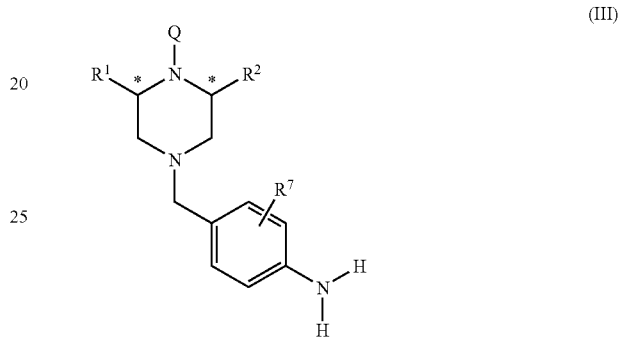
(III)

wherein $R^1$ and $R^2$ are as defined above, $R^7$ represents optional substitution in the phenylene moiety as defined for A above and Q is hydrogen or a suitable nitrogen protecting group such as tert-butyloxycarbonyl (Boc) or benzyloxycarbonyl (Cbz) with an appropriate aldehyde, ketone or enol ether to provide $R^4$, using conditions suitable for a reductive amination; for example in the presence of a suitable reducing agent such as sodium borohydride and in a suitable solvent such as methanol and optionally in the presence of a suitable base such as sodium methoxide.

Compounds of formula (III) may be prepared by reaction of a compound of formula (IV)

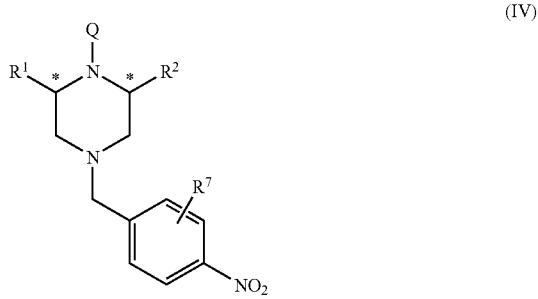
(IV)

wherein $R^1$, $R^2$, $R^7$ and Q are as defined above, using conditions suitable for a reduction; for example when Q is Boc, hydrogenation in the presence of a suitable catalyst such as palladium on charcoal or platinum on charcoal, in a suitable solvent such as methanol and optionally in the presence of a suitable base such as potassium hydroxide or triethylamine. Alternatively when Q is Boc or Cbz, the reduction may be carried out using a suitable metal reducing agent such as iron powder, in the presence of a suitable proton source such as ammonium chloride and in a suitable solvent such as aqueous methanol.

Compounds of formula (IV) may be prepared by reaction of a compound of formula (V)

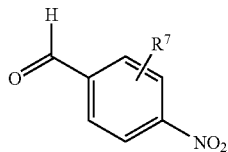

(V)

wherein $R^7$ is as defined above, with a compound of formula (VI),

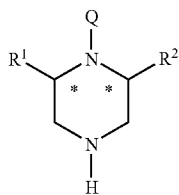

(VI)

wherein $R^1$, $R^2$ and Q are as defined above, using reaction conditions suitable for a reductive amination, for example in the presence of a reducing agent such as sodium tri(acetoxy) borohydride in a suitable solvent such as dichloromethane or 1,2-dichloroethane.

Alternatively compounds of formula (IV) may be prepared by reaction of a compound of formula (VII)

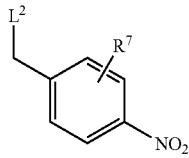

(VII)

wherein $R^7$ is as defined above and $L^2$ represents a leaving group such as halogen, alkylsulfonyloxy or arylsulfonyloxy, with a compound of formula (VI) as defined above, using conditions suitable for an alkylation reaction, for example use of an appropriate solvent such as N,N-dimethylformamide and a suitable base such as Hunig's base.

Compounds of formula (VII) are commercially available or may be prepared by methods similar to those described in the literature (see for example WO 03/053972, WO 03/037898.

Compounds of formula $R^3$—Y—B—C(=O)-$L^1$ as defined above may be prepared from compounds of formula $R^3$—Y—B—C(=O)—OH by reaction with an appropriate reagent for introduction of the leaving group, for example where $L^1$ is chlorine, treatment with thionyl chloride, or oxalyl chloride in the presence of catalytic N,N-dimethylformamide.

An alternative process for preparation of compounds of formula (I) comprises reaction of a compound of formula (VIII)

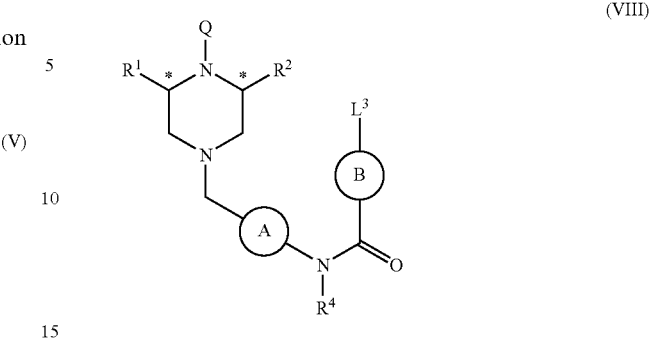

(VIII)

Wherein $R^1$, $R^2$, $R^4$, A, B and Q are as defined above and $L^3$ represents a leaving group such as halogen or trifluoromethylsulfonyloxy, and a compound of formula $M^1$-Y—$R^3$ wherein $R^3$ and Y are as defined above and $M^1$ represents hydrogen, a metal residue (e.g. alkali metal salt, trialkylstannyl) or a boronic acid, optionally in the presence of a suitable base such as potassium carbonate, cesium carbonate, sodium carbonate, sodium hydride or triethylamine and optionally using a suitable transition metal catalyst system such as palladium acetate/BINAP, copper (I) chloride/2,2,6,6-tetramethyl-3,5-heptanedione or tetrakis(triphenylphosphine) palladium (0).

And thereafter optionally carrying out one or more of the following reactions:
a) Converting one compound of formula (I) into another compound of formula (I);
b) Removing any protecting group;
c) Forming a suitable pharmaceutically acceptable salt or solvate of the compound so formed.

Compounds of formula (VIII) may be prepared by reaction of compounds of formula (II) as defined above with a compound of formula $L^3$-B—C(=O)-$L^1$ or $L^3$-B—C(=O)—OH wherein $L^1$, $L^3$ and B are as defined above, using methods similar and/or analogous to those described above.

An alternative process for preparation of compounds of formula (III) comprises reaction of a compound of formula (VI) as defined above with a compound of formula (IX):

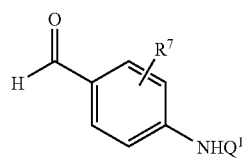

(IX)

wherein $R^7$ is as defined above and $Q^1$ is a suitable protecting group such as acetyl under conditions suitable for reductive amination as described above, followed by a suitable deprotection step to remove $Q^1$.

Compounds of formula (IX) are commercially available or may be prepared from the corresponding carboxylic acid, using general methods for the conversion of a carboxylic acid to an aldehyde. See, for example, M. B. Smith & J. March, Advanced Organic Chemisty, 5th Edition, J Wiley & Sons, 2001, Chapter 19, p. 1506-1604.

An alternative process for preparation of compounds of formula (II) wherein A represents an optionally substituted 1,4-phenylene group, an optionally substituted 2,5-pyridyl group or an optionally substituted 3,6-pyridyl group comprises reaction of a compound of formula (VI) as defined above with a compound of formula (X):

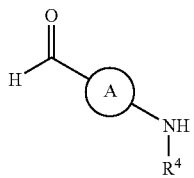

wherein A and $R^4$ are as defined above, under conditions suitable for reductive amination as described above.

Compounds of formula (X) wherein A represents an optionally substituted 1,4-phenylene group or an optionally substituted 2,5-pyridyl group, and $R^4$ is as defined above may be prepared by reaction of a compound of formula (XI):

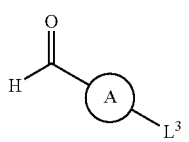

wherein A represents an optionally substituted 1,4-phenylene group or an optionally substituted 2,5-pyridyl group and $L^3$ is as defined above with a compound of formula $R^4NHQ^1$, wherein $R^4$ is as defined above and $Q^1$ is a suitable nitrogen protecting group such as tert-butyloxycarbonyl (Boc), in the presence of a suitable transition metal catalyst system such as tris(dibenzylideneacetone) dipalladium(0)/xantphos, in the presence of a suitable base such as cesium carbonate and in a suitable solvent such as dioxane; followed by a suitable deprotection step.

Compounds of formula (XI) wherein A represents an optionally substituted 1,4-phenylene group or an optionally substituted 2,5-pyridyl group are commercially available or may be prepared by reaction of a compound of formula (XII):

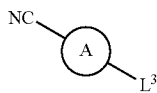

wherein A represents an optionally substituted 1,4-phenylene group or an optionally substituted 2,5-pyridyl group and $L^3$ is as defined above with a suitable reducing agent such as diisobutylaluminium hydride in a suitable solvent such as toluene.

Compounds of formula (X) wherein A represents an optionally substituted 3,6-pyridyl group may be prepared by reaction of a compound of formula (XIII):

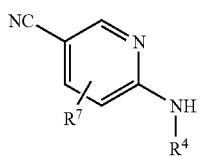

wherein $R^4$ is as defined above and $R^7$ represents optional substitution in the pyridine moiety with a suitable reducing agent such as diisobutylaluminium hydride in a suitable solvent such as toluene.

Compounds of formula (XIII) wherein $R^4$ is as defined above and $R^7$ represents optional substitution of the pyridine moiety with $C_{(1-4)}$alkyl or $C_{(1-4)}$alkoxy may be prepared by reaction of a compound of formula (XIV):

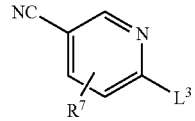

wherein $R^7$ represents optional substitution of the pyridine moiety with $C_{(1-4)}$alkyl or $C_{(1-4)}$alkoxy and $L^3$ is as defined above with a compound of formula $R^4NH_2$ in a suitable solvent such as THF and optionally in the presence of a suitable base.

An alternative process for preparation of compounds of formula (III) wherein A represents an optionally substituted 3,6-pyridyl group comprises reaction of a compound of formula (VI) as defined above with a compound of formula (XV):

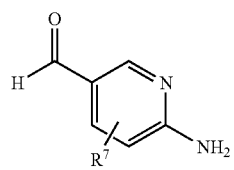

wherein $R^7$ represents optional substitution of the pyridine moiety with $C_{(1-4)}$alkyl or $C_{(1-4)}$alkoxy, under conditions suitable for reductive amination as described above.

Compounds of formula (XV) may be prepared by reaction of a compound of formula (XVI):

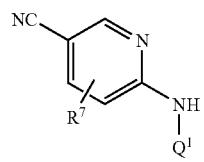

wherein $R^7$ represents optional substitution of the pyridine moiety with $C_{(1-4)}$alkyl or $C_{(1-4)}$alkoxy and $Q^1$ is a suitable protecting group such as trifluoroacetyl, with a suitable reducing agent such as nickel/aluminium alloy in the presence of formic acid and in a suitable solvent such water.

Compounds of formula (XVI) may be prepared by reaction of a compound of formula (XVII):

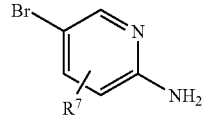

wherein $R^7$ represents optional substitution of the pyridine moiety with $C_{(1-4)}$alkyl or $C_{(1-4)}$alkoxy, with copper (I) cyanide in a suitable solvent such as DMF followed by suitable protection of the amino group. When $Q^1$ is trifluoroacetyl the protection may be carried out using trifluoroacetic anhydride in the presence of a suitable base such as 2,6-lutidine and in a suitable solvent such as dichloromethane.

Compounds of formula (V), (VI), (XII), (XIV) and (XVII) are commercially available, described in the literature or can be prepared by analogous or similar methods.

Compounds of formula $R^3$—Y—B—C(=O)—OH are commercially available, described in the literature or can be prepared by analogous or similar methods (for example, see WO 2003/068749, WO 2004/072069, WO 2005/016928, WO 2003/027061, WO 2005/016915, WO 1997/025309, WO 2005/047278, WO 2002/016356, WO 2007/041634 and WO 2005/073210).

Compounds of formula $L^3$-B—C(=O)-$L^1$ are either commercially available, described in the literature or can be prepared by analogous or similar methods.

It will be appreciated by those skilled in the art that it may be necessary to protect certain reactive substituents during some of the above procedures. Standard protection and deprotection techniques, such as those described in Greene T. W. & Wuts P. G. M., Protective groups in organic synthesis, $2^{nd}$ Edition, New York, Wiley (1991), can be used. For example, primary and secondary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluoroacetic acid in a suitable solvent such as dichloromethane, diethyl ether, 1,4-dioxane, isopropanol or mixtures thereof.

Salts may be prepared conventionally by reaction with the appropriate acid or acid derivative.

The present invention also provides compounds of formula (II) and (VIII) as shown above wherein $R^1$, $R^2$, $R^4$, A and B are as defined for formula (I), Q is hydrogen or a suitable protecting group such as tert-butyloxycarbonyl (BOC) or benzyloxycarbonyl (CBZ) and $L^3$ is a leaving group such as halogen or trifluoromethylsulfonyloxy. These compounds are useful as intermediates in the preparation of compounds of the present invention.

The potencies and efficacies of the compounds of this invention for GPR38 can be determined by FLIPR assay performed on the human cloned receptor as described herein. Compounds of formula (I) have demonstrated partial or full agonist activity at the GPR38 receptor, using the FLIPR (FLuorometric Imaging Plate Reader) functional assays described herein.

Compounds of formula (I) and pharmaceutically acceptable salts thereof are therefore of use in the treatment of conditions or disorders which are mediated via the GPR38 receptor. In particular the compounds of formula (I) and pharmaceutically acceptable salts thereof are of use in the treatment of certain gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, or in enterally fed patients, Crohn's disease, colitis, cachexia associated with advanced diseases such as cancer and/or the treatment thereof, and other disorders such as incontinence (herein after referred to as the "Disorders of the Invention").

It is to be understood that "treatment" as used herein includes prophylaxis as well as alleviation of established symptoms.

Thus the invention also provides compounds of formula (I) and pharmaceutically acceptable salts thereof for use as a therapeutic substance, in particular in the treatment of conditions or disorders mediated via the GPR38 receptor. In particular the invention provides compounds of formula (I) and pharmaceutically acceptable salts thereof for use as a therapeutic substance in the treatment of gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, or in enterally fed patients, Crohn's disease, colitis, cachexia associated with advanced diseases such as cancer and/or the treatment thereof, and other disorders such as incontinence.

The invention further provides a method of treatment of conditions or disorders in mammals including humans which can be mediated via the GPR38 receptor, which comprises administering to the sufferer a therapeutically safe and effective amount of a compounds of formula (I) or a pharmaceutically acceptable salt thereof.

In another aspect, the invention provides for the use of compounds of formula (I) and pharmaceutically acceptable salts thereof in the manufacture of a medicament for use in the treatment of the conditions or disorders mediated via the GPR38 receptor.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg or 1.0 to 200 mg, and such unit doses may be administered more than once a day, for example two or three times a day.

Compounds of formula (I) and pharmaceutically acceptable salts thereof may be used in combination preparations. For example, the compounds of formula (I) and pharmaceutically acceptable salts thereof may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Conditions, Hardware and Software for Analytical LCMS Systems (I)

Hardware
Agilent 1100 Gradient Pump
Agilent 1100 Autosampler
Agilent 1100 DAD Dectector
Agilent 1100 Degasser
Agilent 1100 Oven
Agilent 1100 Controller
Waters ZQ Mass Spectrometer Sedere Sedex 55, Sedere Sedex 85 or Polymer Labs PL-ELS-2100

Software
Waters MassLynx version 4.0 SP2

Column
The column used is a Waters Atlantis, the dimensions of which are 4.6 mm×50 mm. The stationary phase particle size is 3 μm.

Solvents
A: Aqueous solvent=Water+0.05% Formic Acid
B: Organic solvent=Acetonitrile+0.05% Formic Acid Method
The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate
The above method has a flow rate of 3 mL/mins (II)

Hardware
Waters Acquity Binary Solvent Manager
Waters Acquity Sample Manager
Waters Acquity PDA
Waters ZQ Mass Spectrometer
Sedere Sedex 85, Sedere Sedex 75, Polymer Labs PL-ELS-2100

Software
Waters MassLynx version 4.1

Column
The column used is a Waters Acquity BEH UPLC C18, the dimensions of which are 2.1 mm×50 mm. The stationary phase particle size is 1.7 μm.

Solvents
A: Aqueous solvent=Water+0.05% Formic Acid
B: Organic solvent=Acetonitrile+0.05% Formic Acid
Weak Wash=1:1 Methanol:Water
Strong Wash=Water Method
The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40 deg
The UV detection range is from 220 to 330 nm Conditions for Open Access Mass Directed Auto Prep System (MDAP)

Hardware
Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System.

Software
MicroMass MassLynx v4.0

Column
The column used is typically a Supelco LCABZ++column whose dimensions are 20 mm internal diameter by 100 mm in length. The stationary phase particle size is 5 μm.

Solvents
A:. Aqueous solvent=Water+0.1% Formic Acid
B:. Organic solvent=MeCN:Water 95:5+0.05% Formic Acid
Make up solvent=MeOH:Water 80:20+50 mMol Ammonium Acetate
Needle rinse solvent=MeOH: Water:DMSO 80:10:10

Methods
One of five methods may be used depending on the analytical retention time of the compound of interest.
All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B Flow Rate
All of the above methods have a flow rate of 20 mL/min.

(II)

Hardware
Waters 2525 Binary Gradient Module
Waters 515 Makeup Puma
Waters Puma Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector Software
Waters MassLynx version 4 SP2

Column
The columns used are Waters Atlantis, the dimensions of which are 19 mm×100 mm (small scale) and 30 mm×100 mm (large scale). The stationary phase particle size is 5 μm.

Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol Methods There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow rate

All of the above MDAP methods have a flow rate of either 20 mls/min (Small Scale) or 40 mls/min (Large Scale).

Shallow Gradients
Large 1.5 to 2.3 min=13-29% B
Large 1.9 to 2.3 min=25-41% B
Large 2.3 to 2.6 min=37-53% B
Large 2.6 to 3.1 min=49-65% B
Large 3.1 to 3.6 min=61-77% B Conditions Used for NMR Hardware
Bruker 400 MHz Ultrashield
Bruker B-ACS60 Autosampler
Bruker Advance 400 Console
Bruker DPX250
Bruker AVANCE 500
Bruker DRX600

Software
User interface —NMR Kiosk
Controlling software —XWin NMR version 3.0

Chromatography

Unless stated otherwise, all column chromatography was carried out using silica columns.

Abbreviations
BINAP—(±)-2,2'-bis(diphenylphosphino)-1,1'-binaphthalene
BOC—tert-butyloxycarbonyl
'BuOH—tert-butanol
CCl$_4$—carbon tetrachloride
CDCl$_3$—deuteriochloroform
CuCl—copper (I) chloride
1,2-DCE—1,2-dichloroethane,
DCM—dichloromethane
Dibal-H—di-isobutyl aluminium hydride
DME—1,2-dimethoxyethane
DMF—N,N-dimethylformamide
DMSO—dimethyl sulfoxide
DMSO-d$_6$—dimethyl sulfoxide-d6
Et$_2$O—diethyl ether
EtOAc—ethyl acetate
EtOH—ethanol
HCl—hydrochloric acid, hydrogen chloride
HOBt—1-hydroxybenzotriazole
H$_2$SO$_4$—sulfuric acid
KOH—potassium hydroxide
MeOH—methanol
MgSO$_4$—magnesium sulfate
MnO$_2$—manganese dioxide
NaCl—sodium chloride
NaHCO$_3$—sodium hydrogen carbonate
NaIO$_4$—sodium periodate
NaOH—sodium hydroxide
Na$_2$SO$_4$—sodium sulfate
NH$_3$—ammonia
Pd/C—palladium on charcoal
PS-Trisamine
Pt/C—platinum on charcoal
SCX—strong cation exchanger
TFA—trifluoroacetic acid
THF—tetrahydrofuran
THMD—2,2,6,6-tetramethyl 3,5-heptanedione
Xantphos—4,5-bis(diphenylphosphino)-9,9-dimethylxanthene Description 1

1,1-Dimethylethyl (2S)-2-methyl-4-[(4-nitrophenyl)methyl]-1-piperazinecarboxylate (D1)

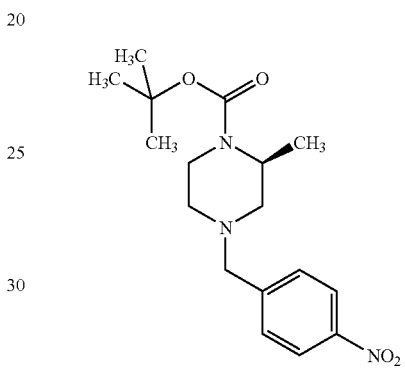

A mixture of 4-nitrobenzaldehyde (15.1 g, 0.1 mol), 1,1-dimethylethyl (2S)-2-methyl-1-piperazinecarboxylate hydrochloride (21.3 g, 0.09 mol), triethylamine (15 mL, 0.108 mol) and sodium tri(acetoxy)borohydride (42.4 g, 0.2 mol) in 1,2-DCE (500 mL) was stirred at room temperature overnight. Saturated aqueous NaHCO$_3$ solution (200 mL) was added and the mixture stirred for 20-30 minutes. The phases were separated and the aqueous phase was washed with DCM. The combined organics were washed with brine, dried and concentrated. Column chromatography eluting with 0-20% EtOAc/hexane gave the title compound as a pale yellow oil which crystallized on standing (25.61 g). δ$_H$ (CDCl$_3$, 400 MHz) 8.19 (2H, d), 7.53 (2H, d), 4.21 (1H, br.s), 3.83 (1H, d), 3.62 (1H, d), 3.50 (1H, d), 3.13 (1H, td), 2.74 (1H, m), 2.54 (1H, m), 2.20 (1H, dd), 2.08 (1H, m), 1.46 (9H, s), 1.25 (3H, d).

Description 1: Alternative Method (A)

1,1-Dimethylethyl (2S)-2-methyl-4-[(4-nitrophenyl)methyl]-1-piperazinecarboxylate (D1)

A mixture of 4-nitrobenzaldehyde (30.22 g, 0.2 mol), 1-dimethylethyl (2S)-2-methyl-1-piperazinecarboxylate (40.06 g, 0.2 mol) and sodium tri(acetoxy)borohydride (85 g, 0.4 mol) in 1,2-DCE (1 L) was stirred at room temperature over-weekend. The reaction mixture was treated portion-wise with NaHCO$_3$ solution (400 mL) over a period of ~2 h. After a further 30 mins, the organic layer was separated, washed with brine, dried and concentrated to give a viscous pale yellow oil. Purification by column chromatography eluting with 0%, 10% and then 20% EtOAc/hexane yielded the title compound as a yellow crystalline solid (61.1 g).

Description 2

1,1-Dimethylethyl (2S)-4-[(4-aminophenyl)methyl]-2-methyl-1-piperazinecarboxylate (D2)

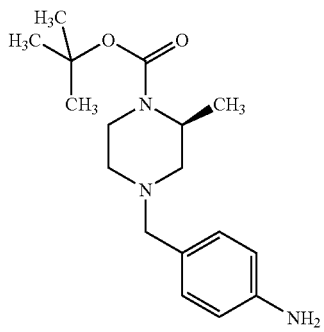

To 1,1-dimethylethyl (2S)-2-methyl-4-[(4-nitrophenyl)methyl]-1-piperazinecarboxylate (D1) (4.62 g, 13.78 mmol) and KOH (7.79 g, 138.8 mmol) in MeOH (100 mL) was added wet (50% w/w water) 10% Pd/C catalyst (4 g) and the mixture was hydrogenated at room temperature and atmospheric pressure for 40 mins. The catalyst was removed by filtration and the filtrate concentrated in vacuo. The residue was partitioned between DCM and water and aqueous layer was further extracted with DCM (×2). The combined organics were washed with brine, dried and concentrated to give the title compound as a colourless gum (4.14 g) which was used in the next step without further purification. $\delta_H$ (CDCl$_3$, 400 MHz) 7.10 (2H, d), 6.64 (2H, d), 4.16 (1H, br.s), 3.78 (1H, d), 3.62 (2H, s), 3.42 (1H, d), 3.28 (1H, d), 3.08 (1H, td), 2.74 (1H, m), 2.58 (1H, m), 2.06 (1H, dd), 1.95 (1H, m), 1.46 (9H, s), 1.21 (3H, d).

Description 2: Alternative Method (A)

1,1-Dimethylethyl (2S)-4-[(4-aminophenyl)methyl]-2-methyl-1-piperazinecarboxylate (D2)

To 1,1-dimethylethyl (2S)-2-methyl-4-[(4-nitrophenyl)methyl]-1-piperazinecarboxylate (D1) (15 g, 44.8 mol) in MeOH (150 mL) and water (150 mL) at 80° C. was added ammonium chloride (11.9 g, 0.224 mol) and iron powder (7.5 g, 0.134 mol) with vigorous stirring. The reaction was stirred at 80° C. for 2 h then filtered through Celite® while still hot and the filter cake was washed with further DCM. The filtrate layers were separated and the aqueous layer was washed with DCM (×3). The DCM layers were combined, dried (Na$_2$SO$_4$) and concentrated to give the crude product which was purified by column chromatography. Elution with 20-70% EtOAc/petroleum ether gave the title compound as a white solid (9.46 g).

Description 2: Alternative Method (B)

1,1-Dimethylethyl (2S)-4-[(4-aminophenyl)methyl]-2-methyl-1-piperazinecarboxylate (D2)

A mixture of 1,1-dimethylethyl (2S)-2-methyl-4-[(4-nitrophenyl)methyl]-1-piperazinecarboxylate (D1) (21.62 g, 0.0644 mol), triethylamine (40 mL) and 5% Pt/C catalyst (21 g, 56% w/w water) in MeOH (400 mL) was hydrogenated at room temperature and atmospheric pressure overnight. The catalyst was removed by filtration and washed with further MeOH. The filtrate was concentrated, re-dissolved in DCM (200 mL) and washed with 2M NaOH solution. The aqueous wash was re-extracted with DCM (×2, 100 mL) and all organic phases were combined, washed with brine, dried and concentrated to give the title compound (19.53 g) which was used in the next step without further purification.

Description 3

1,1-Dimethylethyl (2S)-2-methyl-4-{[4-(methylamino)phenyl]methyl}-1-piperazinecarboxylate (D3)

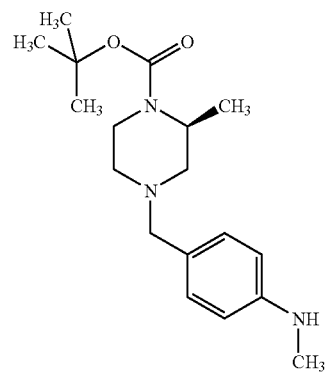

To 1,1-dimethylethyl (2S)-4-[(4-aminophenyl)methyl]-2-methyl-1-piperazinecarboxylate (D2) (4.14 g, 13.56 mmol) in dry MeOH (80 mL) at 50° C. under an argon atmosphere was added paraformaldehyde (1.22 g, 40.67 mmol) and sodium methoxide (3.65 g, 67.78 mmol). The mixture was stirred for ~24 h then sodium borohydride (1.54 g, 40.67 mmol) was added portion-wise and the reaction stirred at 50° C. overnight. After cooling to room temperature, acetone (10 mL) was added and the solvent removed in vacuo. The residue was partitioned between DCM and water and the organic phase was washed with brine, then dried and concentrated. Column chromatography gave the title compound as a colourless, crystalline solid (3.73 g). $\delta_H$ (CDCl$_3$, 400 MHz) 7.13 (2H, d), 6.57 (2H, d), 4.16 (1H, br.s), 3.78 (1H, d), 3.67 (1H, br.s), 3.42 (1H, d), 3.30 (1H, d), 3.08 (1H, td), 2.83 (3H, s), 2.75 (1H, m), 2.59 (1H, m), 2.06 (1H, dd), 1.94 (1H, m), 1.45 (9H, s), 1.21 (3H, d).

Description 3: Alternative Method (A)

1,1-Dimethylethyl (2S)-2-methyl-4-{[4-(methylamino)phenyl]methyl}-1-piperazinecarboxylate (D3)

A mixture of 1,1-dimethylethyl (2S)-4-[(4-aminophenyl)methyl]-2-methyl-1-piperazinecarboxylate (D2) (7.45 g, 24.43 mmol), paraformaldehyde (2.202 g, 73.28 mmol) and sodium methoxide (6.597 g, 122.13 mmol) in methanol (150 mL) under an argon atmosphere was heated at 50° C. overweekend. After cooling, sodium borohydride (1.848 g, 48.85 mmol) was added and the reaction mixture was heated at 50° C. for 1 h then cooled to room temperature. Acetone was added until no more bubbling was observed, then the mixture was concentrated. The residue was partitioned between DCM and water and the aqueous was re-extracted with DCM. The combined organics were diluted with MeOH (approx. 20 mL) to aid solubility, dried and concentrated to yield the title compound as an off white solid (7.77 g)

Description 3: Alternative Method (B)

1,1-Dimethylethyl (2S)-2-methyl-4-{[4-(methylamino)phenyl]methyl}-1-piperazinecarboxylate (D3)

1,1-Dimethylethyl (2S)-4-[(4-aminophenyl)methyl]-2-methyl-1-piperazinecarboxylate (D2) (19.53 g, 0.0639 mol) in dry MeOH (300 mL) under an argon atmosphere at room temperature was treated with paraformaldehyde (5.76 g, 0.1918 mol) and sodium methoxide (17.27 g, 0.3197 mol). The reaction mixture heated at 50° C., stirred overnight then cooled to room temperature. Sodium borohydride (7.26 g, 0.1918 mmol) was added portionwise and the reaction mixture was then re-heated to 50° C. and stirred for 2 days. The reaction mixture was cooled to rt and stirred for a further 24 h, then concentrated and re-dissolved in DCM (200 mL). Saturated aq. NaHCO₃ solution (200 mL) was added portionwise with stirring and on completion of addition the mixture was stirred at room temperature for a further 0.5 h. The DCM phase was separated, washed with brine, dried (MgSO₄) and concentrated to give a yellow oil which was purified by column chromatography. Elution with 0%, 10% and then 20% EtOAc/hexane yielded the title compound as a yellow oil which crystallised on standing (16.7 g).

Description 4

1,1-Dimethylethyl (2R)-2-methyl-4-[(4-nitrophenyl)methyl]-1-piperazinecarboxylate (D4)

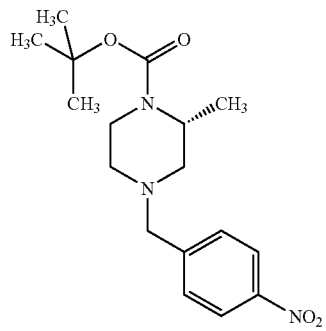

The title compound was prepared from 4-nitrobenzaldehyde and 1,1-dimethylethyl (2R)-2-methyl-1-piperazinecarboxylate hydrochloride using a method similar to that described for D1 in Description 1. MS (ES⁺): 280.2, 236.3, no molecular ion (MH⁺) observed Description 5

1,1-Dimethylethyl (2R)-4-[(4-aminophenyl)methyl]-2-methyl-1-piperazinecarboxylate (D5)

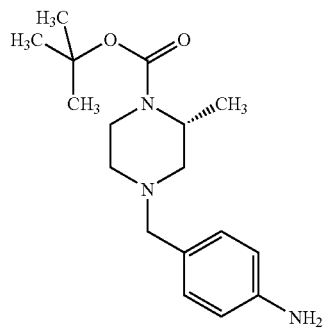

The title compound was prepared from 1,1-dimethylethyl (2R)-2-methyl-4-[(4-nitrophenyl)methyl]-1-piperazinecarboxylate (D4) using a method similar to that described for D2 in Description 2 although aq. 2M KOH solution was used in place of solid KOH and the reaction time was 40 minutes. MS (ES): MH⁺ 306.2, MNa⁺ 328.2.

Description 6

1,1-Dimethylethyl (2R)-2-methyl-4-{[4-(methylamino)phenyl]methyl}-1-piperazinecarboxylate (D6)

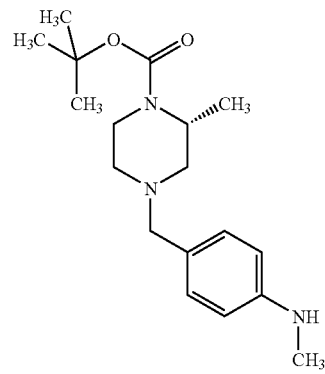

The title compound was prepared from 1,1-dimethylethyl (2R)-4-[(4-aminophenyl)methyl]-2-methyl-1-piperazinecarboxylate (D5) using a method similar to that described for D3 in Description 3A although the reaction was heated at 50° C. for 48 h prior to addition of sodium borohydride. $\delta_H$ (CDCl₃, 400 MHz) 7.13 (2H, d), 6.57 (2H, d), 4.16 (1H, m), 3.78 (1H, d), 3.42 (1H, d), 3.29 (1H, d), 3.08 (1H, td), 2.83 (3H, s), 2.75 (1H, m), 2.59 (1H, m), 2.07 (1H, dd), 1.94 (1H, m), 1.45 (9H, s), 1.21 (3H, d). MS (ES⁺): 342.3 (MNa⁺), 220.2, no molecular ion (MH⁺) observed.

Description 7

1,1-Dimethylethyl (2R,6S)-2,6-dimethyl-4-[(4-nitrophenyl)methyl]-1-piperazinecarboxylate (D7)

The title compound may be prepared using a method similar to that described for D1.

Description 7: Alternative Method (A)

1,1-Dimethylethyl (2R,6S)-2,6-dimethyl-4-[(4-nitrophenyl)methyl]-1-piperazinecarboxylate (D7)

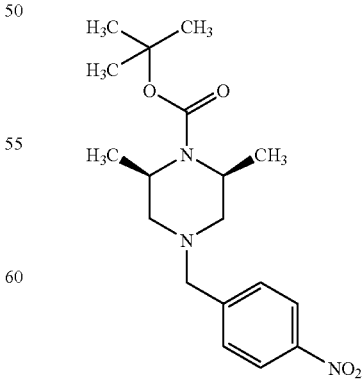

(3R,5S)-1-[(4-Nitrophenyl)methyl]-3,5-dimethylpiperazine (D82) (4.278 g, 17.17 mmol) was dissolved in dioxane (180 mL) and Boc anhydride (7.494 g, 34.34 mmol) and saturated aqueous NaHCO$_3$ solution (60 mL) were added. The mixture was stirred at room temperature overnight; the mixture was filtered and the filter cake washed with DCM. The filtrate was concentrated under vacuum and the residue partitioned between DCM and water. The DCM layer was separated and the aqueous was extracted with DCM (×2). The DCM layers were combined and dried to produce a yellow oil (9.614 g). The mixture was purified by passing through an SCX cartridge to produce a yellow oil (4.787 g) which was a mixture of the title compound and unreacted D82. This whole was dissolved in DCM (60 mL) and triethylamine (2.936 mL) added followed by Boc anhydride (4.612 g, 21.13 mmol). The mixture was stirred at room temperature overnight under argon. PS Trisamine® (6 g) was added and the mixture allowed to stir for 30 min; the polymer was filtered off and the solvent removed to produce a yellow oil (6.5621 g). Purification by column chromatography eluting with 0-50% Et$_2$O/petroleum ether gave a pale yellow solid (5.245 g). This solid was dissolved in MeOH and passed down an SCX cartridge (70 g) which was flushed with MeOH followed by 2M NH$_3$ in MeOH. The solvent was removed to produce a yellow solid (3.833 g) which was further purified by column chromatography. Elution with 0-50% Et$_2$O/petroleum ether gave the title compound as a whitish cream solid (2.624 g). MS (ES$^+$): 294.3, 250.3, no molecular ion (MH$^+$) observed.

Description 8

1,1-Dimethylethyl (2R,6S)-4-[(4-aminophenyl)methyl]-2,6-dimethyl-1-piperazinecarboxylate (D8)

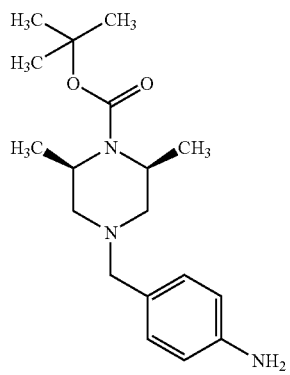

To a solution of 1,1-dimethylethyl (2R,6S)-2,6-dimethyl-4-[(4-nitrophenyl)methyl]-1-piperazinecarboxylate (D7) (2.62 g, 7.53 mmol) in MeOH (25 mL) and water (25 mL) heated to 80° C. was added iron powder (1.26 g, 22.54 mmol) and ammonium chloride (2.01 g, 37.58 mmol). The reaction was stirred vigorously at 80° C. for 1.5 h and then the iron residues removed by filtration through Celite®. The filtrate was concentrated and the residue partitioned between DCM and water. The aqueous layer was further extracted with DCM (×2) and the combined organics were dried and concentrated to give the crude product as a yellow foam (2.01 g). Column chromatography eluting with 0-100% Et$_2$O/petroleum ether gave the title compound (1.694 g). δ$_H$ (CDCl$_3$, 400 MHz) 7.12 (2H, d), 6.64 (2H, d), 4.05 (2H, m), 3.64 (2H, br s), 3.36 (2H, s), 2.59 (2 h, d), 2.06 (2H, dd), 1.46 (9H, s), 1.27 (6H, d). MS (ES): MH$^+$ 320.3, MNa$^+$ 342.3.

Description 9

1,1-Dimethylethyl (2R,6S)-2,6-dimethyl-4-{[4-(methylamino)phenyl]methyl}-1-piperazinecarboxylate (D9)

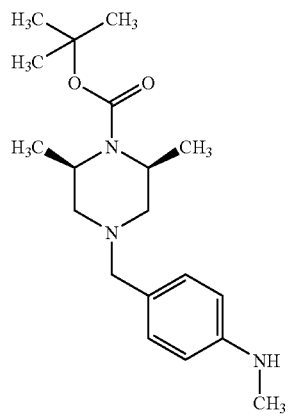

The title compound was prepared from 1,1-dimethylethyl (2R,6S)-4-[(4-aminophenyl)methyl]-2,6-dimethyl-1-piperazinecarboxylate (D8) using a method similar to that described for D3 in Description 3A although the reaction was heated at 50° C. for 48 h prior to addition of sodium borohydride then for 1 h after addition. Further paraformaldehyde (1 eq) and sodium methoxide (1 eq) were added; the reaction was heated at 50° C. for 12 h; further sodium borohydride (1 eq) was added and the reaction heated at 50° C. for 1 h. δ$_H$ (CDCl$_3$, 400 MHz) 7.16 (2H, d), 6.57 (2H, d), 4.05 (2H, m), 3.70 (1H, br s), 3.36 (2H, s), 2.82 (3H, s), 2.59 (2H, d), 2.06 (2H, dd), 1.49 (9H, s), 1.27 (6H, d). MS (ES$^+$): 356.3 (MNa$^+$), 234.3, no molecular ion (MH$^+$) observed.

Description 10

1,1-Dimethylethyl 4-[(4-nitrophenyl)methyl]-1-piperazinecarboxylate (D10)

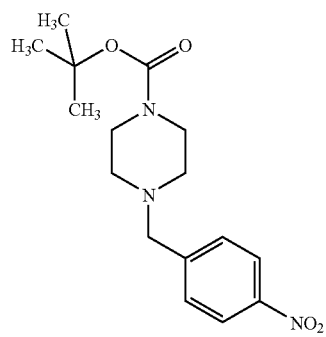

The title compound was prepared from 4-nitrobenzaldehyde and 1,1-dimethylethyl 1-piperazinecarboxylate using a method similar to that described for D1 in Description 1A although the product was purified by column chromatography followed by passing through an SCX column eluting with MeOH then 2M NH$_3$ in MeOH. MS (ES$^+$): 266.1, 222.2, no molecular ion (MH$^+$) observed.

Description 11

1,1-Dimethylethyl 4-[(4-aminophenyl)methyl]-1-piperazinecarboxylate (D11)

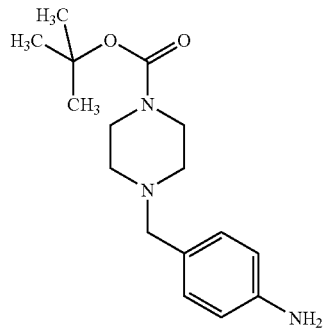

The title compound was prepared from D10 using a method similar to that described for D8 in Description 8 although no column chromatography was required. MS (ES): MH+ 292.1, MNa+ 314.2.

Description 12

1,1-Dimethylethyl 4-{[4-(methylamino)phenyl]methyl}-1-piperazinecarboxylate (D12)

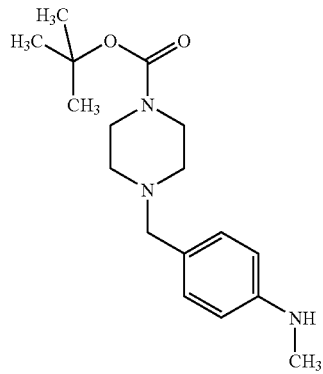

The title compound was prepared from D11 using a method similar to that described for D3 in Description 3A although the reaction was heated at 50° C. overnight prior to addition of sodium borohydride and no column chromatography was required. $\delta_H$ (CDCl$_3$, 400 MHz) 7.11 (2H, d), 6.57 (2H, d), 3.69 (1H, br.s), 3.40 (6H, m), 2.83 (3H, s), 2.36 (4H, m), 1.45 (9H, s) [δ values corrected for incorrectly referenced TMS at 0.58 ppm on spectrum]. MS (ES+): 206.2, no molecular ion (MH+) observed.

Description 13

Ethyl 6-[(4-fluorophenyl)oxy]-3-pyridinecarboxylate (D13)

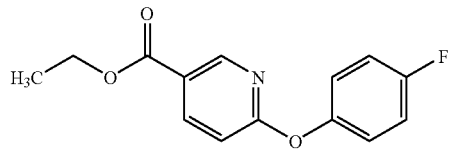

Sodium hydride (0.653 g, 60% in mineral oil, 16.338 mmol) was suspended in DMF (10 mL) under argon, and 4-fluorophenol (0.915 g, 8.169 mmol) added in two portions. The mixture was stirred for 20 minutes then ethyl 6-chloro-3-pyridinecarboxylate (1.515 g, 8.169 mmol) was added together with additional DMF (4 mL) added to aid solubility. The mixture was heated to 80° C. for 2.5 h. The reaction mixture was allowed to cool to room temperature and water (30 mL) was added. The solution was acidified to pH 3 with 2M HCl and extracted with ethyl acetate (×3). The combined ethyl acetate layers were dried and concentrated to produce a brown oil. The crude product was purified by chromatography. Elution with a 0-25% Et$_2$O/petroleum ether gradient gave the title compound as a colourless oil (0.284 g). $\delta_H$ (CDCl$_3$, 400 MHz) 8.81 (1H, dd), 8.28 (1H, dd), 7.11 (4H, m), 6.95 (1H, d), 4.37 (2H, q), 1.38 (3H, t). MS (ES): MH+ 262.2.

Description 14

6-[(4-Fluorophenyl)oxy]-3-pyridinecarboxylic acid (D14)

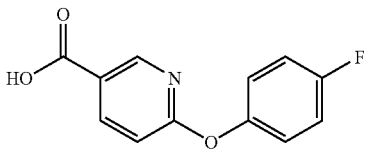

Ethyl 6-[(4-fluorophenyl)oxy]-3-pyridinecarboxylate (D13) (0.275 g, 1.054 mmol) was taken up in 1,4-dioxane (5 mL) and lithium hydroxide (0.050 g, 2.109 mmol) was dissolved in water. The two solutions were combined and stirred at room temperature for 2 h. The mixture was acidified to pH 5 with 2M HCl and concentrated. The residue was taken up in ethyl acetate, dried and concentrated to yield the title compound as a cream/white solid (0.233 g). $\delta_H$ (DMSO-d$_6$, 400 MHz) 13.20 (1H, bs), 8.65 (1H, dd), 8.28 (1H, dd), 7.26 (4H, m), 7.12 (1H, d). MS (ES): MH+ 234.2, (M-H+) 232.1.

Description 14: Alternative Method (A)

6-[(4-Fluorophenyl)oxy]-3-pyridinecarboxylic acid (D14)

A mixture of 4-fluorophenol (96.8 g), methyl 6-chloropyridine-3-carboxylate (30 g) and cesium carbonate (285.3 g) in DMSO (875 mL) was stirred and heated to 130° C. over a period of 1.75 h then cooled overnight. The reaction mixture was reheated to ~150° C. over a period of 1.5 h, kept at this temperature for ~1 h, then cooled to ~40° C. and poured into water (4 L). The aqueous solution was extracted with ether (1.0 L) then adjusted to pH7-8 by addition of 2M HCl. The solution was extracted with further ether (2×1.0 L), then adjusted to pH 2 by addition of 2M HCl causing precipitation of a solid. The precipitate was collected by filtration, washed with water and dried overnight at 40° C. in vacuo to give the title compound as a beige/pink solid (36.7 g).

Description 15

1,1-Dimethylethyl (2R,6S)-4-({4-[{[6-(4-fluorophenyl)-2-methyl-3-pyridinyl]carbonyl}(methyl)amino]phenyl}methyl)-2,6-dimethyl-1-piperazinecarboxylate (D15)

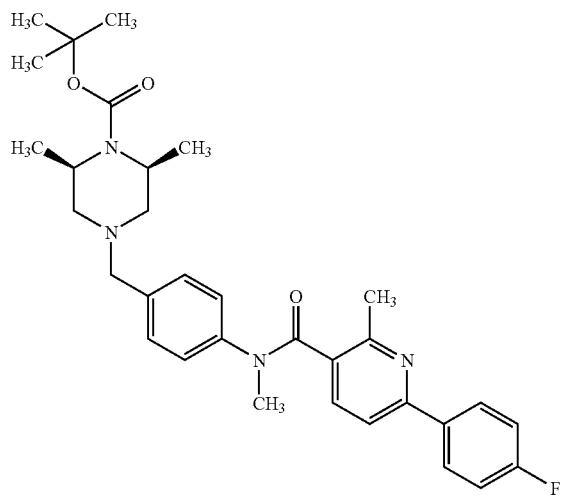

Step 1: 6-(4-Fluorophenyl)-2-methyl-3-pyridinecarboxylic acid (0.2 g, 0.866 mol) was suspended in DCM (14 mL) and DMF (1 drop) was added. The mixture was cooled in an ice-bath and oxalyl chloride (0.226 mL, 2.598 mmol) was added portion wise over 5 minutes. The mixture was heated to 40° C. for 90 minutes. The mixture was allowed to cool and the solvent removed under vacuum to give 6-(4-fluorophenyl)-2-methyl-3-pyridinecarbonyl chloride as a yellow solid (0.270 g) which was used directly in step 2.

Step 2: The acid chloride from step 1 was taken up in DCM (3 mL) and added to a solution of 1,1-dimethylethyl (2R,6S)-2,6-dimethyl-4-{[4-(methylamino)phenyl]methyl}-1-piperazinecarboxylate (D9) (0.23 g, 0.693 mmol) in DCM (2 mL). Triethylamine (0.193 mL, 1.386 mmol) was added and the mixture was stirred overnight at room temperature. The reaction mixture was diluted with DCM and washed with water. The aqueous layer was re-extracted with DCM (×2) and the combined organics were dried and concentrated. The crude product was purified by column chromatography. Elution with 0-50% EtOAc/petroleum yielded the title compound as a white foam (0.331 g). $\delta_H$ (CDCl$_3$, 400 MHz) 7.89 (2H, m), 7.36 (1H, m), 7.26 (1H, m), 7.19 (2H, m), 7.10 (2H, t), 6.99 (2H, m), 4.00 (2H, m), 3.53 (3H, s), 3.34 (2H, s), 2.58 (3H, s), 2.44 (2H, d), 2.05 (2H, m), 1.44 (9H, s), 1.18 (6H, d). MS (ES): MH$^+$ 547.3.

Description 16

1,1-Dimethylethyl (2S)-4-({4-[({6-[(4-fluorophenyl)oxy]-3-pyridinyl}carbonyl)(methyl)amino]phenyl}methyl)-2-methyl-1-piperazinecarboxylate (D16)

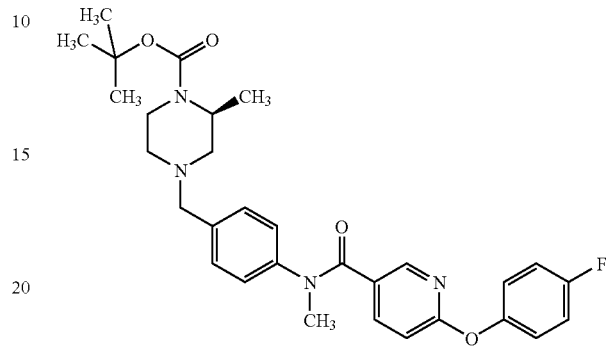

Step 1: 6-[(4-Fluorophenyl)oxy]-3-pyridinecarboxylic acid (D14) (0.232 g, 0.994 mmol) was dissolved in 1,4-dioxane (6 mL) and thionyl chloride (0.363 mL, 4.972 mmol) added dropwise. The mixture was heated at reflux for 3.5 h, then cooled and concentrated in vacuo. DCM was added to the residue which was then re-concentrated to yield 6-[(4-fluorophenyl)oxy]-3-pyridinecarbonyl chloride as a yellow oil (0.252 g) which was used directly in step 2.

Step 2: The acid chloride from step 1 was taken up in DCM (3 mL) and added to 1,1-dimethylethyl (2S)-2-methyl-4-{[4-(methylamino)phenyl]methyl}-1-piperazinecarboxylate (D3) (0.288 g, 0.904 mmol) in DCM (3 mL). Triethylamine (0.251 mL, 1.808 mmol) was added and the mixture was stirred at room temperature overnight. The reaction mixture was diluted with DCM and washed with water. The aqueous was extracted with DCM (×2) and the combined organic layers were dried and concentrated. The crude product was purified by column chromatography. Elution with a 0-50% EtOAc/petroleum ether gradient gave the title compound as a colourless oil (0.518 g). $\delta_H$ (CDCl$_3$, 400 MHz) 8.07 (1H, m), 7.65 (1H, dd), 7.24 (2H, d), 7.03 (6H, m), 6.70 (1H, d), 4.18 (1H, br.s), 3.80 (1H, d), 3.48 (3H, s), 3.46 (1H, d), 3.34 (1H, d), 3.08 (1H, td), 2.70 (1H, d), 2.50 (1H, d), 2.10 (1H, dd), 2.00 (1H, m), 1.46 (9H, s), 1.20 (3H, d). MS (ES): MH$^+$ 535.3.

Description 16: Alternative Method (A)

1,1-Dimethylethyl (2S)-4-({4-[({6-[(4-fluorophenyl)oxy]-3-pyridinyl}carbonyl)(methyl)amino]phenyl}methyl)-2-methyl-1-piperazinecarboxylate (D16)

6-[(4-Fluorophenyl)oxy]-3-pyridinecarboxylic acid (D14) (20.1 g, 0.0862 mol) was dissolved in 1,4-dioxane (400 mL) and thionyl chloride (28.5 mL, 4.972 mmol) added cautiously. The mixture was heated slowly to reflux and stirred for 4.5 h. The reaction mixture was allowed to cool and concentrated. Dioxane (200 mL) was added and the solution was re-concentrated (×2) to give crude 6-[(4-fluorophenyl)oxy]-3-pyridinecarbonyl chloride which was re-dissolved in DCM (250 mL). This was added dropwise to a solution of 1,1-dimethylethyl (2S)-2-methyl-4-{[4-(methylamino)phenyl]methyl}-1-piperazinecarboxylate (D3) (25 g, 0.0783 mol, prepared in three different batches according to method D3B and consolidated) and triethylamine (14 mL, 0.1004 mol) in DCM (250 mL) cooled in an ice/water bath over 30 mins. The reaction mixture was warmed to room temperature and stirred for ~15 h. The reaction mixture was washed with 2M NaOH solution (2×200 mL) and brine, then dried over $MgSO_4$ and concentrated in vacuo to give a brown foam/gum. The crude product was purified by chromatography to give the title compound as a colourless foam (32.39 g).

Tabulated compounds D17, D40 and D41 were prepared using methods similar to those described in Description 15 using the appropriate aniline precursor and appropriate carboxylic acid.

Tabulated compounds D18-D53 (excepting D40 and D41) were prepared using methods similar to those described in Description 16 using the appropriate aniline precursor and appropriate carboxylic acid.

| | Aniline | | | Method Comment | | |
|---|---|---|---|---|---|---|
| Desc'n | precursor | Structure | Name | Step 1 | Step 2 | MH+ |
| D17 | D3 | | 1,1-dimethylethyl (2S)-4-({4-[{[6-(4-fluorophenyl)-3-pyridinyl]carbonyl}(methyl)amino]phenyl}methyl)-2-methyl-1-piperazinecarboxylate | Similar method to D15 although reaction temp./time: 0° C./20 mins then room temperature/1 h | Similar method to D15 although additional purification by MDAP | 519.2 |
| D18 | D3 | | 1,1-dimethylethyl (2S)-2-methyl-4-{[4-(methyl{[6-(4-morpholinyl)-3-pyridinyl]carbonyl}amino)phenyl]methyl}-1-piperazinecarboxylate | Similar method to D16 although reaction temp./time: room temperature, overnight | Similar method to D16 although reaction time: over-weekend | 510 |

-continued

| Desc'n | Aniline precursor | Structure | Name | Method Comment Step 1 | Method Comment Step 2 | MH+ |
|---|---|---|---|---|---|---|
| D19 | D3 | 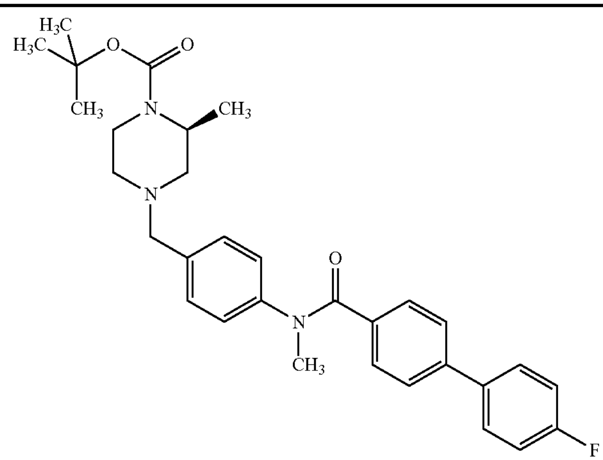 | 1,1-dimethylethyl (2S)-4-({4-[[(4'-fluoro-4-biphenylyl)carbonyl](methyl)amino]phenyl}methyl)-2-methyl-1-piperazinecarboxylate | Similar method to D16 although reaction temp./time: room temperature, overnight then reflux, 3 h | Similar method to D16 although reaction time: over-weekend | 518.2 |
| D20 | D2 | 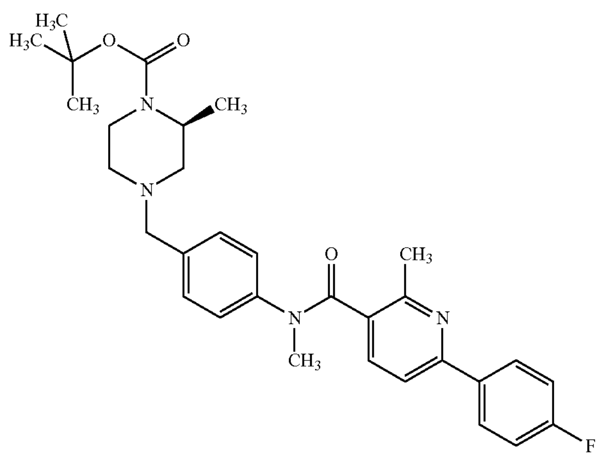 | 1,1-dimethylethyl (2S)-4-{[4-({[6-(4-fluorophenyl)-2-methyl-3-pyridinyl]carbonyl}amino)phenyl]methyl}-2-methyl-1-piperazinecarboxylate | Similar method to D16 although reaction temp/time: room temperature, ~3 h | Similar method to D16 | 519.4 |

-continued

| Desc'n | Aniline precursor | Structure | Name | Method Comment Step 1 | Method Comment Step 2 | MH+ |
|---|---|---|---|---|---|---|
| D21 | D3 | | 1,1-dimethylethyl (2S)-4-({4-[({1-[(3-fluorophenyl)carbonyl]-4-piperidinyl}carbonyl)(methyl)amino]phenyl}methyl)-2-methyl-1-piperazinecarboxylate | Similar method to D16 although reaction temp./time: room temperature, ~0.5 h | Similar method to D16 | 553.3 |
| D22 | D3 | | 1,1-dimethylethyl (2S)-4-({4-[({1-[(3-fluorophenyl)methyl]-4-piperadinyl}carbonyl)(methyl)amino]phenyl}methyl)-2-methyl-1-piperazinecarboxylate | Similar method to D16 although reaction temp./time: room temperature, 1 h | Similar method to D16 although reaction time: over-weekend | 539.3 |

| Desc'n | Aniline precursor | Structure | Name | Method Comment Step 1 | Method Comment Step 2 | MH+ |
|---|---|---|---|---|---|---|
| D23 | D3 | 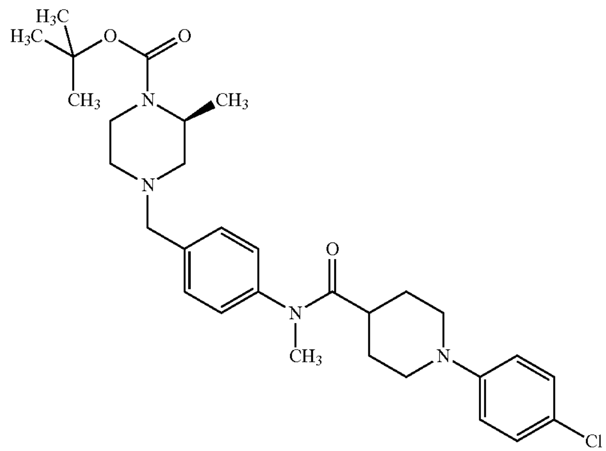 | 1,1-dimethylethyl (2S)-4-({4-[{(1-(4-chlorophenyl)-4-piperidinyl]carbonyl}(methyl)amino]phenyl}methyl)-2-methyl-1-piperazinecarboxylate | Similar method to D16 although reaction temp./time: room temperature, 1 h | Similar method to D16 | 541.4 |
| D24 | D3 | 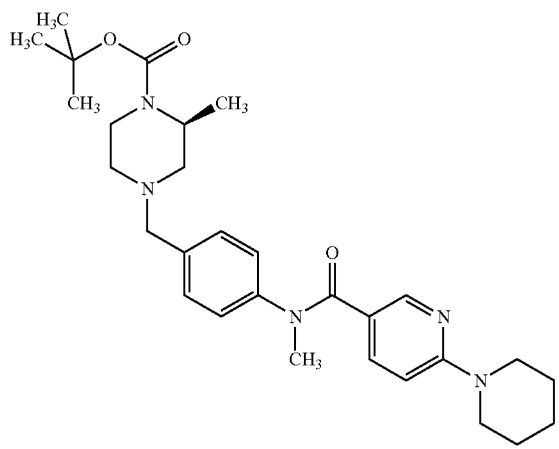 | 1,1-dimethylethyl (2S)-2-methyl-4-{[4-(methyl{[6-(1-piperidinyl)-3-pyridinyl]carbonyl}amino)phenyl]methyl}-1-piperazinecarboxylate | Similar method to D16 although reaction temp: room temperature, | Similar method to D16 although reaction time: 1 h | 508.4 |

-continued

| Desc'n | Aniline precursor | Structure | Name | Method Comment Step 1 | Method Comment Step 2 | MH+ |
|---|---|---|---|---|---|---|
| D25 | D3 | 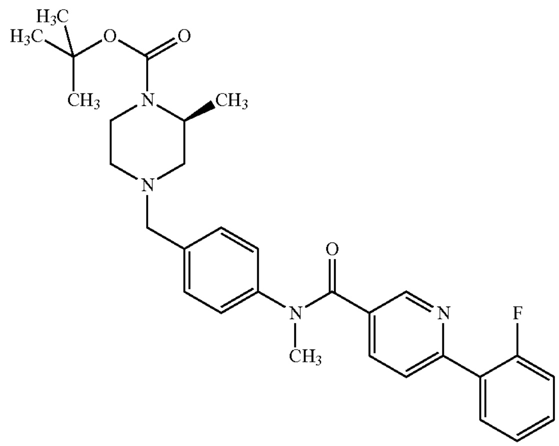 | 1,1-dimethylethyl (2S)-4-({4-[{[6-(2-fluorophenyl)-3-pyridinyl]carbonyl}(methyl)amino]phenyl}methyl)-2-methyl-1-piperazinecarboxylate | Similar method to D16 although reaction time: 40 mins. | Similar method to D16 | 519.2 |
| D26 | D3 | 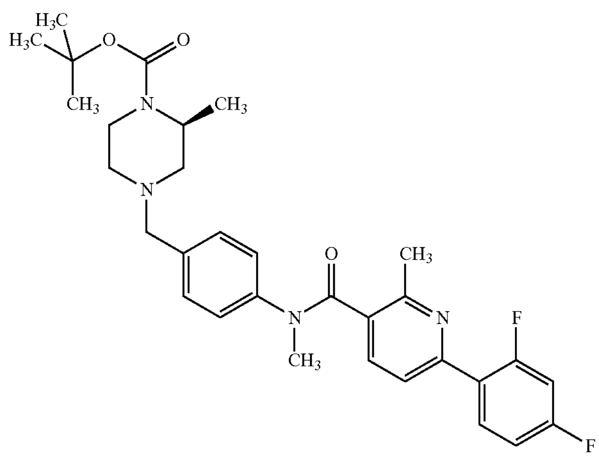 | 1,1-dimethylethyl (2S)-4-({4-[{[6-(2,4-difluorophenyl)-2-methyl-3-pyridinyl]carbonyl}(methyl)amino]phenyl}methyl)-2-methyl-1-piperazinecarboxylate | Similar method to D16 although reaction time: 1.5 h. | Similar method to D16 | 551.3 |

-continued

| Desc'n | Aniline precursor | Name | Structure | Method Comment Step 1 | Method Comment Step 2 | MH+ |
|---|---|---|---|---|---|---|
| D27 | D3 | 1,1-dimethylethyl (2S)-4-({4-[{[6-(3,4-difluorophenyl)-2-methyl-3-pyridinyl]carbonyl}(methyl)amino]phenyl}methyl)-2-methyl-1-piperazinecarboxylate | 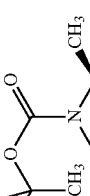 | Similar method to D16 although reaction time: 0.75 h. | Similar method to D16 | 551.3 |
| D28 | D3 | 1,1-dimethylethyl (2S)-4-({4-[{[6-(3-fluorophenyl)-2-methyl-3-pyridinyl]carbonyl}(methyl)amino]phenyl}methyl)-2-methyl-1-piperazinecarboxylate | 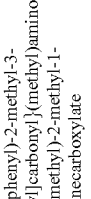 | Similar method to D16 although reaction time: 0.75 h | Similar method to D16 | 533.2 |

-continued

| Desc'n | Aniline precursor | Structure | Name | Method Comment Step 1 | Method Comment Step 2 | MH+ |
|---|---|---|---|---|---|---|
| D29 | D3 | 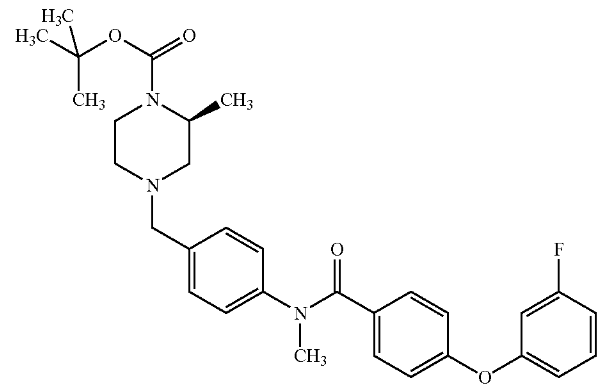 | 1,1-dimethylethyl (2S)-4-({4-[({4-[(3-fluorophenyl)oxy]phenyl}carbonyl)(methyl)amino]phenyl}methyl)-2-methyl-1-piperazinecarboxylate | Similar method to D16 although reaction temp./time: room temperature, 4 h; 50° C., 3 h, 100° C., overnight | Similar method to D16 although reaction time: 4 h | 534.3 |
| D30 | D3 | 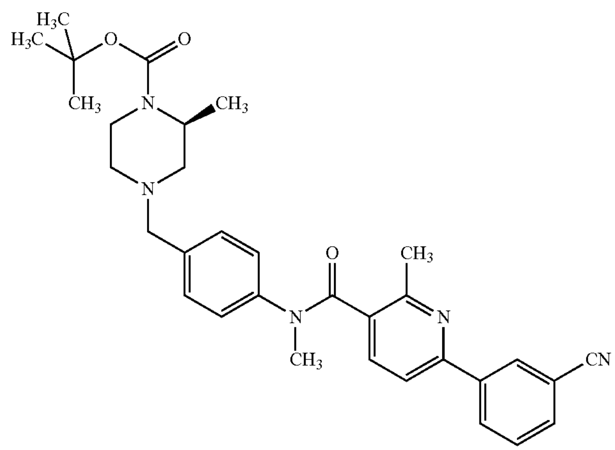 | 1,1-dimethylethyl (2S)-4-({4-[{[6-(3-cyanophenyl)-2-methyl-3-pyridinyl]carbonyl}(methyl)amino]phenyl}methyl)-2-methyl-1-piperazinecarboxylate | Similar method to D16 although reaction time: 3 h. | Similar method to D16 although reaction time: over-weekend | 540.3 |

-continued

| Desc'n | Aniline precursor | Structure | Name | Method Comment Step 1 | Method Comment Step 2 | MH+ |
|---|---|---|---|---|---|---|
| D31 | D3 | 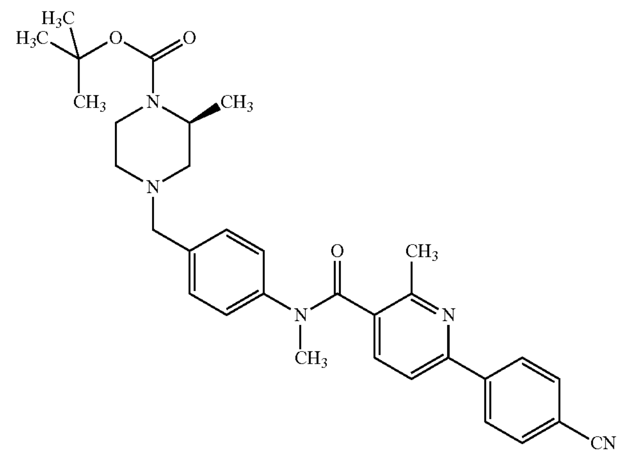 | 1,1-dimethylethyl (2S)-4-({4-[{[6-(4-cyanophenyl)-2-methyl-3-pyridinyl]carbonyl}(methyl)amino]phenyl}methyl)-2-methyl-1-piperazinecarboxylate | Similar method to D16 although reaction time: 3 h. | Similar method to D16 although reaction time: over-weekend | 540.3 |
| D32 | D3 | 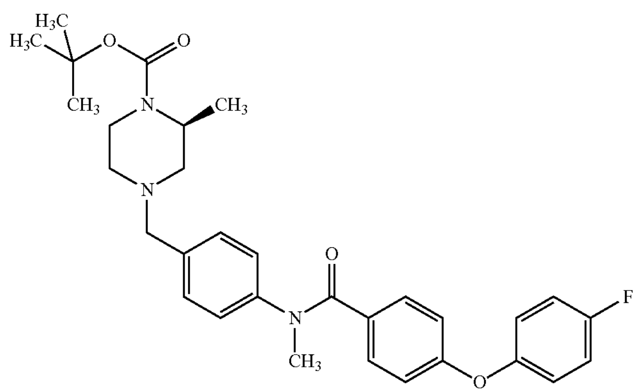 | 1,1-dimethylethyl (2S)-4-({4-[({4-[(4-fluorophenyl)oxy]phenyl}carbonyl)(methyl)amino]phenyl}methyl)-2-methyl-1-piperazinecarboxylate | Similar method to D16 although reaction temp./time: 100° C., overnight | Similar method to D16 although reaction time: over-weekend | 534.2 |

| Desc'n | Aniline precursor | Name | Structure | Method Comment Step 1 | Method Comment Step 2 | MH+ |
|---|---|---|---|---|---|---|
| D33 | D3 | 1,1-dimethylethyl (2S)-4-({4-[{(2-[(4-fluorophenyl)oxy]phenyl}carbonyl)(methyl)amino]phenyl}methyl)-2-methyl-1-piperazinecarboxylate | 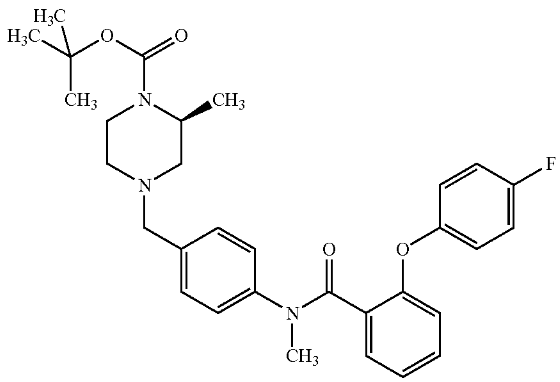 | Similar method to D16 although reaction temp./time: 100° C., overnight | Similar method to D16 although reaction time: over-weekend | 534.2 |
| D34 | D9 | 1,1-dimethylethyl (2R,6S)-4-({4-[{[6-(4-fluorophenyl)-3-pyridinyl]carbonyl}(methyl)amino]phenyl}methyl)-2,6-dimethyl-1-piperazinecarboxylate | 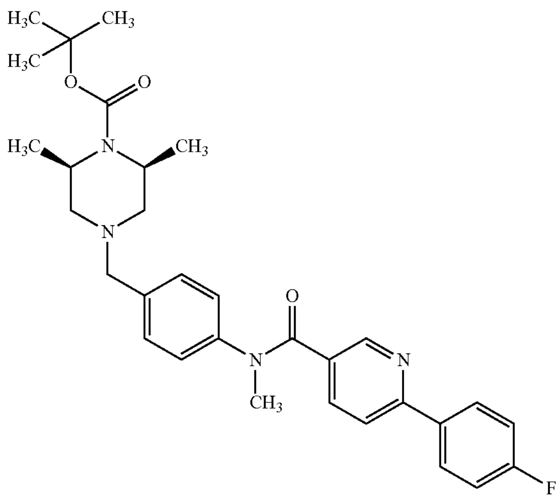 | Similar method to D16 although reaction time: 3 h. | Similar method to D16 | 533.3 |

| Desc'n | Aniline precursor | Structure | Name | Method Comment Step 1 | Method Comment Step 2 | MH+ |
|---|---|---|---|---|---|---|
| D35 | D3 | 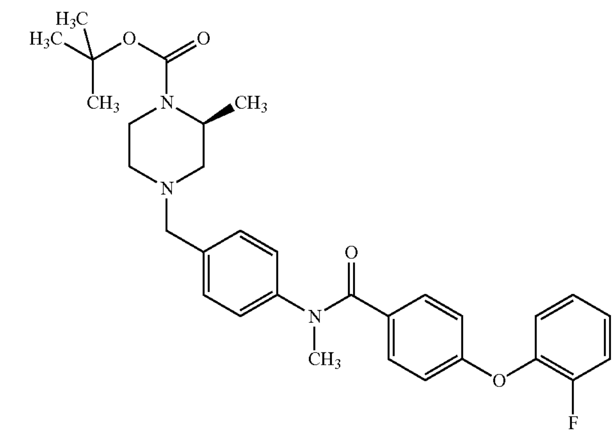 | 1,1-dimethylethyl (2S)-4-({4-[({4-[(2-fluorophenyl)oxy]phenyl}carbonyl)(methyl)amino]phenyl}methyl)-2-methyl-1-piperazinecarboxylate | Similar method to D16 although reaction temp./time: 100° C., overnight | Similar method to D16 although reaction time: 3 h and no column chromatography | 534.2 |
| D36 | D3 | 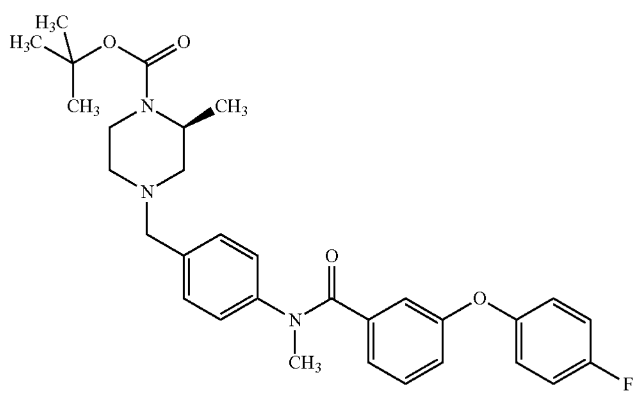 | 1,1-dimethylethyl (2S)-4-({4-[({3-[(4-fluorophenyl)oxy]phenyl}carbonyl)(methyl)amino]phenyl}methyl)-2-methyl-1-piperazinecarboxylate | Similar method to D16 although reaction temp./time: 100° C., overnight | Similar method to D16 although reaction time: 3 h and no column chromatography | 534.2 |

-continued

| Desc'n | Aniline precursor | Structure | Name | Method Comment Step 1 | Method Comment Step 2 | MH+ |
|---|---|---|---|---|---|---|
| D37 | D3 | 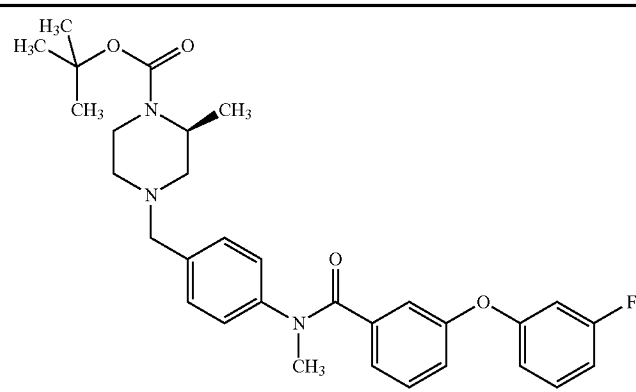 | 1,1-dimethylethyl (2S)-4-({4-[({3-[(3-fluorophenyl)oxy]phenyl}carbonyl)(methyl)amino]phenyl}methyl)-2-methyl-1-piperazinecarboxylate | Similar method to D16 although reaction temp./time: 100° C., overnight | Similar method to D16 although reaction time: 2 h and no column chromatography | 534.2 |
| D38 | D3 | 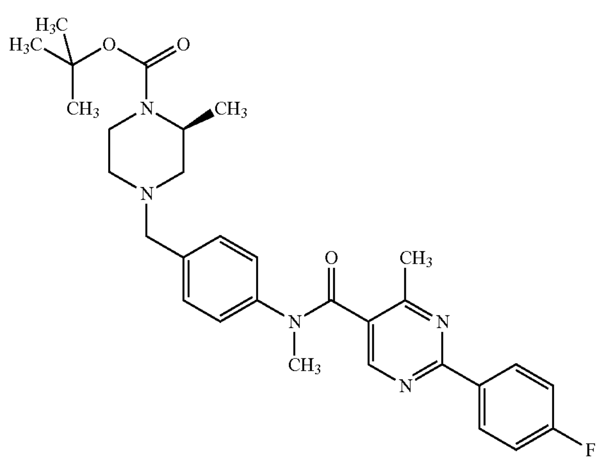 | 1,1-dimethylethyl (2S)-4-({4-[{[2-(4-fluorophenyl)-4-methyl-5-pyrimidinyl]carbonyl}(methyl)amino]phenyl}methyl)-2-methyl-1-piperazinecarboxylate | Similar method to D16 although reaction time: 1 h. | Similar method to D16 although reaction time: 12 h | 534.3 |

-continued

| Desc'n | Aniline precursor | Structure | Name | Method Comment Step 1 | Method Comment Step 2 | MH+ |
|---|---|---|---|---|---|---|
| D39 | D3 | 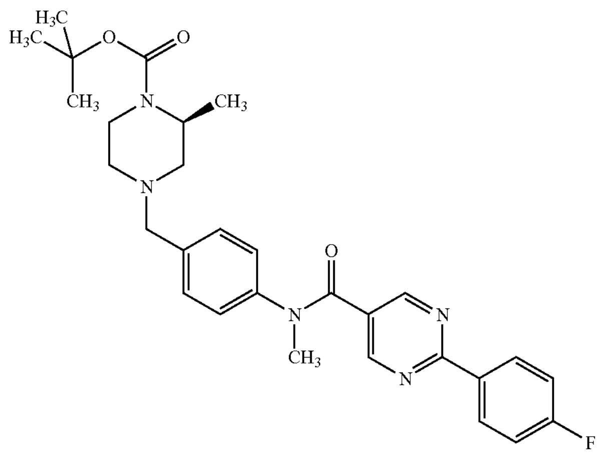 | 1,1-dimethylethyl (2S)-4-({4-[{[2-(4-fluorophenyl)-5-pyrimidinyl]carbonyl}(methyl)amino]phenyl}methyl)-2-methyl-1-piperazinecarboxylate | Similar method to D16 although reaction time: 1 h. | Similar method to D16 although reaction time: 3 h and no column chromatography | 520.3 |
| D40 | D6 | 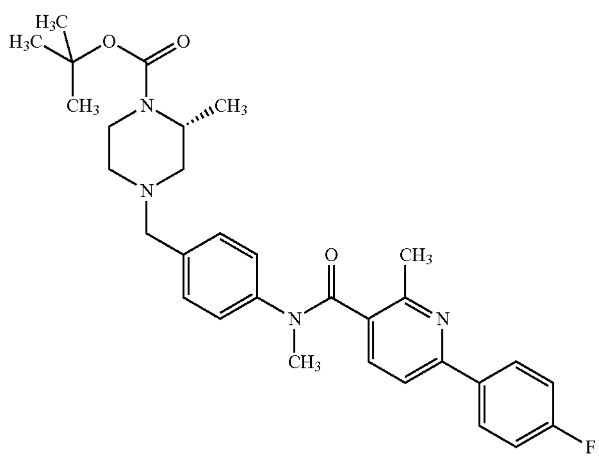 | 1,1-dimethylethyl (2R)-4-({4-[{[6-(4-fluorophenyl)-2-methyl-3-pyridinyl]carbonyl}(methyl)amino]phenyl}methyl)-2-methyl-1-piperazinecarboxylate | Similar method to D15 | Similar method to D15 | 533.3 |

-continued

| Desc'n | Aniline precursor | Structure | Name | Method Comment Step 1 | Method Comment Step 2 | MH+ |
|---|---|---|---|---|---|---|
| D41 | D6 | 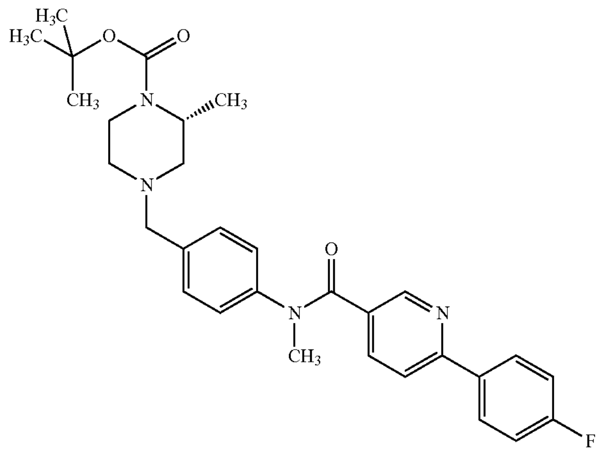 | 1,1-dimethylethyl (2R)-4-({4-[{[6-(4-fluorophenyl)-3-pyridinyl]carbonyl}(methyl)amino]phenyl}methyl)-2-methyl-1-piperazinecarboxylate | Similar method to D15 | Similar method to D15 | 519.3 |
| D42 | D3 | 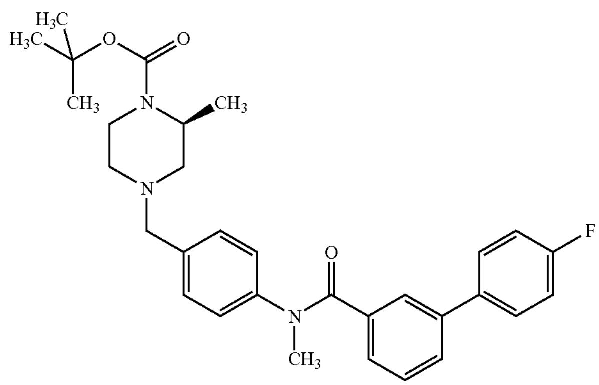 | 1,1-dimethylethyl (2S)-4-({4-[(4'-fluoro-3-biphenylyl)carbonyl](methyl)amino]phenyl}methyl)-2-methyl-1-piperazinecarboxylate | Similar method to D16 although reaction time: 1 h. | Similar method to D16 although reaction time: over-weekend | 518.3 |

-continued

| Desc'n | Aniline precursor | Structure | Name | Method Comment Step 1 | Method Comment Step 2 | MH+ |
|---|---|---|---|---|---|---|
| D43 | D3 | 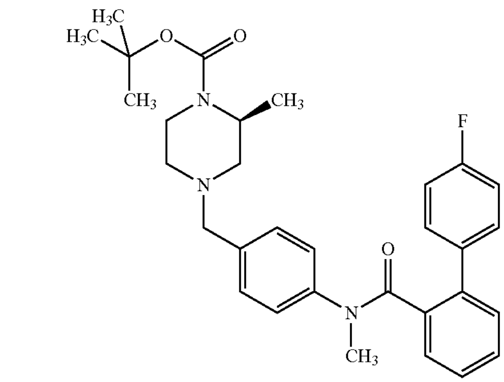 | 1,1-dimethylethyl (2S)-4-({4-[[(4'-fluoro-2-biphenylyl)carbonyl](methyl)amino]phenyl}methyl)-2-methyl-1-piperazinecarboxylate | Similar method to D16 although reaction time: 1 h. | Similar method to D16 although reaction time: over-weekend | 518.3 |
| D44 | D3 | 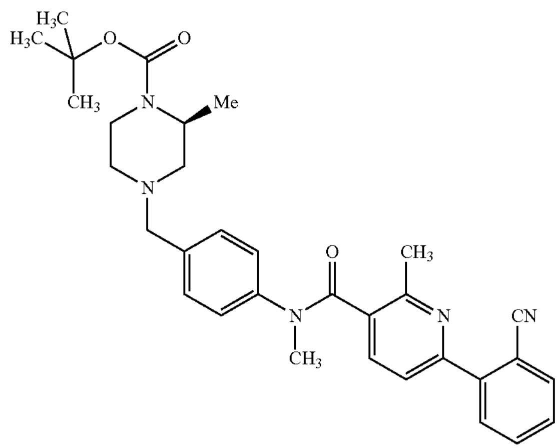 | 1,1-dimethylethyl (2S)-4-({4-[{[6-(2-cyanophenyl)-2-methyl-3-pyridinyl]carbonyl}(methyl)amino]phenyl}methyl)-2-methyl-1-piperazinecarboxylate | Similar method to D16 although reaction time: 1 h. | Similar method to D16 | 541.3 |

-continued

| Desc'n | Aniline precursor | Structure | Name | Method Comment Step 1 | Method Comment Step 2 | MH+ |
|---|---|---|---|---|---|---|
| D45 | D12 | (structure) | 1,1-dimethylethyl 4-({4-[{[6-(3-fluorophenyl)-3-pyridinyl]carbonyl}(methyl)amino]phenyl}methyl)-1-piperazinecarboxylate | Similar method to D16 although reaction temp./time: 100° C., 1 h | Similar method to D16 although reaction time: 4 h | 505.3 |
| D46 | D12 | (structure) | 1,1-dimethylethyl 4-({4-[{[6-(3-fluorophenyl)-2-methyl-3-pyridinyl]carbonyl}(methyl)amino]phenyl}methyl)-1-piperazinecarboxylate | Similar method to D16 carried out at room temperature, overnight; then 50° C., 2 h. Extra thionyl chloride (2 eq.) was added, then heated at 50° C., 2 h and 75° C., 2 h. | Similar method to D16 | 519.3 |

-continued

| Desc'n | Aniline precursor | Name | Structure | Method Comment Step 1 | Method Comment Step 2 | MH+ |
|---|---|---|---|---|---|---|
| D47 | D81 | 1,1-dimethylethyl (2S)-4-[{4-[({6-(3-fluorophenyl)-3-pyridinyl]carbonyl}(methyl)amino]-2-methylphenyl}methyl)-2-methyl-1-piperazinecarboxylate | 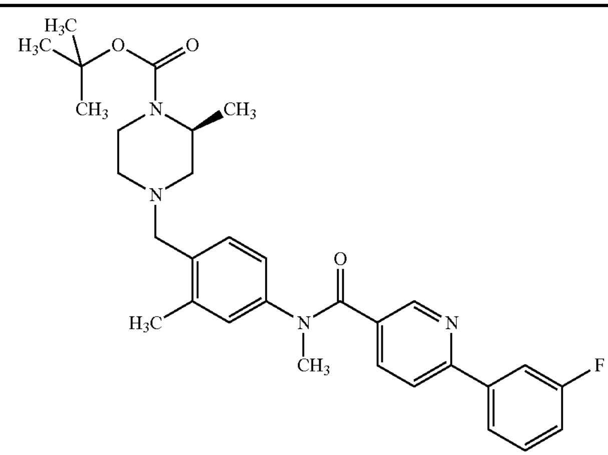 | Similar method to D16 although reaction time: 1.5 h. | Similar method to D16 although reaction time: 4 days | 533.3 |
| D48 | D3 | 1,1-dimethylethyl (2S)-4-[{4-[({6-(3-cyanophenyl)-3-pyridinyl]carbonyl}(methyl)amino]phenyl}methyl)-2-methyl-1-piperazinecarboxylate | 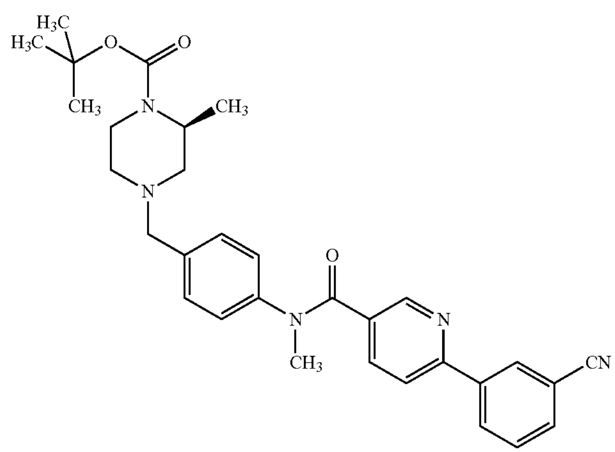 | Similar method to D16 although reaction time: 1.25 h. | Similar method to D16 | 526.3 |

-continued

| Desc'n | Aniline precursor | Structure | Name | Method Comment Step 1 | Method Comment Step 2 | MH+ |
|---|---|---|---|---|---|---|
| D49 | D3 | (structure shown) | 1,1-dimethylethyl (2S)-4-({4-[{[6-(2-cyanophenyl)-3-pyridinyl]carbonyl}(methyl)amino]phenyl}methyl)-2-methyl-1-piperazinecarboxylate | Similar method to D16 although reaction time: 1.25 h. | Similar method to D16 | 526.2 |
| D50 | D64 | (structure shown) | 1,1-dimethylethyl (2S)-4-({3-fluoro-4-[{[6-(3-fluorophenyl)-3-pyridinyl]carbonyl}(methyl)amino]phenyl}methyl)-2-methyl-1-piperazinecarboxylate | Similar method to D16 although reaction time: 1-2 h. | Similar method to D16 but no aq. work-up. Concentrated reaction mixture purified directly by column chromatography | 537.1 |

-continued

| Desc'n | Aniline precursor | Structure | Name | Method Comment Step 1 | Method Comment Step 2 | MH+ |
|---|---|---|---|---|---|---|
| D51 | D3 | | 1,1-dimethylethyl (2S)-4-({4-[({1-[(3,4-difluorophenyl)methyl]-4-piperidinyl}carbonyl)(methyl)amino]phenyl}methyl)-2-methyl-1-piperazinecarboxylate | Similar method to D16 although reaction time: ~1 h. | Similar method to D16 | 557.2 |
| D52 | D3 | | 1,1-dimethylethyl (2S)-4-({4-[({1-[(4-fluorophenyl)methyl]-4-piperidinyl}carbonyl)(methyl)amino]phenyl}methyl)-2-methyl-1-piperazinecarboxylate | Similar method to D16 although reaction time: 50 mins. | Similar method to D16 although reaction time: ~1.5 days | 539.9 |

-continued

| Desc'n | Aniline precursor | Structure | Name | Method Comment Step 1 | Method Comment Step 2 | MH+ |
|---|---|---|---|---|---|---|
| D53 | D67 | 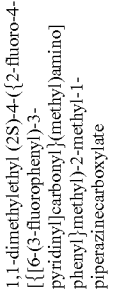 | 1,1-dimethylethyl (2S)-4-({2-fluoro-4-[{[6-(3-fluorophenyl)-3-pyridinyl]carbonyl}(methyl)amino]phenyl}methyl)-2-methyl-1-piperazinecarboxylate | Similar method to D16 although reaction time: 1-2 h. | Similar method to D16 although reaction time: over-weekend. No aq. work-up - reaction mixture concentrated and purified directly by column chromatography | 537.2 |

Description 54

1,1-Dimethylethyl (2S)-4-({4-[[(6-chloro-3-pyridinyl)carbonyl](methyl)amino]phenyl}methyl)-2-methyl-1-piperazinecarboxylate (D54)

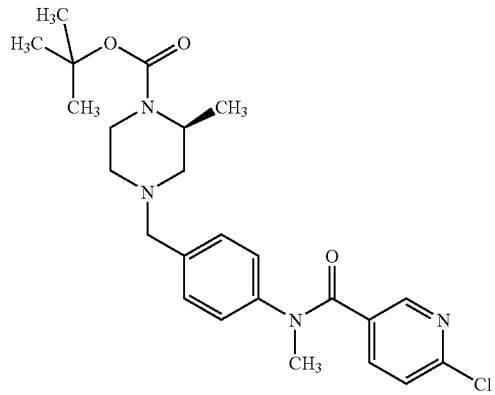

1,1-Dimethylethyl (2S)-2-methyl-4-{[4-(methylamino)phenyl]methyl}-1-piperazine-carboxylate (D3) (0.4 g, 1.254 mmol) was taken up in DCM (4 mL) under argon. 6-Chloro-3-pyridinecarbonyl chloride (0.243 g, 1.379 mmol) in DCM (4 mL) and triethylamine (0.348 mL, 2.508 mmol) were added. The mixture was stirred at room temperature overnight. The mixture was diluted with DCM and washed with water. The aqueous layer was extracted with DCM (×2) and the combined organics dried and concentrated to a pale yellow oil. The crude product was purified by column chromatography. Elution with a 0-50% EtOAc/petroleum ether gradient yielded the title compound as a white foam/gum (0.601 g). $\delta_H$ (CDCl$_3$, 400 MHz) 8.21 (1H, d), 7.61 (1H, dd), 7.25 (2H, d), 7.16 (1H, d), 6.99 (2H, d), 4.18 (1H, br.s), 3.80 (1H, d), 3.50 (3H, s), 3.47 (1H, d), 3.34 (1H, d), 3.10 (1H, td), 2.70 (1H, d), 2.49 (1H, d), 2.10 (1H, dd), 2.00 (1H, m), 1.46 (9H, s), 1.20 (3H, d). MS (ES): MH$^+$ 459.2.

Description 55

1,1-Dimethylethyl (2S)-4-({4-[({6-[(2-fluorophenyl)oxy]-3-pyridinyl}carbonyl)(methyl)amino]phenyl}methyl)-2-methyl-1-piperazinecarboxylate (D55)

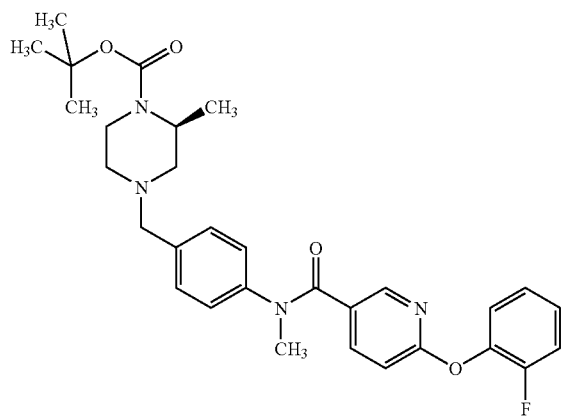

1,1-Dimethylethyl (2S)-4-({4-[[(6-chloro-3-pyridinyl)carbonyl](methyl)amino]phenyl}methyl)-2-methyl-1-piperazinecarboxylate (D54) (0.1 g, 0.218 mmol) and 2-fluorophenol (0.025 g, 0.436 mmol) were dissolved in DMF (5 mL). Potassium carbonate (0.06 g, 0.436 mmol) was added and the mixture was heated to 80° C. overnight then at 130° C. for 7 h. The mixture was left to stand at room temperature overnight and the solvent removed under vacuum. The residue was partitioned between EtOAc and water. The organic layer was dried and concentrated to produce a brown oil. The crude product was purified by MDAP to yield the formic acid salt. The salt was taken up in DCM and washed with sat. NaHCO$_3$. The DCM layer was dried and concentrated to yield the title compound as a colourless oil (0.038 g). $\delta_H$ (CDCl$_3$, 400 MHz) 8.02 (1H, d), 7.68 (1H, dd), 7.23 (2H, d), 7.15 (4H, m), 6.98 (2H, d), 6.78 (1H, d), 4.18 (1H, br.s), 3.80 (1H, d), 3.48 (3H, s), 3.46 (1H, d), 3.33 (1H, d), 3.08 (1H, td), 2.69 (1H, d), 2.51 (1H, d), 2.10 (1H, dd), 1.98 (1H, m), 1.46 (9H, s), 1.20 (3H, d). MS (ES): MH$^+$ 535.3.

Description 56

1,1-Dimethylethyl (2S)-4-({4-[({6-[(3-fluorophenyl)oxy]-3-pyridinyl}carbonyl)(methyl)amino]phenyl}methyl)-2-methyl-1-piperazinecarboxylate (D56)

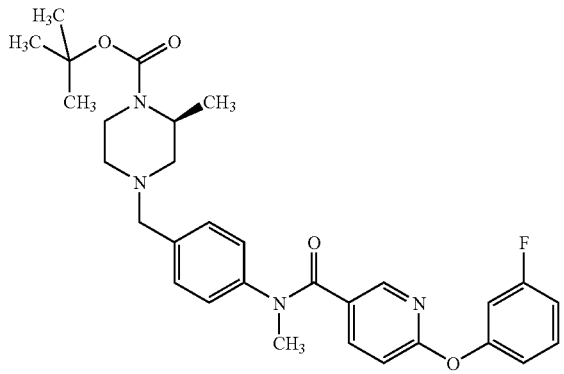

The title compound was prepared from 1,1-dimethylethyl (2S)-4-({4-[[(6-chloro-3-pyridinyl)carbonyl](methyl)amino]phenyl}methyl)-2-methyl-1-piperazinecarboxylate (D54) and 3-fluorophenol in a similar manner to that described for D55 in Description 55, yielding the title compound as a pale yellow oil (0.057 g). MS (ES): MH$^+$ 535.3.

Description 57

1,1-Dimethylethyl (2S)-4-({4-[({6-[(3-cyanophenyl)oxy]-3-pyridinyl}carbonyl)(methyl)amino]phenyl}methyl)-2-methyl-1-piperazinecarboxylate (D57)

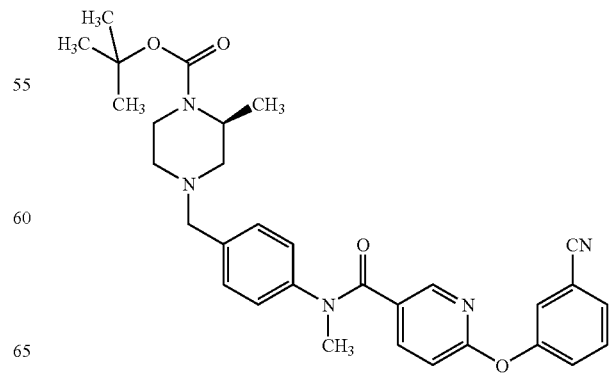

The title compound was prepared from 1,1-dimethylethyl (2S)-4-({4-[[(6-chloro-3-pyridinyl)carbonyl](methyl)amino]phenyl}methyl)-2-methyl-1-piperazinecarboxylate (D54) and 3-cyanophenol in a similar manner to that described for D55 in Description 55 although the reaction temp./time was 130° C. for 24 h and purification was carried out by column chromatography. This gave the title compound as a colourless oil (0.184 g). MS (ES): MH+ 542.3.

Description 58

1,1-Dimethylethyl (2S)-4-({4-[({6-[(4-fluorophenyl)amino]-3-pyridinyl}carbonyl)(methyl)amino]phenyl}methyl)-2-methyl-1-piperazinecarboxylate (D58)

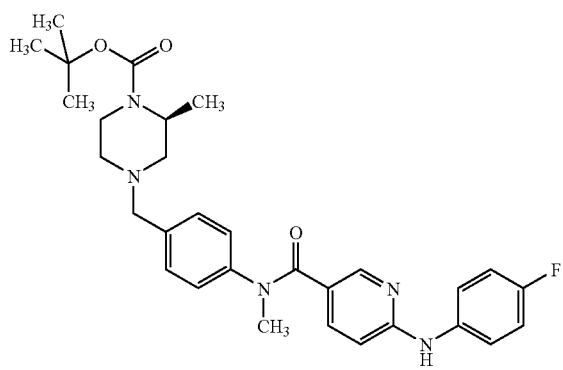

BINAP (0.041 g, 0.0654 mmol), cesium carbonate (0.213 g, 0.654 mmol) and palladium acetate (0.009 g, 0.0436 mmol) were combined in dioxane (1 mL) and sonicated for 1 h under an argon atmosphere. To the red mixture was added 4-fluoroaniline (0.053 g, 0.479 mmol) and 1,1-dimethylethyl (2S)-4-({4-[[(6-chloro-3-pyridinyl)carbonyl](methyl)amino]phenyl}methyl)-2-methyl-1-piperazinecarboxylate (D54) (0.2 g, 0.436 mmol). The mixture was stirred at 60° C. for 1 h, the solvent was removed under vacuum and the residues partitioned between EtOAc and water. The EtOAc layer was dried and concentrated. The crude product was purified by chromatography. Elution with a 0-70% EtOAc/petroleum ether gradient yielded the title compound as a pale yellow oil (0.110 g). $\delta_H$ (CDCl$_3$, 400 MHz) 8.10 (1H, m), 7.40 (1H, dd), 7.25 (3H, m), 7.02 (4H, m), 6.92 (1H, s), 6.43 (1H, d), 4.18 (1H, br.s), 3.80 (1H, d), 3.48 (3H, s), 3.48 (1H, d), 3.36 (1H, d), 3.10 (1H, td), 2.70 (1H, d), 2.52 (1H, d), 2.10 (1H, m), 1.98 (1H, m), 1.85 (1H, br.s), 1.45 (9H, s), 1.20 (3H, d). MS (ES): MH+ 534.3.

Description 59

1,1-Dimethylethyl (2S)-4-({4-[{[1-(4-fluorophenyl)-4-piperidinyl]carbonyl}(methyl)amino]phenyl}methyl)-2-methyl-1-piperazinecarboxylate (D59)

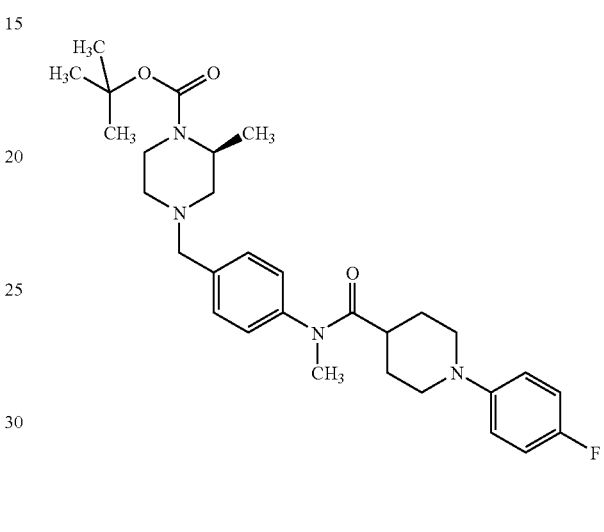

Step 1: 1-(4-Fluorophenyl)-4-piperidinecarboxylic acid (0.1 g, 0.45 mmol) was stirred in dioxane (5 mL) and thionyl chloride (0.165 mL, 2.25 mmol) was added drop-wise. After stirring for 1 h the solvent was removed by evaporation, DCM was added to the residue which was then re-concentrated to give 1-(4-fluorophenyl)-4-piperidinecarbonyl chloride which was used directly in step 2.

Step 2: The acid chloride from step 1 was taken up in DCM (2.5 mL) and added drop-wise to 1,1-dimethylethyl (2S)-2-methyl-4-{[4-(methylamino)phenyl]methyl}-1-piperazinecarboxylate (D3) (0.121 g, 0.38 mmol) in DCM (2.5 mL), followed by triethylamine (0.080 mL, 0.57 mmol). The reaction mixture was stirred for 3 h under argon, then the solvent was removed by evaporation. The residue was partitioned between DCM (30 mL) and water (30 mL). The aqueous was re-extracted with DCM (30 mL) and the combined organic layers were dried and concentrated to yield the title compound as a yellow oil. $\delta_H$ (CDCl$_3$, 400 MHz) 7.40 (2H, d), 7.15 (2H, d), 6.89 (2H, m), 6.80 (2H, m), 4.20 (1H, br.s), 3.82 (1H, d), 3.50 (4H, m), 3.27 (3H, s), 3.10 (1H, m), 2.76 (1H, d), 2.58 (1H, d), 2.35 (3H, m), 2.17 (1H, m), 2.00 (3H, m), 1.70 (2H, d), 1.46 (9H, s), 1.22 (3H, d). MS (ES): MH+ 525.4.

Description 60

1,1-Dimethylethyl (2S)-4-({4-[{[6-(3-fluorophenyl)-3-pyridinyl]carbonyl}(methyl)amino]phenyl}methyl)-2-methyl-1-piperazinecarboxylate (D60)

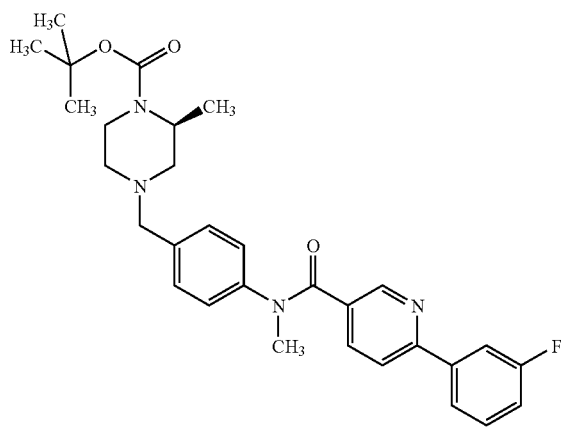

Step 1: 6-(3-Fluorophenyl)-3-pyridinecarboxylic acid (82 mg, 0.376 mmol) was stirred in dioxane (4 mL) and thionyl chloride (0.137 mL, 1.88 mmol) added dropwise. The reaction mixture was heated at reflux for 40 min then concentrated in vacuo to give 6-(3-fluorophenyl)-3-pyridinecarbonyl chloride as a white solid (0.088 g) which was used directly in step 2.

Step 2: The acid chloride from step 1 was taken up in DCM and added drop-wise to a mixture of 1,1-dimethylethyl (2S)-2-methyl-4-{[4-(methylamino)phenyl]methyl}-1-piperazinecarboxylate (D3) (0.1 g, 0.313 mmol) and triethylamine (0.065 mL, 0.47 mmol) in DCM (5 mL). The reaction mixture was stirred at room temperature under argon for ~15 h, then diluted with water and DCM. The organic layer was dried and concentrated to give the crude product, which was purified by column chromatography. Elution with EtOAc/petroleum ether yielded the title compound as a yellow oil (0.127 g). $\delta_H$ (CDCl$_3$, 400 MHz) 8.51 (1H, d), 7.75 (1H, dd), 7.67 (2H, m), 7.55 (1H, d), 7.40 (1H, m), 7.24 (2H, d), 7.08 (1H, m), 7.03 (2H, d), 4.15 (1H, br.s), 3.78 (1H, d), 3.53 (3H, s), 3.45 (1H, d), 3.32 (1H, d), 3.06 (1H, td), 2.69 (1H, d), 2.49 (1H, d), 2.09 (1H, dd), 1.98 (1H, m), 1.44 (9H, s), 1.16 (3H, d). MS (ES): MH$^+$ 519.3.

Description 61

1,1-Dimethylethyl (2S)-4-({4-[{[6-(4-fluorophenyl)-2-methyl-3-pyridinyl]carbonyl}(methyl)amino]phenyl}methyl)-2-methyl-1-piperazinecarboxylate (D61)

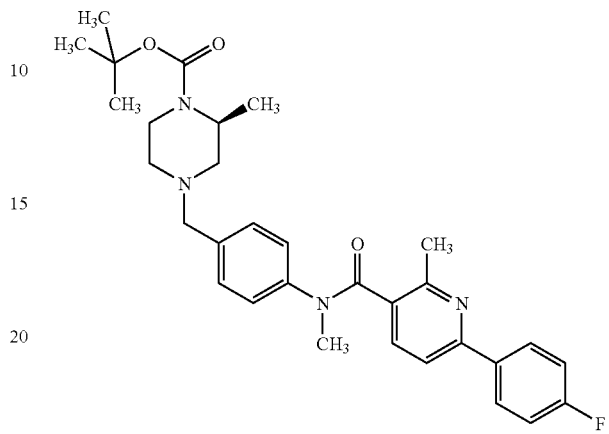

To 1-hydroxybenzotriazole (63.4 mg, 0.47 mmol) and N-benzyl-N'-cyclohexylcarbodiimide resin (351.6 mg, 1.6 mmol/g) in DMF (1 mL) was added 6-(4-fluorophenyl)-2-methyl-3-pyridinecarboxylic acid (72.3 mg, 0.313 mmol) in DMF (1 mL). The mixture was stirred for 30 minutes under an argon atmosphere and 1,1-dimethylethyl (2S)-2-methyl-4-{[4-(methylamino)phenyl]methyl}-1-piperazinecarboxylate (D3) (100 mg, 0.313 mmol) in DCM (2 mL) was added. The mixture was stirred overnight at room temperature. PS-trisamine resin (2 eq. relative to acid), PS-isocyanate resin (2 eq. relative to amine) and MP-carbonate resin (5 eq. relative to HOBt) were added and the mixture stirred overnight at room temperature. The mixture was filtered to remove the resins which were then washed with further DCM. The filtrate was concentrated to give the crude product which was purified by column chromatography. Elution with an ether/petroleum ether gradient yielded the title compound (35.2 mg). $\delta_H$ (CDCl$_3$, 400 MHz) 8.00 (2H, s), 7.37 (1H, d), 7.27 (1H, m), 7.12 (4H, m), 6.98 (2H, s), 4.14 (1H, bm), 3.75 (2H, d), 3.52 (3H, s), 3.40 (1H, d), 3.25 (1H, d), 3.03 (1h, t), 2.58 (4H, m), 2.41 (1H, d), 2.04 (1H, m), 1.95 (1H, m), 1.44 (9H, s), 1.13 (3H, d). MS (ES): MH$^+$ 533.3.

Description 62

1,1-Dimethylethyl(2S)-4-[(3-fluoro-4-nitrophenyl)methyl]-2-methyl-1-piperazinecarboxylate (D62)

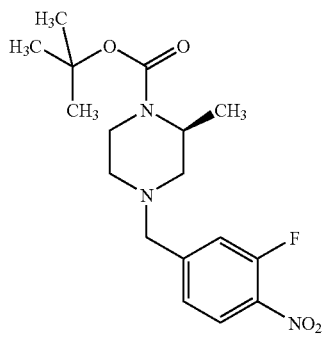

A solution of 4-(bromomethyl)-2-fluoro-1-nitrobenzene (232 mg, 1 mmol) and Hunig's base (0.192 mL, 1.1 mmol) in DMF (3 mL) was treated with 1,1-dimethylethyl (2S)-2-methyl-1-piperazinecarboxylate (200 mg, 1 mmol) in DMF (3 mL) and stirred at room temperature for 20 minutes. The reaction mixture was concentrated, re-dissolved in DCM and washed with water and brine, then dried and concentrated. The crude product was purified by column chromatography. Elution with EtOAc/pentane yielded the title compound as a colourless gum (327 mg). $\delta_H$ (CDCl$_3$, 400 MHz) 8.03 (1H, m), 7.34 (1H, dd), 7.27 (1H, m), 4.22 (1H, br.s), 3.84 (1H, d), 3.58 (1H, d), 3.47 (1H, d), 3.13 (1H, td), 2.72 (1H, m), 2.54 (1H, m), 2.22 (1H, dd), 2.09 (1H, m), 1.46 (9H, s), 1.26 (3H, d) [δvalues corrected for incorrectly referenced TMS at 0.62 ppm on spectrum].

Description 63

1,1-Dimethylethyl (2S)-4-[(4-amino-3-fluorophenyl)methyl]-2-methyl-1-piperazinecarboxylate (D63)

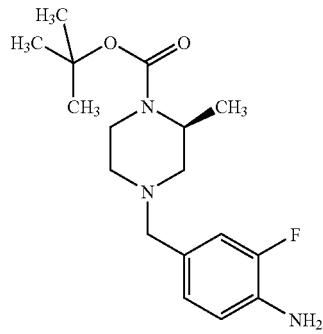

The title compound was prepared from 1,1-dimethylethyl (2S)-4-[(3-fluoro-4-nitrophenyl)methyl]-2-methyl-1-piperazinecarboxylate (D62) using a method similar to that described for D2 in Description 2 although the reaction was carried out on an H-Cube™ continuous flow hydrogenator and triethylamine was used in place of solid KOH. $\delta_H$ (CDCl$_3$, 400 MHz) 6.99 (1H, dd), 6.86 (1H, dd), 6.71 (1H, dd), 4.17 (1H, br.s), 3.79 (1H, d), 3.67 (2H, br.s), 3.40 (1H, d), 3.27 (1H, d), 3.09 (1H, td), 2.73 (1H, m), 2.56 (1H, m), 2.08 (1H, dd), 1.96 (1H, m), 1.45 (9H, s), 1.22 (3H, d).

Description 64

1,1-Dimethylethyl (2S)-4-{[3-fluoro-4-(methylamino)phenyl]methyl}-2-methyl-1-piperazinecarboxylate (D64)

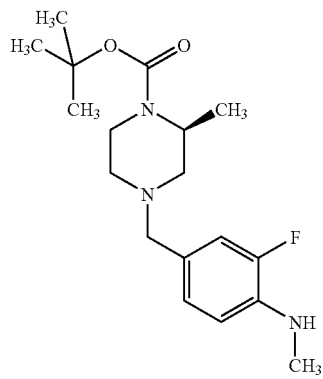

The title compound was prepared from 1,1-dimethylethyl (2S)-4-[(4-amino-3-fluorophenyl)methyl]-2-methyl-1-piperazinecarboxylate (D63) using a method similar to that described for D3 in Description 3A although the reaction was heated at 50° C. overnight prior to and after addition of sodium borohydride. $\delta_H$ (CDCl$_3$, 400 MHz) 6.96 (2H, m), 6.61 (1H, m), 4.17 (1H, br.s), 3.89 (1H, br.s), 3.79 (1H, d), 3.41 (1H, d), 3.28 (1H, d), 3.08 (1H, td), 2.87 (3H, s), 2.74 (1H, m), 2.57 (1H, m), 2.08 (1H, dd), 1.95 (1H, m), 1.45 (9H, s), 1.22 (3H, d).

Description 65

1,1-Dimethylethyl (2S)-4-[(2-fluoro-4-nitrophenyl)methyl]-2-methyl-1-piperazinecarboxylate (D65)

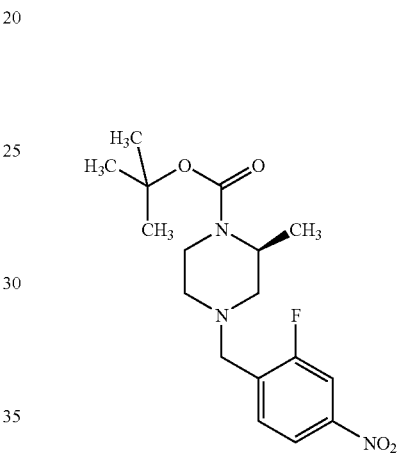

Step 1: A mixture of 2-fluoro-4-nitrotoluene (1.55 g, 10 mmol), N-bromosuccinimide (1.96 g, 11 mmol) and benzoyl peroxide (0.121 g, 0.5 mmol) in CCl$_4$ (60 mL) was irradiated with a 500 W lamp overnight. The reaction mixture was filtered, concentrated and eluted through a silica column with EtOAc/pentane to give a crude product mixture (2.34 g) which was used in step 2.

Step 2: A mixture of crude 4-(bromomethyl)-3-fluoro-1-nitrobenzene (2.11 g) from step 1, Hunig's base (1.9 mL, 10.913 mmol) and 1,1-dimethylethyl (2S)-2-methyl-1-piperazinecarboxylate (2 g, 10 mmol) in DMF (15 mL) was stirred at room temperature for 40 minutes. The reaction mixture was concentrated, re-dissolved in DCM and washed with water (×2) and brine, then dried and concentrated. The crude product was purified by column chromatography. Elution with EtOAc/pentane yielded the title compound as a yellow gum which crystallised on standing (2.11 g). $\delta_H$ (CDCl$_3$, 400 MHz) 8.03 (1H, dd), 7.91 (1H, dd), 7.70 (1H, m), 4.22 (1H, br.s), 3.84 (1H, d), 3.61 (2H, m), 3.12 (1H, td), 2.74 (1H, m), 2.57 (1H, m), 2.27 (1H, dd), 2.11 (1H, m), 1.46 (9H, s), 1.25 (3H, d). MS (ES): MH$^+$ 354.1.

Description 66

1,1-Dimethylethyl (2S)-4-[(4-amino-2-fluorophenyl)methyl]-2-methyl-1-piperazinecarboxylate (D66)

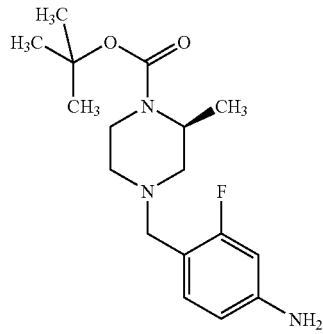

1,1-Dimethylethyl (2S)-4-[(2-fluoro-4-nitrophenyl)methyl]-2-methyl-1-piperazinecarboxylate (D65) (2.05 g, 5.801 mmol) was taken up in methanol (50 mL) and wet (50% w/w water) 5% platinum on carbon (2 g) and triethylamine (8 mL, 58.01 mmol) were added. The mixture was hydrogenated at atmospheric pressure and room temperature for 2.5-3 h. The mixture was filtered and the filtrate concentrated to give the crude product which was purified by column chromatography. Elution with EtOAc/pentane yielded the title compound as an almost colourless gum (1.15 g). $\delta_H$ (CDCl$_3$, 400 MHz) 7.11 (1H, t), 6.42 (1H, dd), 6.35 (1H, dd), 4.17 (1H, br.s), 3.79 (1H, d), 3.72 (2H, s), 3.43 (2H, m), 3.07 (1H, td), 2.74 (1H, m), 2.58 (1H, d), 2.14 (1H, dd), 1.99 (1H, m), 1.45 (9H, s), 1.20 (3H, d).

Description 67

1,1-Dimethylethyl (2S)-4-{[2-fluoro-4-(methylamino)phenyl]methyl}-2-methyl-1-piperazinecarboxylate (D67)

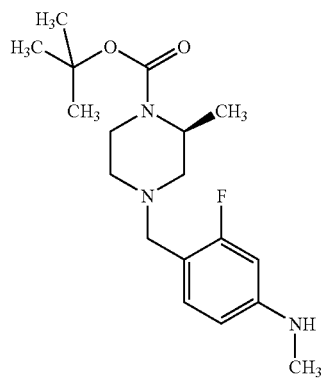

The title compound was prepared from 1,1-dimethylethyl (2S)-4-[(4-amino-2-fluorophenyl)methyl]-2-methyl-1-piperazinecarboxylate (D66) using a method similar to that described for D3 in Description 3A although the reaction was heated at 50° C. overnight prior to addition of sodium borohydride and for 24 h after addition. $\delta_H$ (CDCl$_3$, 400 MHz) 7.11 (1H, t), 6.35 (1H, dd), 6.27 (1H, dd), 4.17 (1H, br.s), 3.78 (2H, m), 3.44 (2H, m), 3.07 (1H, td), 2.82 (3H, s), 2.75 (1H, m), 2.59 (1H, m), 2.14 (1H, dd), 1.99 (1H, m), 1.44 (9H, s), 1.21 (3H, d).

Description 68

1,1-Dimethylethyl (2S)-4-({4-[[(6-chloro-3-pyridinyl)carbonyl](methyl)amino]-3-fluorophenyl}methyl)-2-methyl-1-piperazinecarboxylate (D68)

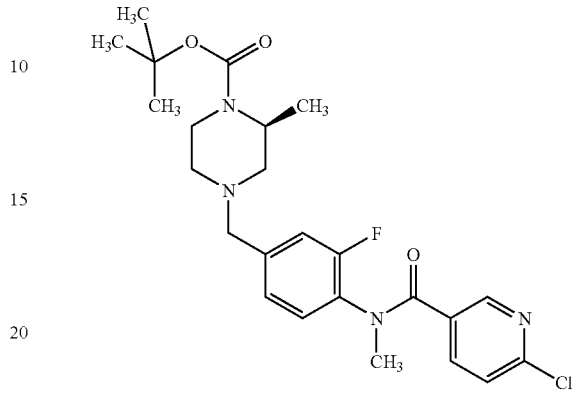

The title compound was prepared from 1,1-dimethylethyl (2S)-4-{[2-fluoro-4-(methylamino)phenyl]methyl}-2-methyl-1-piperazinecarboxylate (D64) using a method similar to that described for D54 in Description 54 although no aqueous work-up was carried out. The reaction mixture was concentrated and used directly in the next step. MS (ES): MH$^+$ 477.11.

Description 69

1,1-Dimethylethyl(2S)-4-({3-fluoro-4-[({6-[(4-fluorophenyl)oxy]-3-pyridinyl}carbonyl)(methyl)amino]phenyl}methyl)-2-methyl-1-piperazinecarboxylate (D69)

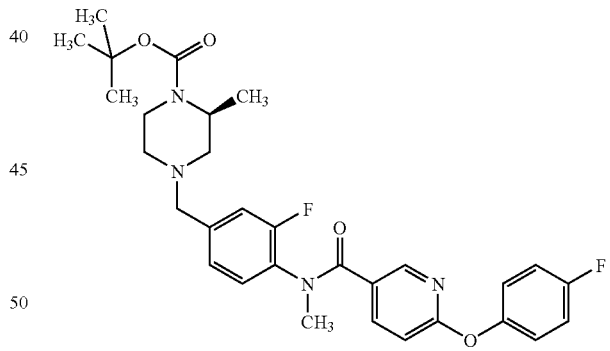

The title compound was prepared from 1,1-dimethylethyl (2S)-4-({4-[[(6-chloro-3-pyridinyl)carbonyl](methyl)amino]-3-fluorophenyl}methyl)-2-methyl-1-piperazinecarboxylate (D68) and 4-fluorophenol using a method similar to that described for D55 in Description 55 although only 1 eq of 4-fluorophenol was added initially, the reaction was heated at 130° C. over-weekend, further 4-fluorophenol (2 eq) and potassium carbonate (4 eq) were added and the reaction was heated at 130° C. overnight. The product was purified by column chromatography. $\delta_H$ (CDCl$_3$, 400 MHz) 8.07 (1H, s), 7.73 (1H, dd), 7.04 (7H, m), 6.74 (1H, d), 4.19 (1H, br.s), 3.80 (1H, d), 3.43 (4H, m), 3.33 (1H, d), 3.08 (1H, td), 2.67 (1H, d), 2.49 (1H, d), 2.13 (1H, dd), 2.00 (1H, m), 1.45 (9H, s), 1.21 (3H, d).

Description 70

1,1-Dimethylethyl (2S)-4-({4-[[(6-chloro-3-pyridinyl)carbonyl](methyl)amino]-2-fluorophenyl}methyl)-2-methyl-1-piperazinecarboxylate (D70)

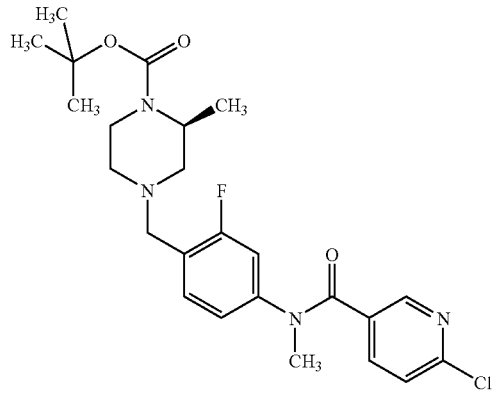

The title compound was prepared from 1,1-dimethylethyl (2S)-4-{[2-fluoro-4-(methylamino)phenyl]methyl}-2-methyl-1-piperazinecarboxylate (D67) using a method similar to that described for D54 in Description 54 although no aqueous work-up was carried out. The reaction mixture was concentrated and used directly in the next step. MS (ES): MH+ 477.1.

Description 71

1,1-Dimethylethyl(2S)-4-({2-fluoro-4-[({6-[(4-fluorophenyl)oxy]-3-pyridinyl}carbonyl)(methyl)amino]phenyl}methyl)-2-methyl-1-piperazinecarboxylate (D71)

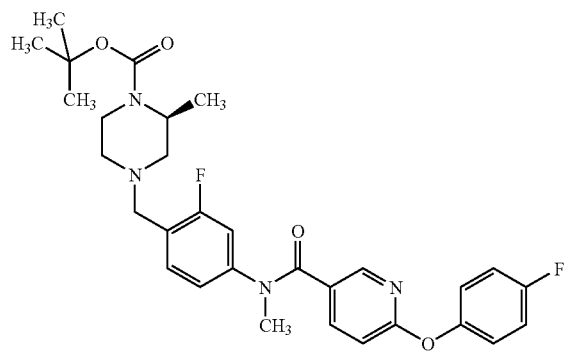

The title compound was prepared from 1,1-dimethylethyl (2S)-4-({4-[[(6-chloro-3-pyridinyl)carbonyl](methyl)amino]-2-fluorophenyl}methyl)-2-methyl-1-piperazinecarboxylate (D70) and 4-fluorophenol using a method similar to that described for D55 in Description 55 although the reaction temp./time was 130° C. for 8 h and purification was carried out by column chromatography. $\delta_H$ (CDCl$_3$, 400 MHz) 8.07 (1H, dd), 7.70 (1H, dd), 7.33 (1H, t), 7.05 (4H, m), 6.78 (3H, m), 4.19 (1H, br.s), 3.81 (1H, d), 3.47 (5H, m), 3.07 (1H, td), 2.71 (1H, d), 2.53 (1H, d), 2.18 (1H, dd), 2.04 (1H, m), 1.46 (9H, s), 1.20 (3H, d).

Description 72

1,1-Dimethylethyl (2S)-4-({4-[[(5-bromo-2-pyridinyl)carbonyl](methyl)amino]phenyl}methyl)-2-methyl-1-piperazinecarboxylate (D72)

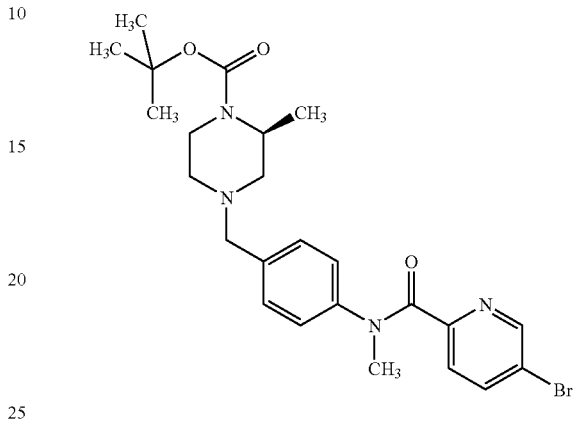

Step 1: 5-Bromo-2-pyridinecarbonitrile (1 g, 5.464 mmol) was dissolved in EtOH (20 mL) and water (20 mL) and treated with potassium hydroxide (1.53 g, 27.32 mmol). The reaction mixture was heated to 80° C. for 24 h. The solvent was removed under vacuum and the residue was taken up in water and acidified to pH 4 with 2M HCl. The aqueous layer was extracted with ethyl acetate (×3) and the combined organic layers dried and concentrated to give 5-bromo-2-pyridinecarboxylic acid (0.704 g) as an orange solid which was used in step 2.

Step 2: The acid from step 1 (0.702 g, 3.475 mmol) was suspended in DCM (40 mL) under argon, DMF (1 drop) was added and the mixture was cooled in an ice-bath. Oxalyl chloride was added portion-wise over 5 minutes and the mixture was then heated to 40° C. for 90 minutes. On cooling, the solvent was removed to produce 5-bromo-2-pyridinecarbonyl chloride (0.801 g) as a brown solid which was used in step 3.

Step 3: The acid chloride from step 2 (0.801 g, 3.633 mmol) in DCM (10 mL) was added to a solution of 1,1-dimethylethyl (2S)-2-methyl-4-{[4-(methylamino)phenyl]methyl}-1-piperazinecarboxylate (D3) (0.928 g, 2.906 mmol) in DCM (20 mL). Triethylamine (1.009 mL, 7.266 mmol) was added and the mixture was stirred at room temperature overnight. The reaction mixture was diluted with DCM and washed with water. The aqueous layer was re-extracted with DCM (×2) and the combined organics were dried and concentrated to give the crude product which was purified by column chromatography. Elution with a 0-50% ethyl acetate/petroleum ether gradient yielded the title compound as a yellow oil (1.432 g). $\delta_H$ (CDCl$_3$, 400 MHz) 8.34 (1H, br.s), 7.72 (1H, br.d), 7.38 (1H, br.d), 7.18 (2H, br.m), 6.98 (2H, br.s), 4.17 (1H, br.s), 3.79 (1H, d), 3.51 (3H, s), 3.46 (1H, d), 3.32 (1H, d), 3.07 (1H, td), 2.68 (1H, d), 2.47 (1H, d), 2.10 (1H, dd), 1.98 (1H, m), 1.45 (9H, s), 1.19 (3H, d). MS (ES): MH+ 503/505.

Description 73

1,1-Dimethylethyl (2S)-4-({4-[({5-[(4-fluorophenyl)oxy]-2-pyridinyl}carbonyl)(methyl)amino]phenyl}methyl)-2-methyl-1-piperazinecarboxylate (D73)

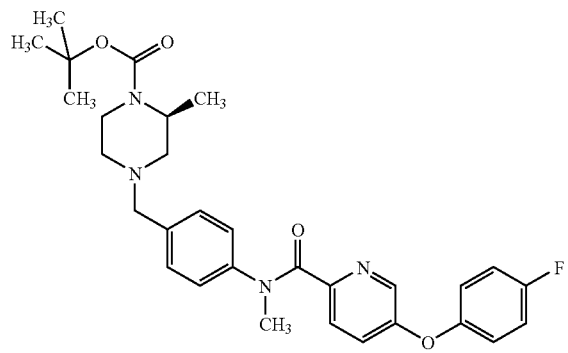

1,1-Dimethylethyl (2S)-4-({4-[[(5-bromo-2-pyridinyl)carbonyl](methyl)amino]phenyl}methyl)-2-methyl-1-piperazinecarboxylate (D72) (0.2 g, 0.397 mmol), 4-fluorophenol (0.089 g, 0.794 mmol), cesium carbonate (0.259 g, 0.794 mmol) and 2,2,6,6-tetramethyl-3,5-heptanedione (TMHD) (0.008 g, 0.040 mmol) were combined in NMP (3 mL) under argon. Copper (I) chloride (0.02 g, 0.199 mmol) was added and the mixture heated at 120° C. overnight. A second portion of 4-fluorophenol, copper (I) chloride, cesium carbonate and TMHD was added and heating continued at 120° C. overnight. After cooling to room temperature, the mixture was partially concentrated, the residue was taken up in EtOAc and washed with saturated aqueous NaHCO$_3$ and water. The organic layer was dried and concentrated to give the crude product which was purified by column chromatography. Elution with 0-50% ethyl acetate/petroleum ether yielded the title compound as a yellow oil (0.161 g). $\delta_H$ (CDCl$_3$, 400 MHz) 8.04 (1H, br.s), 7.49 (1H, br.d), 7.20 (2H, d), 7.00 (7H, m), 4.17 (1H, br.s), 3.79 (1H, d), 3.51 (3H, s), 3.47 (1H, d), 3.33 (1H, d), 3.08 (1H, td), 2.69 (1H, d), 2.51 (1H, d), 2.10 (1H, dd), 1.99 (1H, m), 1.46 (9H, s), 1.19 (3H, d). MS (ES): MH$^+$ 535.4.

Description 74

1,1-Dimethylethyl (2S)-4-({4-[({5-[(3-fluorophenyl)oxy]-2-pyridinyl}carbonyl)(methyl)amino]phenyl}methyl)-2-methyl-1-piperazinecarboxylate (D74)

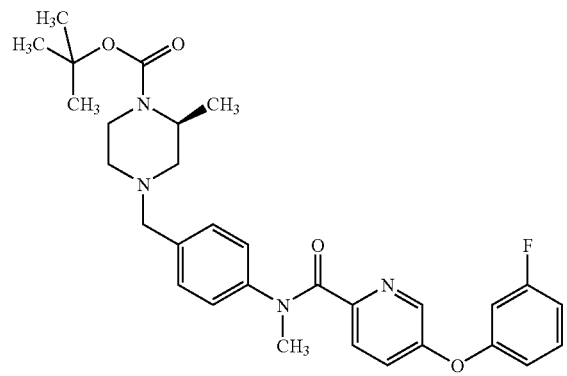

The title compound was prepared from 1,1-dimethylethyl (2S)-4-({4-[[(5-bromo-2-pyridinyl)carbonyl](methyl)amino]phenyl}methyl)-2-methyl-1-piperazinecarboxylate (D72) and 3-fluorophenol using a method similar to that described for D73 in Description 73 although 1 eq. CuCl and 0.25 eq. THMD were used. MS (ES): MH$^+$ 535.3.

Description 75

1,1-Dimethylethyl (2S)-4-({4-[({5-[(3-cyanophenyl)oxy]-2-pyridinyl}carbonyl)(methyl)amino]phenyl}methyl)-2-methyl-1-piperazinecarboxylate (D75)

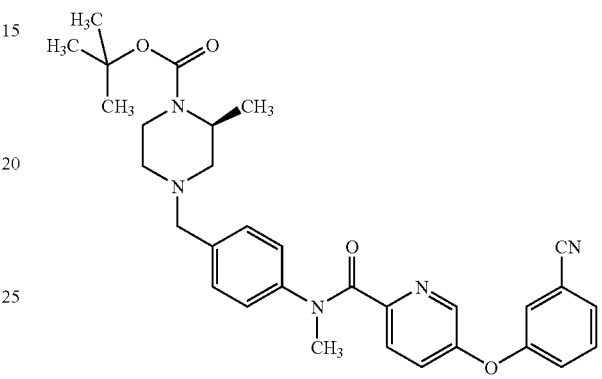

The title compound was prepared from 1,1-dimethylethyl (2S)-4-({4-[[(5-bromo-2-pyridinyl)carbonyl](methyl)amino]phenyl}methyl)-2-methyl-1-piperazinecarboxylate (D72) and 3-cyanophenol using a method similar to that described for D73 in Description 73 although the reaction was worked up after the first night of heating. MS (ES): MH$^+$ 542.3.

Description 76

1,1-Dimethylethyl (2S)-4-({4-[({5-[(4-fluorophenyl)amino]-2-pyridinyl}carbonyl)(methyl)amino]phenyl}methyl)-2-methyl-1-piperazinecarboxylate (D76)

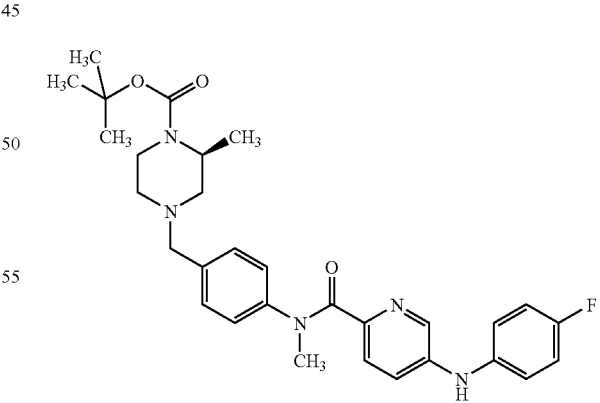

The title compound was prepared 1,1-dimethylethyl (2S)-4-({4-[[(5-bromo-2-pyridinyl)carbonyl](methyl)amino]phenyl}methyl)-2-methyl-1-piperazinecarboxylate (D72) and 4-fluoroaniline using a method similar to that described for D58 in Description 58 although the reaction time was 18 h. MS (ES): MH$^+$ 534.2.

Description 77

N-[4-(Hydroxymethyl)-3-methylphenyl]acetamide (D77)

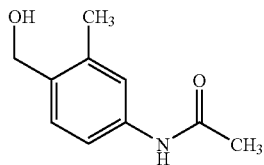

4-(Acetylamino)-2-methylbenzoic acid (2 g, 10.4 mmol) was suspended in THF (50 mL) and borane-THF complex (1M in THF, 26 mL, 26 mmol) added drop-wise over ~15 minutes. The reaction mixture was stirred under argon at room temperature overnight then quenched with water (52 mL) and extracted with ethyl acetate (×3). The combined organics were dried and concentrated to give the crude product which was purified by column chromatography. Elution with 0-100% ethyl acetate/petroleum ether yielded the title compound as a cream solid (0.379 g). $\delta_H$ (MeOD, 400 MHz) 7.36 (2H, m), 7.25 (1H, d), 4.57 (2H, s), 2.31 (3H, s), 2.10 (3H, s). MS (ES): MH$^+$ 180.2.

Description 78

N-(4-Formyl-3-methylphenyl)acetamide (D78)

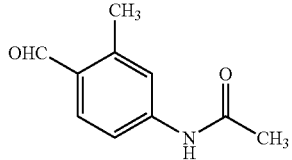

N-[4-(Hydroxymethyl)-3-methylphenyl]acetamide (D77) (0.36 g, 2 mmol) and manganese dioxide (0.875 g, 10 mmol) were combined in acetonitrile (16 mL) and heated to 120° C. in the microwave for 7 minutes. The MnO$_2$ was filtered off and the reaction mixture was concentrated to give the crude product which was purified by column chromatography. Elution with 0-100% ethyl acetate/petroleum ether yielded the title compound as a cream solid (0.326 g). $\delta_H$ (CDCl$_3$, 400 MHz) 10.17 (1H, s), 7.77 (1H, d), 7.51 (1H, d), 7.45 (1H, s), 7.36 (1H, br.s), 2.66 (3H, s), 2.22 (3H, s). MS (ES): MH$^+$ 178.2.

Description 79

1,1-Dimethylethyl (2S)-4-{[4-(acetylamino)-2-methylphenyl]methyl}-2-methyl-1-piperazinecarboxylate (D79)

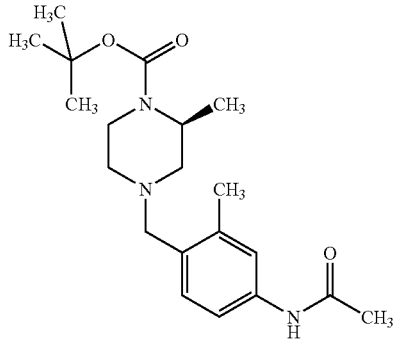

N-(4-Formyl-3-methylphenyl)acetamide (D78) (326 mg, 1.8 mmol), 1,1-dimethylethyl (2S)-2-methyl-1-piperazinecarboxylate hydrochloride (436 mg, 1.8 mmol), triethylamine (0.282 mL, 2 mmol) and sodium tri(acetoxy)borohydride (781 mg, 3.7 mmol) were stirred together in DCE (15 mL) for 17 h. Saturated aqueous NaHCO$_3$ (15 mL) was added and the reaction mixture stirred for 1 h. The organic layer was separated and washed with water and brine, then dried and concentrated to give the crude product which was purified by chromatography. Elution with 0-100% ethyl acetate/petroleum ether yielded the title compound as a colourless oil (573 mg). $\delta_H$ (CDCl$_3$, 400 MHz) 7.27 (2H, m), 7.16 (1H, d), 7.11 (1H, br.s), 4.17 (1H, m), 3.78 (1H, m), 3.36 (2H, s), 3.02 (1H, m), 2.70 (1H, m), 2.56 (1H, m), 2.36 (3H, s), 2.17 (4H, m), 1.95 (1H, m), 1.45 (9H, s), 1.18 (3H, d). MS (ES): MH$^+$ 362.3.

Description 80

1,1-Dimethylethyl (2S)-4-[(4-amino-2-methyl phenyl)methyl]-2-methyl-1-piperazinecarboxylate (D80)

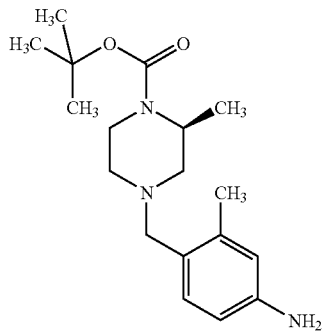

1,1-Dimethylethyl (2S)-4-{[4-(acetylamino)-2-methylphenyl]methyl}-2-methyl-1-piperazinecarboxylate (D79) (497 mg, 1.4 mmol) in KOH (1M aq soln., 5 mL) and methanol (5 mL) was heated to 140° C. for 1 h in a microwave reactor. The reaction mixture was diluted with methanol (5 mL) and heated for a total of 4 h 55 minutes at 130° C. in the microwave. The reaction mixture was concentrated to remove the methanol and partitioned between DCM and water. The organic layer was dried and concentrated to give the crude product which was purified by chromatography. Elution with 0-100% diethyl ether/petroleum ether followed by a column flush with 10% (2M NH$_3$ in methanol) in DCM yielded the title compound as a yellow oil (223 mg). $\delta_H$ (CDCl$_3$, 400 MHz) 6.97 (1H, d), 6.52 (1H, d), 6.46 (1H, dd), 4.17 (1H, br.s), 3.76 (1H, d), 3.57 (2H, br.s), 3.29 (2H, m), 3.01 (1H, td), 2.70 (1H, d), 2.56 (1H, d), 2.30 (3H, s), 2.10 (1H, dd), 1.90 (1H, m), 1.45 (9H, s), 1.18 (3H, d). MS (AP$^+$): MNa$^+$ 342.3 (MNa$^+$), no molecular ion (MH$^+$) observed.

Description 81

1,1-Dimethylethyl (2S)-2-methyl-4-{[2-methyl-4-(methylamino)phenyl]methyl}-1-piperazinecarboxylate (D81)

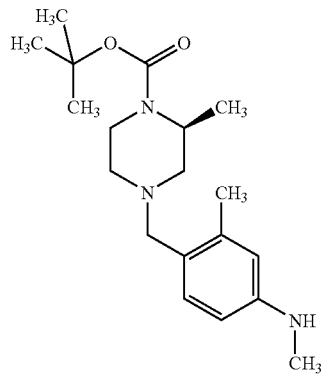

The title compound was prepared from 1,1-dimethylethyl (2S)-4-[(4-amino-2-methylphenyl)methyl]-2-methyl-1-piperazinecarboxylate (D80) using a method similar to that described for D3 in Description 3A although the reaction was heated at 50° C. for 16 h prior to addition of sodium borohydride and 5.5 h after addition. $\delta_H$ (CDCl$_3$, 400 MHz) 7.00 (1H, d), 6.45 (1H, d), 6.39 (1H, dd), 4.17 (1H, br.s), 3.76 (1H, d), 3.57 (1H, br.s), 3.33 (1H, d), 3.27 (1H, d), 3.01 (1H, td), 2.82 (3H, s), 2.71 (1H, d), 2.58 (1H, d), 2.32 (3H, s), 2.11 (1H, dd), 1.90 (1H, m), 1.45 (9H, s), 1.17 (3H, d). MS (AP$^+$): 356.2 (MNa$^+$), 234.2, no molecular ion (MH$^+$) observed.

Description 81: Alternative Method (A)

1,1-Dimethylethyl (2S)-4-{[2-methyl-4-(methylamino)phenyl]methyl}-2-methyl-1-piperazinecarboxylate (D81)

To a mixture of 2-methyl-4-(methylamino)benzaldehyde (D93) (0.397 g) and 1,1-dimethylethyl (2S)-2-methyl-1-piperazinecarboxylate (0.533 g, 2.66 mmol) in 1,2-DCE (35 mL) was added sodium tri(acetoxy)borohydride (0.847 g, 4.00 mmol) and the reaction stirred at room temperature overnight. Saturated aqueous NaHCO$_3$ (30 mL) was added and the mixture was stirred for 4 h. The reaction mixture was extracted with DCM and the organics were dried and concentrated to give the crude product which was purified by column chromatography. Elution with ether/petroleum ether gave the title compound as a colourless oil (0.328 g).

Description 82

(3R,5S)-1-[(4-Nitrophenyl)methyl]-3,5-dimethylpiperazine (D82)

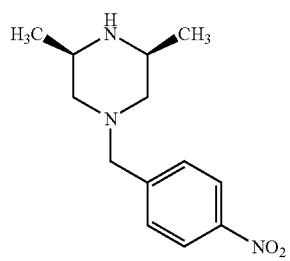

The title compound was prepared from 4-nitrobenzaldehyde and (2R,6S)-2,6-dimethylpiperazine using a method similar to that described for D1 in Description 1A. MS (ES): MH$^+$ 250.2

Description 83

1,1-Dimethylethyl methylcarbamate (D83)

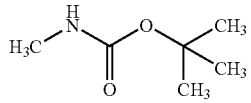

To a solution of Boc anhydride (7.5 g, 34.36 mmol) in DCM (40 mL) was added methylamine (173 mL, 2M solution in THF, 345 mmol) and the reaction mixture was stirred at room temperature overnight. The solvent and excess methylamine were removed in vacuo and dilute 2M HCl (10 mL) was added. The aqueous layer was extracted with DCM (×2) and the combined organics were dried and concentrated to give the title compound as a yellow oil (3.791 g). $\delta_H$ (CDCl$_3$, 400 MHz) 4.58 (1H, br.s), 2.73 (3H, d), 1.44 (9H, s).

Description 84

1,1-Dimethylethyl (6-formyl-3-pyridinyl)methylcarbamate (D84)

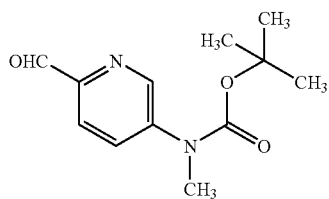

A mixture of 5-bromo-2-pyridinecarbaldehyde (1.5 g, 8.064 mmol), 1,1-dimethylethyl methylcarbamate (D83) (1.267 g, 9.677 mmol), tris(dibenzylideneacetone) dipalladium(0) (0.148 g, 0.161 mmol), xantphos (0.373 g, 0.645 mmol) and cesium carbonate (3.678 g, 11.289 mmol) in dioxane (35 mL) was heated at 110° C. overnight under an argon atmosphere. On cooling, the solvent was removed in vacuo and the residue partitioned between EtOAc and water. The organic layer was separated, washed with water and brine, dried and concentrated to give the crude product which was purified by column chromatography. Elution with 0-50% ether/petroleum ether gave the title compound as a brown oil (0.977 g). $\delta_H$ (CDCl$_3$, 400 MHz) 10.01 (1H, s), 8.79 (1H, d), 7.94 (1H, dd), 7.86 (1H, dd), 3.40 (3H, s), 1.53 (9H, s). MS (ES$^+$): 259.1 (MNa$^+$), 181.2, no molecular ion (MH$^+$) observed.

Description 85

5-(Methylamino)-2-pyridinecarbaldehyde and 6-[bis(methyloxy)methyl]-N-methyl-3-pyridinamine (D85)

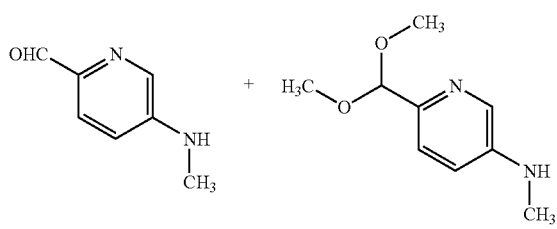

To a solution of 1,1-dimethylethyl (6-formyl-3-pyridinyl)methylcarbamate (D84) (0.977 g, 4.139 mmol) in DCM (80 mL) was added TFA (20 mL) and the reaction mixture was stirred at room temperature for 2 h. The solvent was removed in vacuo and the residue was taken up in methanol and eluted through an SCX (10 g) column with methanol then 2M $NH_3$ in methanol solution. The ammoniacal fraction was concentrated to give a yellow oil (0.622 g) which was an approximately 1:1 mixture of the title compounds. This material was used directly in the next step. MS ($ES^+$): aldehyde—137 ($MH^+$); acetal—151. MS ($AP^+$): aldehyde—137 ($MH^+$); acetal—205 ($MNa^+$), 151.

Description 86

1,1-Dimethylethyl (2S)-2-methyl-4-{[5-(methylamino)-2-pyridinyl]methyl}-1-piperazinecarboxylate (D86)

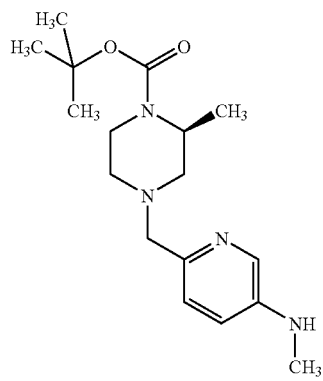

A mixture of 5-(methylamino)-2-pyridinecarbaldehyde and 6-[bis(methyloxy)methyl]-N-methyl-3-pyridinamine (D85) (0.622 g), 1,1-dimethylethyl (2S)-2-methyl-1-piperazinecarboxylate (0.910 g, 4.552 mmol) and triethylamine (0.418 g, 4.139 mmol) in 1,2-DCE (40 mL) was stirred at room temperature overnight. Sodium tri(acetoxy)borohydride (1.14 g, 5.38 mmol) was added and the reaction stirred at room temperature overnight. The reaction mixture was diluted with DCM and washed with saturated aq. $NaHCO_3$ solution and water. The organic layer was dried and concentrated to give the crude product which was purified by column chromatography. Elution with 0-100% EtOAc/petroleum ether gave the title compound as a yellow/brown oil (0.542 g). $\delta_H$ ($CDCl_3$, 400 MHz) 7.96 (1H, d), 7.23 (1H, d), 6.88 (1H, dd), 4.17 (1H, br.s), 3.80 (2H, d), 3.58 (1H, d), 3.45 (1H, d), 3.12 (1H, td), 2.86 (3H, s), 2.76 (1H, m), 2.58 (1H, m), 2.18 (1H, dd), 2.07 (1H, m), 1.45 (9H, s), 1.23 (3H, d). MS (ES): $MH^-$ 321.4

Description 87

1,1-Dimethylethyl (2S)-2-methyl-4-({4-[(1-methylethyl)amino]phenyl}methyl)-1-piperazinecarboxylate (D87)

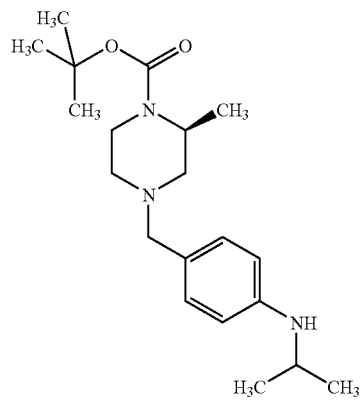

To a stirred solution of 1,1-dimethylethyl (2S)-4-[(4-aminophenyl)methyl]-2-methyl-1-piperazinecarboxylate (D2) (0.30 g, 1 mmol) in dry 1,2 DCE (5 mL) was added sequentially 2-methoxypropene (0.141 mL, 1.5 mmol), acetic acid (0.056 mL, 1 mmol) and sodium triacetoxyborohydride (0.313 g, 1.5 mmol). Further 1,2 DCE (5 mL) was added and the reaction mixture was stirred under argon at room temperature for 16 hours. Saturated $NaHCO_3$ (15 mL) was added and reaction mixture stirred for a further 1 hour. The aqueous layer was then extracted with DCM (×3) and the combined organic layers were dried ($Na_2SO_4$) and concentrated in vacuo. The crude material was purified by column chromatography eluting with 0-100% ether/petroleum ether to give the title compound (0.265 g). $\delta_H$ ($CDCl_3$, 400 MHz) 7.09 (2H, d), 6.54 (2H, d), 4.16 (1H, br.s), 3.78 (1H, d), 3.61 (1H, sp), 3.49 (1H, s), 3.42 (2H, m), 3.28 (1H, d), 3.08 (1H, td), 2.75 (1H, d), 2.59 (1H, d), 1.95 (1H, dd), 1.94 (1H, m), 1.45 (9H, s), 1.20 (9H, m). MS ($AP^+$): 370.3 ($MNa^+$), 248.3, no molecular ion ($MH^+$) observed.

Description 88

1,1-Dimethylethyl(2S)-4-{[4-(ethylamino)phenyl]methyl}-2-methyl-1-piperazinecarboxylate (D88)

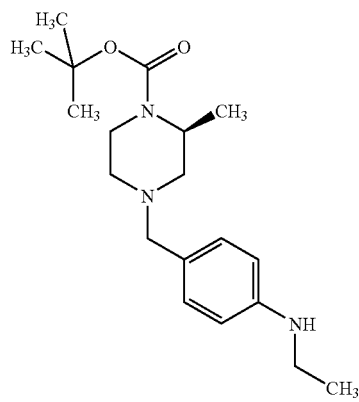

1,1-dimethylethyl (2S)-4-[(4-aminophenyl)methyl]-2-methyl-1-piperazinecarboxylate (D2) (0.30 g, 1 mmol), acetaldehyde (0.055 mL, 1 mmol), sodium triacetoxyborohydride (0.417 g, 2 mmol) and triethylamine (0.151 mL, 1.1 mmol) were combined in dry 1,2-DCE (15 mL) and stirred under Ar at room temperature for 48 hours. Saturated NaHCO₃ (15 mL) was added and reaction mixture stirred for a further 2 hours. The aqueous layer was then extracted with DCM (×3) and the combined organic layers were dried (Na₂SO₄) and concentrated in vacuo. The crude material was purified by column chromatography eluting with 0-100% ether/petroleum ether to give the title compound (0.239 g). $\delta_H$ (CDCl₃, 400 MHz) 7.11 (2H, d), 6.56 (2H, dd), 4.16 (1H, br.s), 3.78 (1H, d), 3.51 (1H, br.s), 3.42 (1H, d), 3.29 (1H, d), 3.15 (2H, q), 3.08 (1H, td), 2.75 (1H, d), 2.59 (1H, d), 2.06 (1H, dd), 1.93 (1H, m), 1.45 (9H, s), 1.25 (3H, t), 1.21 (3H, d). MS (ES⁺): 234.2, no molecular ion (MH⁺) observed.

Description 89

(Methyloxy)acetaldehyde (D89)

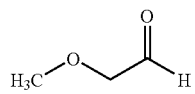

To a stirred suspension of chromatographic grade silica gel (3.8 g) in dry DCM (25 mL) was added NaIO4 (3.8 mL, 0.65M aq. solution) dropwise. A solution of 3-(methyloxy)-1,2-propanediol (200 mg, 1.9 mmol) in 1,2-DCE was added and reaction mixture was stirred at room temperature. After 2 hours, tlc showed complete reaction so the reaction mixture was filtered and the filter cake was washed with further 1,2-DCE. The filtrate containing the title compound was used directly in the next step (D90)

Description 90

1,1-Dimethylethyl (2S)-2-methyl-4-[(4-{[2-(methyloxy)ethyl]amino}phenyl)methyl]-1-piperazinecarboxylate (D90)

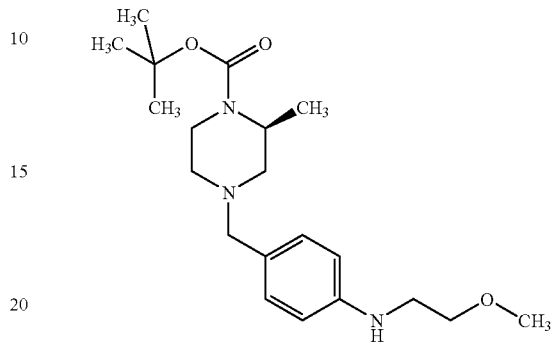

A mixture of 1,1-dimethylethyl (2S)-4-[(4-aminophenyl)methyl]-2-methyl-1-piperazinecarboxylate (D2) (0.30 g, 1 mmol), (methyloxy)acetaldehyde (D89), sodium tri(acetoxy)borohydride (0.417 g, 2 mmol) and triethylamine (0.165 mL, 1.2 mmol) in 1,2-DCE (15 mL) was stirred under Ar at room temperature for 19 hours. Saturated NaHCO₃ (20 mL) was added and reaction mixture stirred for a further 1 hour. The reaction mixture was further diluted with DCM (25 mL) and water (10 mL). The aqueous layer was then extracted with DCM (×3) and the combined organic layers were dried (Na₂SO₄) and concentrated in vacuo. The crude material was purified by column chromatography on silica eluting with 0-50% EtOAc/petroleum ether to give the title compound (0.310 g). $\delta_H$ (CDCl₃, 400 MHz) 7.12 (2H, d), 6.59 (2H, d), 4.15 (1H, m), 3.99 (1H, br.s), 3.78 (1H, d), 3.61 (2H, t), 3.40 (3H, s), 3.28 (3H, m), 3.08 (1H, td), 2.74 (1H, d), 2.58 (1H, d), 2.06 (1H, m), 1.94 (1H, m), 1.45 (9H, s), 1.21 (3H, d). MS (ES⁺): 264.2, no molecular ion (MH⁺) observed.

Description 91

4-Bromo-2-methylbenzaldehyde (D91)

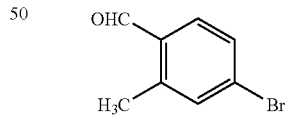

To 4-bromo-2-methylbenzonitrile (2 g, 10.2 mmol) in toluene (60 mL) cooled to 5 C under argon was added Dibal-H (11.2 mL, 1M solution in toluene, 11.2 mmol) dropwise. The reaction was stirred at 5° C. for 30 minutes then MeOH (3 mL) and 2 M H₂SO₄ (10 mL) were added dropwise. The mixture was stirred for ~19 h then concentrated in vacuo. The residue was re-dissolved in water/EtOAc. The organic layer was dried and concentrated to give the crude title compound as a brown oil (1.81 g) which was used in the next step without further purification. $\delta_H$ (CDCl₃, 400 MHz) 10.20 (1H, s), 7.65 (1H, d), 7.50 (1H, dd), 7.43 (1H, m), 2.64 (3H, s).

Description 92

1,1-Dimethylethyl (4-formyl-3-methylphenyl)methylcarbamate (D93)

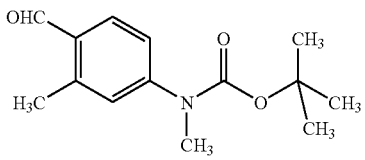

The title compound was prepared from crude 4-bromo-2-methylbenzaldehyde (D91) and 1,1-dimethylethyl methylcarbamate (D83) using a method similar to that described for D84 in Description 84. $\delta_H$ (CDCl$_3$, 400 MHz) 10.20 (1H, s), 7.76 (1H, d), 7.28 (1H, dd), 7.19 (1H, d), 3.31 (3H, s), 2.66 (3H, s), 1.49 (9H, s).

Description 93

2-Methyl-4-(methylamino)benzaldehyde (D93)

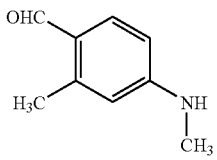

To 1,1-dimethylethyl (4-formyl-3-methylphenyl)methylcarbamate (D92) (0.614 g, 2.47 mmol) in DCM (60 mL) at room temperature under argon was added TFA (15 mL) dropwise. The mixture was stirred for 0.5 h then concentrated. The residue was re-dissolved in DCM and water and the aqueous layer was basified with NaOH solution. The DCM layer was separated, dried (Na$_2$SO$_4$) and concentrated to give the crude title compound as a yellow oil (0.397 g) which was used in the next step without further purification. $\delta_H$ (CDCl$_3$, 400 MHz) 9.98 (1H, s), 7.63 (1H, d), 6.47 (1H, dd), 6.35 (1H, d), 4.35 (1H, br.s), 2.91 (3H, d), 2.60 (3H, s). MS (ES): MH$^+$ 150.1.

Description 94

6-(Methylamino)-3-pyridinecarbonitrile (D94)

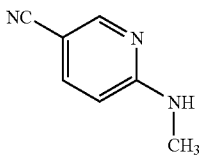

Four batches of 6-chloro-3-pyridinecarbonitrile (0.40 g, 2.89 mmol) in methylamine (16 mL, 2M solution in THF) were each heated at 80° C. for 30 minutes in a microwave reactor. The reaction mixtures were combined and concentrated in vacuo. The residue was re-dissolved in EtOAc/water and the organic layer was separated, dried (Na$_2$SO$_4$) and concentrated. The crude product was purified by column chromatography; elution with EtOAc/petroleum ether gave the title compound as a white solid (1.46 g). $\delta_H$ (CDCl$_3$, 400 MHz) 8.37 (1H, d), 7.59 (1H, dd), 6.39 (1H, dd), 5.19 (1H, br.s), 2.99 (3H, d). MS (ES): MH$^+$ 134.2.

Description 95

6-(Methylamino)-3-pyridinecarbaldehyde (D95)

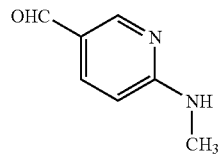

To 6-(methylamino)-3-pyridinecarbonitrile (D94) (0.1 g, 0.752 mmol) in toluene (10 mL) cooled to −78 C under argon was added Dibal-H (1.88 mL, 1M solution in toluene, 11.2 mmol) dropwise. The reaction was stirred at −78° C. and then allowed to warm to room temperature overnight. MeOH (0.47 mL) and 2 M H$_2$SO$_4$ (1.42 mL) were added and mixture was stirred for 1.5 h then concentrated in vacuo. The residue was partitioned between water and EtOAc. The aqueous layer was extracted with EtOAc and the combined organic layers were dried and concentrated to give the title compound (0.067 g). $\delta_H$ (CDCl$_3$, 400 MHz) 9.78 (1H, s), 8.52 (1H, d), 7.92 (1H, dd), 6.45 (1H, d), 5.38 (1H, br.s), 3.04 (3H, d). MS (ES): MH$^+$ 137.1.

Description 96

1,1-Dimethylethyl (2S)-2-methyl-4-{[6-(methylamino)-3-pyridinyl]methyl}-1-piperazinecarboxylate (D96)

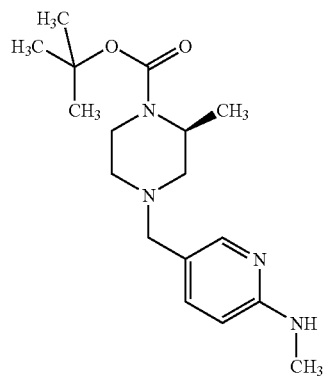

The title compound was prepared from 6-(methylamino)-3-pyridinecarbaldehyde (D95) and 1,1-dimethylethyl (2S)-2-methyl-1-piperazinecarboxylate using a method similar to that described for D81 in Description D81A. $\delta_H$ (CDCl$_3$, 400 MHz) 7.97 (1H, d), 7.44 (1H, dd), 6.38 (1H, d), 4.51 (1H, m), 4.17 (1H, br.s), 3.79 (1H, d), 3.38 (1H, d), 3.26 (1H, d), 3.07 (1H, td), 2.92 (3H, d), 2.74 (1H, m), 2.57 (1H, m), 2.09 (1H, dd), 1.96 (1H, m), 1.45 (9H, s), 1.20 (3H, d). MS (ES$^+$): 343.2 (MNa$^+$), 265.2, no molecular ion (MH$^+$) observed.

Description 97

6-Amino-4-methyl-3-pyridinecarbonitrile (D97)

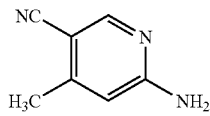

A mixture of 5-bromo-4-methyl-2-pyridinamine (0.50 g, 2.7 mmol) and copper (I) cyanide (0.263 g, 2.9 mmol) in DMF (12 mL) was heated at 200° C. for a total of 1.75 h in a microwave reactor. The reaction mixture was diluted with EtOAc and water. The resulting thick dark precipitate was filtered off. The filtrate was extracted with EtOAc (×3) and the combined extracts were dried and concentrated to give a dark yellow solid (0.115 g). The filter cake was and washed with 1:1 DCM/MeOH (1 L) which was concentrated to give a second batch of dark yellow solid (0.047 g). The filter cake was washed with 2M $NH_3$ in MeOH (200 mL) which was concentrated to give a dark green solid (0.533 g). These 3 batches of solids were purified by column chromatography using 0-100% EtOAc/hexane as the eluent to give the title compound as a white solid (total yield: 0.213 g). $\delta_H$ ($CDCl_3$, 400 MHz) 8.28 (1H, s), 6.36 (1H, s), 4.87 (2H, br.s), 2.40 (3H, s). MS (ES): $MH^+$ 134.1.

Description 98

N-(5-Cyano-4-methyl-2-pyridinyl)-2,2,2-trifluoroacetamide (D98)

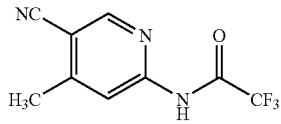

To a solution of 6-amino-4-methyl-3-pyridinecarbonitrile (D97) (0.213 g, 1.6 mmol) and 2,6-lutidine (0.37 mL, 3.2 mmol) in DCM (20 mL) cooled to 0° C. under argon was added trifluoroacetic anhydride (0.22 mL, 1.6 mmol) as a solution in DCM. The reaction mixture was stirred for 17 h, gradually warming to room temperature. The reaction mixture was re-cooled to 0° C. and further 2,6-lutidine (0.37 mL) and trifluoroacetic anhydride (0.22 mL) were added. The reaction was stirred at room temperature for 4 h then diluted with 10% citric acid solution and extracted with DCM. The DCM layer was washed with brine, dried and concentrated to give the crude product which was purified by column chromatography. Elution with 0-100% EtOAc/hexane gave the title compound as a white solid (0.299 g). $\delta_H$ ($CDCl_3$, 400 MHz) 8.68 (1H, br.s), 8.55 (1H, s), 8.21 (1H, s), 2.62 (3H, s).

Description 99

6-Amino-4-methyl-3-pyridinecarbaldehyde (D99)

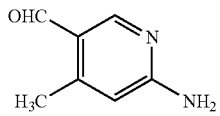

A solution of N-(5-cyano-4-methyl-2-pyridinyl)-2,2,2-trifluoroacetamide (D98) (0.050 g, 0.22 mmol) in formic acid (1.35 mL) was diluted with water (0.48 mL) and nickel/aluminium alloy (0.122 g) was added. The reaction mixture was heated at reflux under argon for 2 h then filtered while still hot, washing with further formic acid (3×5 mL). The filtrate and washings were concentrated, diluted with toluene (5 mL) and re-concentrated to give the crude title compound as a pale yellow solid (0.053 g) which was used in the next step without further purification. $\delta_H$ ($CDCl_3$, 400 MHz) 9.91 (1H, s), 8.34 (1H, s), 6.31 (1H, s), 5.49 (2H, br.s), 2.57 (3H, s). MS (ES): $MH^+$ 137.2.

Description 100

1,1-Dimethylethyl (2S)-4-[(6-amino-4-methyl-3-pyridinyl)methyl]-2-methyl-1-piperazinecarboxylate (D100)

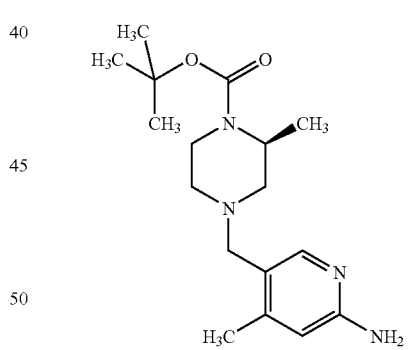

A mixture of 6-amino-4-methyl-3-pyridinecarbaldehyde (D99) (0.053 g, 0.39 mmol), 1,1-dimethylethyl (2S)-2-methyl-1-piperazinecarboxylate (0.117 g, 0.58 mmol) and sodium tri(acetoxy)borohydride (0.206 g, 0.97 mmol) in 1,2-DCE (10 mL) was sonicated to aid dissolution of the starting material then stirred at room temperature overnight. Saturated aqueous $NaHCO_3$ (30 mL) was added and the mixture was stirred for 24 h. The reaction mixture was extracted with DCM (3×10 mL) and the organics were dried and concentrated to give the crude title compound as an oil (0.067 g) which was used in the next step without further purification. MS (ES): $MH^+$ 321.3, $MNa^+$ 343.3.

Description 101

1,1-Dimethylethyl (2S)-2-methyl-4-{[4-methyl-6-(methylamino)-3-pyridinyl]methyl}-1-piperazinecarboxylate (D101)

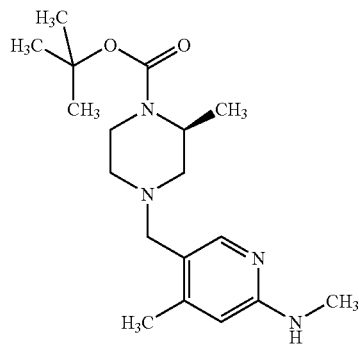

To 1,1-dimethylethyl (2S)-4-[(6-amino-4-methyl-3-pyridinyl)methyl]-2-methyl-1-piperazinecarboxylate (D100) (0.067 g, 0.21 mmol) in dry MeOH (4 mL) under an argon atmosphere was added paraformaldehyde (0.019 g, 0.63 mmol) and sodium methoxide (0.057 g, 1.00 mmol). The mixture was stirred at 50° C. overnight then sodium borohydride (0.024 g, 0.63 mmol) was added and the reaction stirred at 50° C. for 24 h. The reaction mixture was concentrated in vacuo. The residue was partitioned between DCM and saturated aqueous NaHCO$_3$ and stirred for 0.5 h. The aqueous phase was extracted with DCM (3×5 mL) and the combined organics were dried and concentrated to give a crude colourless oil. Column chromatography eluting with 0-10% MeOH/DCM gave the crude title compound as a colourless oil (0.037 g) which was used in the next step without further purification. MS (ES): MH$^+$ 335.3.

Description 102

1-(Bromomethyl)-2-chloro-4-nitrobenzene (D102)

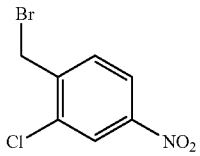

A mixture of 2-chloro-4-nitrotoluene (0.20 g, 1.17 mmol), N-bromosuccinimide (0.228 g, 1.28 mmol) and benzoyl peroxide (0.014 g, 0.058 mmol) in tetrachloromethane (7 mL) was irradiated (500 W lamp) at reflux overnight. The reaction mixture was concentrated to give a yellow oil/solid (0.391 g) which was used directly in the next step without further purification.

Description 103

1,1-Dimethylethyl (2S)-4-[(2-chloro-4-nitrophenyl)methyl]-2-methyl-1-piperazinecarboxylate (D103)

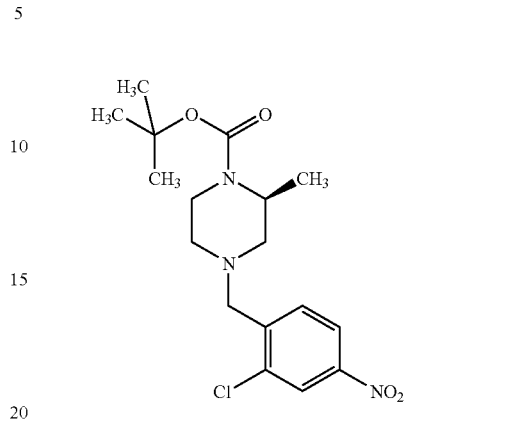

A mixture of crude 1-(bromomethyl)-2-chloro-4-nitrobenzene (D102) (0.391 g), 1,1-dimethylethyl (2S)-2-methyl-1-piperazinecarboxylate hydrochloride (0.407 g, 1.72 mmol) and Hunig's base (0.625 mL, 3.59 mmol) in dry DMF (3 mL) was stirred at room temperature for 10 minutes. The reaction mixture was concentrated to give an orange oil which was dissolved in DCM and washed with water (33 2) and brine, then dried and concentrated to give an orange oil. Purification by column chromatography eluting with 0-30% EtOAc/pentane gave the title compound as a yellow oil (0.199 g). δ$_H$ (CDCl$_3$, 400 MHz) 8.24 (1H, d), 8.12 (1H, dd), 7.77 (1H, d), 4.24 (1H, br.s), 3.85 (1H, d), 3.63 (2H, s), 3.14 (1H, td), 2.76 (1H, m), 2.59 (1H, m), 2.33 (1H, dd), 2.18 (1H, m), 1.47 (9H, s), 1.28 (3H, d). MS (ES): MH$^+$ 370/372.

Description 104

1,1-Dimethylethyl (2S)-4-[(4-amino-2-chlorophenyl)methyl]-2-methyl-1-piperazinecarboxylate (D104)

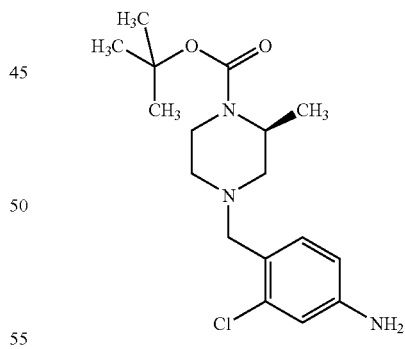

A mixture of 1,1-dimethylethyl (2S)-4-[(2-chloro-4-nitrophenyl)methyl]-2-methyl-1-piperazinecarboxylate (D103) (0.199 g, 0.538 mmol), triethylamine (0.75 mL, 5.38 mmol) and 5% Pt/C catalyst (0.134 g) in MeOH (5 mL) was hydrogenated at room temperature and atmospheric pressure for 3 h. The catalyst was removed by filtration and the filtrate was concentrated to give a colourless oil which was dissolved in DCM. The DCM solution was washed with water (×2) and brine, then dried and concentrated to give the crude product. Purification by column chromatography eluting with 10-40% EtOAc/pentane gave the title compound as a colourless oil (0.125 g). $\delta_H$ (CDCl$_3$, 400 MHz) 7.19 (1H, d), 6.69 (1H, d), 6.54 (1H, dd), 4.18 (1H, br.s), 3.79 (1H, d), 3.70 (2H, br.s), 3.45 (2H, m), 3.07 (1H, td), 2.74 (1H, m), 2.60 (1H, m), 2.19 (1H, dd), 2.03 (1H, m), 1.45 (9H, s), 1.22 (3H, d). MS (ES): MH$^+$ 340/342.

Description 105

1,1-Dimethylethyl (2S)-4-{[2-chloro-4-(methylamino)phenyl]methyl}-2-methyl-1-piperazinecarboxylate (D105)

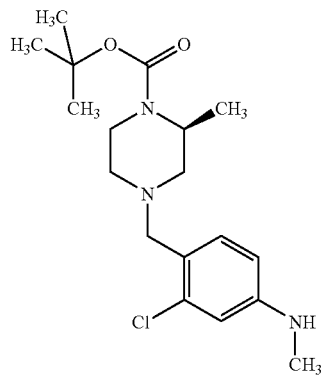

The title compound was prepared from 1,1-dimethylethyl (2S)-4-[(4-amino-2-chlorophenyl)methyl]-2-methyl-1-piperazinecarboxylate (D104) using a method similar to that described for D3 in Description 3A although the reaction was heated at 50° C. overnight prior to, and for 24 h after addition of sodium borohydride.(3 eq.). MS (ES): MH$^+$ 354/356.

Description 106

1,1-Dimethylethyl (2S)-4-({6-[[(6-chloro-3-pyridinyl)carbonyl](methyl)amino]-3-pyridinyl}methyl)-2-methyl-1-piperazinecarboxylate (D106)

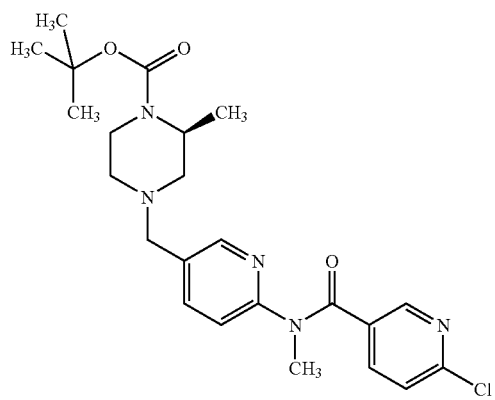

To 1,1-dimethylethyl (2S)-2-methyl-4-{[6-(methylamino)-3-pyridinyl]methyl}-1-piperazinecarboxylate (D96) (0.150 g, 0.469 mmol) and triethylamine (0.098 mL, 0.703 mmol) in DCM (7 mL) under argon was added 6-chloro-3-pyridinecarbonyl chloride (0.099 g, 0.562 mmol). The mixture was stirred at room temperature for ~0.3 h then diluted with DCM and water. The organic layer was dried and concentrated to give the crude product which was purified by column chromatography. Elution with EtOAc/DCM gave the title compound as a white colourless gum (0.139 g). $\delta_H$ (CDCl$_3$, 400 MHz) 8.33 (1H, d), 8.19 (1H, d), 7.70 (1H, dd), 7.57 (1H, dd), 7.23 (1H, d), 6.86 (1H, d), 4.20 (1H, br.s), 3.82 (1H, d), 3.58 (3H, s), 3.49 (1H, d), 3.37 (1H, d), 3.08 (1H, td), 2.70 (1H, d), 2.49 (1H, d), 2.16 (1H, dd), 2.04 (1H, m), 1.46 (9H, s), 1.19 (3H, d). MS (ES): MH$^+$ 460/462

Description 107

1,1-Dimethylethyl (2S)-4-({4-[[(6-chloro-2-pyridinyl)carbonyl](methyl)amino]phenyl}methyl)-2-methyl-1-piperazinecarboxylate (D107)

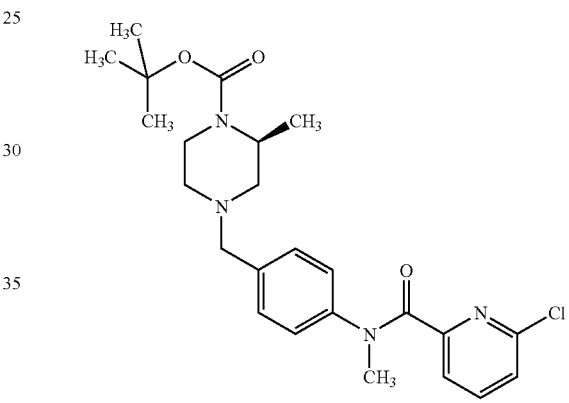

Step 1: 6-bromo-2-pyridinecarboxylic acid (0.348 g, 1.72 mmol) was dissolved in dry dioxane (15 mL) and thionyl chloride (0.570 mL, 7.84 mmol) was added. The reaction mixture was stirred at reflux for 3 h then concentrated in vacuo, re-dissolved in dioxane (15 mL) and re-concentrated to give 6-chloro-2-pyridinecarbonyl chloride as a pale yellow solid which was used directly in step 2.

Step 2: The acid chloride from step 1 was dissolved in DCM (15 mL) and added to a mixture of 1,1-dimethylethyl (2S)-2-methyl-4-{[4-(methylamino)phenyl]methyl}-1-piperazinecarboxylate (D3) (0.500 g, 1.57 mmol) and triethylamine (0.284 mL, 2.04 mmol) in DCM (15 mL). The reaction mixture was stirred at room temperature overnight and then washed with water (×2) and brine. The organic layer was dried and concentrated to give the crude product, which was purified by column chromatography. Elution with 20-60% EtOAc/pentane yielded the title compound as a yellow oil/solid (0.658 g). $\delta_H$ (CDCl$_3$, 400 MHz) 7.56 (1H, m), 7.46 (1H, m), 7.17 (2H, m), 6.99 (2H, m), 4.16 (1H, br.s), 3.79 (1H, d), 3.50 (3H, s), 3.46 (1H, d), 3.32 (1H, d), 3.07 (1H, m), 2.69 (1H, d), 2.50 (1H, d), 2.08 (1H, m), 1.97 (1H, d), 1.46 (9H, s), 1.19 (3H, d). MS (ES): MH$^+$ 459/461.

Description 108

1,1-Dimethylethyl (2S)-4-({4-[[(6-bromo-3-pyridinyl)carbonyl](methyl)amino]phenyl}methyl)-2-methyl-1-piperazinecarboxylate (D108)

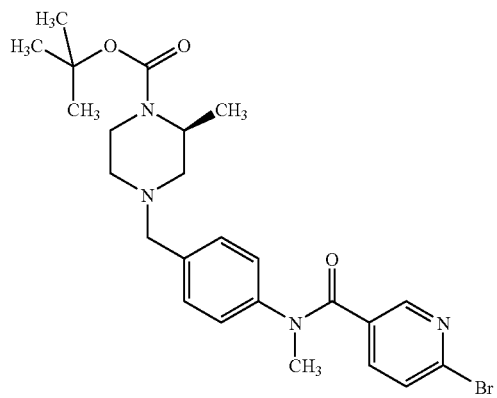

To 1-hydroxybenzotriazole (0.967 g 7.16 mmol) and N-benzyl-N'-cyclohexylcarbodiimide resin (4.48 g, 1.6 mmol/g, 7.16 mmol) in DMF (15 mL) was added 6-bromo-3-pyridinecarboxylic acid (0.964 g, 4.77 mmol) in DMF (15 mL). The mixture was stirred for 30 minutes under an argon atmosphere and 1,1-dimethylethyl (2S)-2-methyl-4-{[4-(methylamino)phenyl]methyl}-1-piperazinecarboxylate (D3) (1.52 g, 4.77 mmol) in DCM (15 mL) was added. The mixture was stirred for 65 h at room temperature. PS-trisamine resin (2 eq. relative to acid), PS-isocyanate resin (2 eq. relative to amine) and MP-carbonate resin (5 eq. relative to HOBt) were added and the mixture stirred for 4 h at room temperature. The mixture was filtered to remove the resins which were then washed with further DCM. The filtrate was concentrated to give the crude product which was purified by column chromatography. Elution with an EtOAc/petroleum ether gradient yielded the title compound as a white solid (1.43 g). $\delta_H$ (CDCl$_3$, 400 MHz) 8.18 (1H, d), 7.51 (1H, dd), 7.32 (1H, d), 7.25 (2H, d), 6.98 (2H, d), 4.18 (1H, br.s), 3.80 (1H, d), 3.49 (3H, s), 3.47 (1H, d), 3.34 (1H, d), 3.08 (1H, td), 2.69 (1H, d), 2.49 (1H, d), 2.11 (1H, dd), 1.98 (1H, m), 1.46 (9H, s), 1.20 (3H, d). MS (ES): MH$^+$ 503/505.

Tabulated compounds D109-D110 were prepared using methods similar to those described in Description 15 using the appropriate aniline precursor and appropriate carboxylic acid.

| Desc'n | Aniline Precursor | Structure | Name | Method Comment Step 1 | Method Comment Step 2 | MH+ |
|---|---|---|---|---|---|---|
| D109 | D86 | 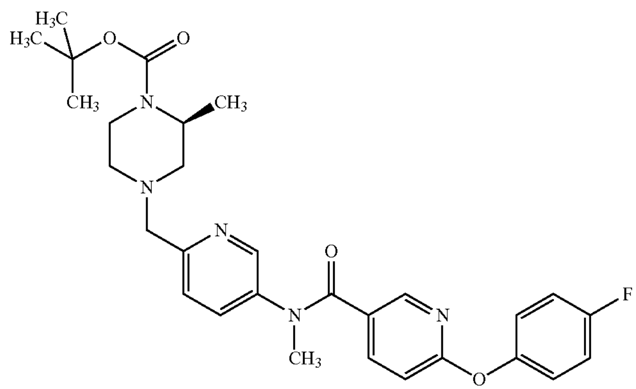 | 1,1-dimethylethyl (2S)-4-({5-[({6-[(4-fluorophenyl)oxy]-3-pyridinyl}carbonyl)(methyl)amino]-2-pyridinyl}methyl)-2-methyl-1-piperazinecarboxylate | Similar method to D15 | Similar method to D15 although sat. aq. NaHCO₃ used in place of water in work-up | 536.3 |
| D110 | D86 | 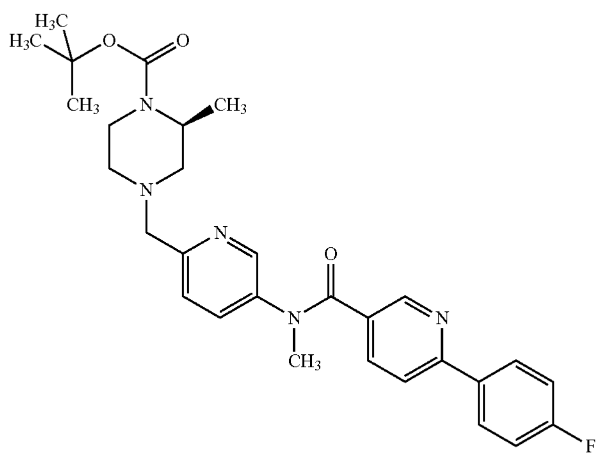 | 1,1-dimethylethyl (2S)-4-({5-[{[6-(4-fluorophenyl)-3-pyridinyl]carbonyl}(methyl)amino]-2-pyridinyl}methyl)-2-methyl-1-piperazinecarboxylate | Similar method to D15 | Similar method to D15 although sat. aq. NaHCO₃ used in place of water in work-up | 520.3 |

| Desc'n | Aniline Precursor | Structure | Name | Method Comment Step 1 | Method Comment Step 2 | MH+ |
|---|---|---|---|---|---|---|
| D111 | D3 | 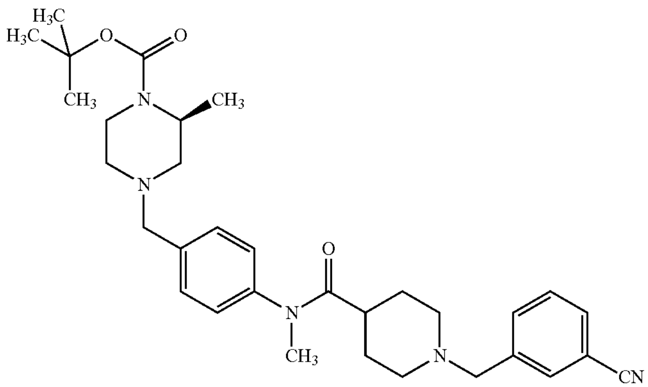 | 1,1-dimethylethyl (2S)-4-({4-[({1-[(3-cyanophenyl)methyl]-4-piperidinyl}carbonyl)(methyl)amino]phenyl}methyl)-2-methyl-1-piperazinecarboxylate | Similar method to D16 although reaction temp./time: room temperature, 0.75 h | Similar method to D16 | 546.4 |
| D112 | D3 | 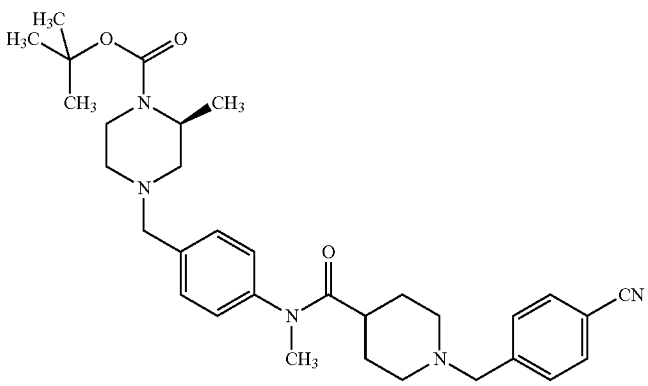 | 1,1-dimethylethyl (2S)-4-({4-[({1-[(4-cyanophenyl)methyl]-4-piperidinyl}carbonyl)(methyl)amino]phenyl}methyl)-2-methyl-1-piperazinecarboxylate | Similar method to D16 although reaction temp./time: room temperature, 0.75 h | Similar method to D16 | 546.4 |

-continued

| Desc'n | Aniline Precursor | Structure | Name | Method Comment Step 1 | Method Comment Step 2 | MH+ |
|---|---|---|---|---|---|---|
| D113 | D87 | 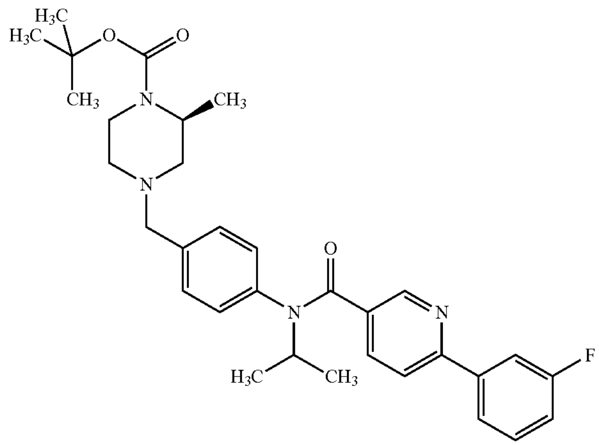 | 1,1-dimethylethyl (2S)-4-({4-[{[6-(3-fluorophenyl)-3-pyridinyl]carbonyl}(1-methylethyl)amino]phenyl}methyl)-2-methyl-1-piperazinecarboxylate | Similar method to D16 although reaction time: 0.75 h | Similar method to D16 although sat. aq. NaHCO₃ used in place of water in work-up | 547.3 |
| D114 | D88 | 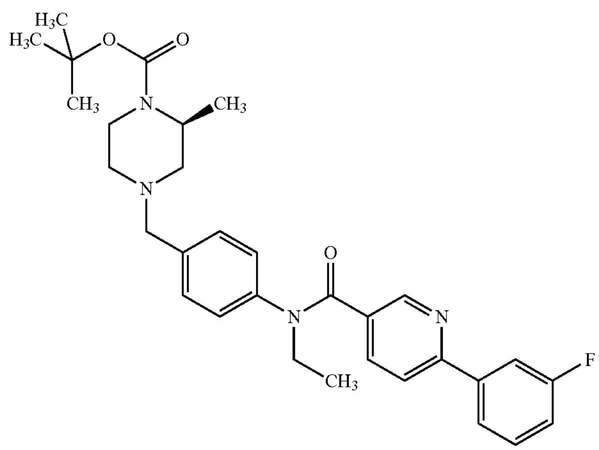 | 1,1-dimethylethyl (2S)-4-[(4-{[6-(3-fluorophenyl)-3-pyridinyl]carbonyl}(ethyl)amino]phenyl}methyl)-2-methyl-1-piperazinecarboxylate | Similar method to D16 although reaction time: 1 h | Similar method to D16 although sat. aq. NaHCO₃ used in place of water in work-up | 533.2 |

| Desc'n | Aniline Precursor | Structure | Name | Method Comment Step 1 | Method Comment Step 2 | MH+ |
|---|---|---|---|---|---|---|
| D115 | D90 | 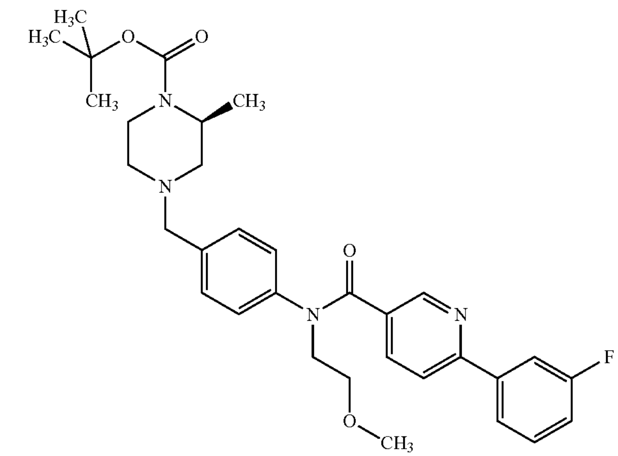 | 1,1-dimethylethyl (2S)-4-{(4-{[(6-(3-fluorophenyl)-3-pyridinyl]carbonyl}[2-(methyloxy)ethyl]amino]phenyl)methyl]-2-methyl-1-piperazinecarboxylate | Similar method to D16 although reaction time: 0.5 h | Similar method to D16 although sat. aq. NaHCO₃ used in place of water in work-up | 563.2 |
| D116 | D81 | 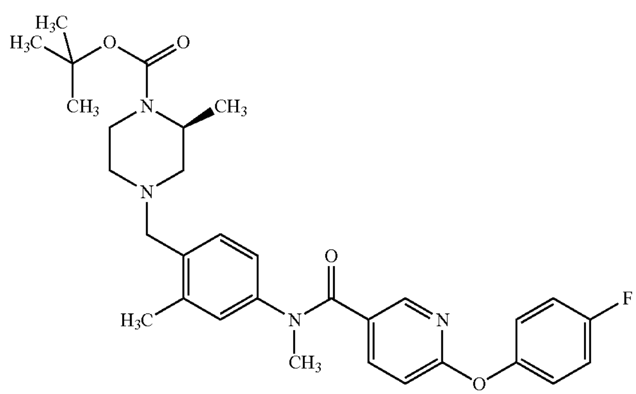 | 1,1-dimethylethyl (2S)-4-({4-[{[6-[(4-fluorophenyl)oxy]-3-pyridinyl}carbonyl](methyl)amino]-2-methylphenyl}methyl)-2-methyl-1-piperazinecarboxylate | Similar method to D16 although reaction time: 0.5 h | Similar method to D16 | 549.3 |

-continued

| Desc'n | Aniline Precursor | Structure | Name | Method Comment Step 1 | Step 2 | MH+ |
|---|---|---|---|---|---|---|
| D117 | D96 | (structure shown) | 1,1-dimethylethyl (2S)-4-({6-[{[6-(3-fluorophenyl)-3-pyridinyl]carbonyl}(methyl)amino]-3-pyridinyl}methyl)-2-methyl-1-piperazinecarboxylate | Similar method to D16 although reaction time: 1 h | Similar method to D16 | 520.2 |

Tabulated compounds D111-D117 were prepared using methods similar to those described in Description 16 using the appropriate aniline precursor and appropriate carboxylic acid.

Description 118

1,1-Dimethylethyl(2S)-4-({6-[({6-[(4-fluorophenyl)oxy]-3-pyridinyl}carbonyl)(methyl)amino]-4-methyl-3-pyridinyl}methyl)-2-methyl-1-piperazinecarboxylate (D118)

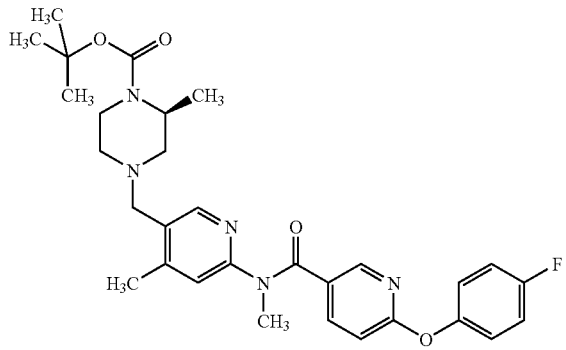

Step 1: 6-[(4-Fluorophenyl)oxy]-3-pyridinecarboxylic acid (D14) (0.032 g, 0.14 mmol) was solubilised in dry dioxane (2 mL). Thionyl chloride (0.081 mg, 0.14 mmol) was added drop-wise and the reaction mixture heated at reflux for 1.25 h. The reaction mixture was concentrated, and then re-concentrated from DCM to give 6-[(4-fluorophenyl)oxy]-3-pyridinecarbonyl chloride which was used directly in step 2

Step 2: 1,1-Dimethylethyl (2S)-2-methyl-4-{[4-methyl-6-(methylamino)-3-pyridinyl]methyl}-1-piperazinecarboxylate (D101) (0.038 g, 0.11 mmol) was dissolved in dry DCM (2 mL). Triethylamine (0.016 g, 0.16 mmol) was added dropwise and after 5 minutes a solution of the acid chloride from step 1 in dry DCM (2 mL) was added dropwise. The reaction mixture was then left stirring under argon at room temperature overnight. Saturated aqueous NaHCO$_3$ (15 mL) was added and the aqueous layer extracted with DCM (3×5 mL). The organic extracts were dried (Na$_2$SO$_4$) and the crude product was purified by column chromatography. Elution with a 0-100% EtOAc/petroleum ether gradient gave the title compound as a colourless oil (0.026 g). MS (ES): MH$^+$ 550.4

Tabulated compounds D119-D122 were prepared using methods similar to those described in Description 16 using the appropriate aniline precursor and appropriate carboxylic acid.

| Desc'n | Aniline Precursor | Structure | Name | Method Comment Step 1 | Method Comment Step 2 | MH+ |
|---|---|---|---|---|---|---|
| D119 | D90 | 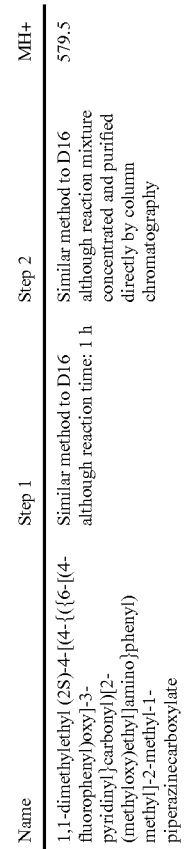 | 1,1-dimethylethyl (2S)-4-[(4-{(6-[(4-fluorophenyl)oxy]-3-pyridinyl}carbonyl)[2-(methyloxy)ethyl]amino}phenyl)methyl]-2-methyl-1-piperazinecarboxylate | Similar method to D16 although reaction time: 1 h | Similar method to D16 although reaction mixture concentrated and purified directly by column chromatography | 579.5 |
| D120 | D105 | 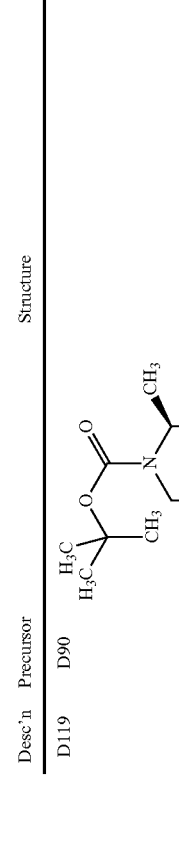 | 1,1-dimethylethyl (2S)-4-({2-chloro-4-[({6-[(4-fluoro-phenyl)oxy]-3-pyridinyl}carbonyl)(methyl)amino]phenyl}methyl)-2-methyl-1-piperazinecarboxylate | Similar method to D16 although reaction time: 3 h | Similar method to D16 although reaction time: 48 h. Reaction mixture concentrated and purified directly by column chromatography | 569/571 |

| Desc'n | Aniline Precursor | Structure | Name | Method Comment Step 1 | Method Comment Step 2 | MH+ |
|---|---|---|---|---|---|---|
| D121 | D88 | 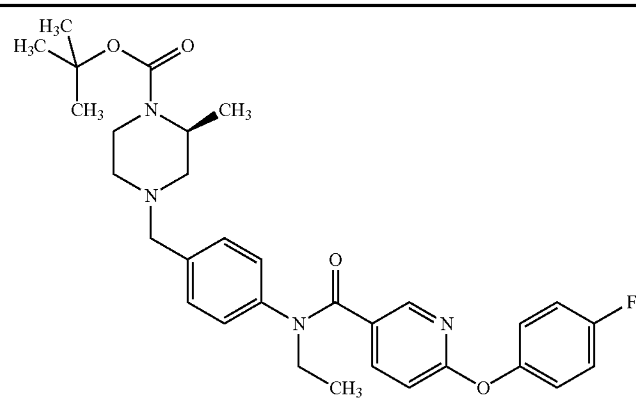 | 1,1-dimethyl-ethyl (2S)-4-({4-[ethyl({6-[(4-fluorophenyl)oxy]-3-pyridinyl}carbonyl)amino]phenyl}methyl)-2-methyl-1-piperazinecarboxylate | Similar method to D16 although reaction time: 1.5 h | Similar method to D16 with column chromatography and MDAP purification. | 549.4 |
| D122 | D3 | 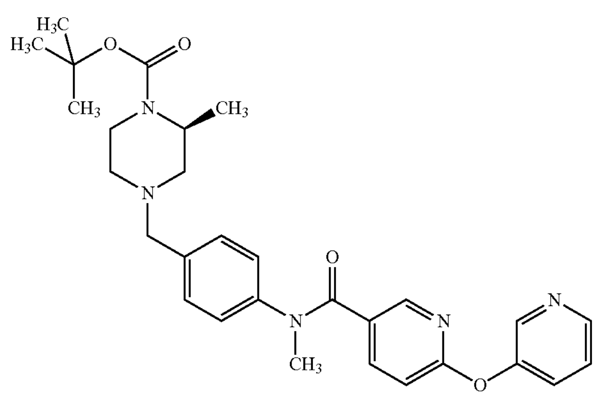 | 1,1-dimethylethyl (2S)-2-methyl-4-{[4-(methyl{[6-(3-pyridinyloxy)-3-pyridinyl]carbonyl}amino)phenyl]methyl}-1-piperazinecarboxylate | Similar method to D16 although reaction time: 1 h | Similar method to D16 although reaction mixture concentrated and purified directly by column chromatography | 518.2 |

Description 123

1,1-Dimethylethyl (2S)-2-methyl-4-[(4-{methyl[(4-{[4-(trifluoromethyl)phenyl]carbonyl}phenyl)carbonyl]amino}phenyl)methyl]-1-piperazinecarboxylate (D123)

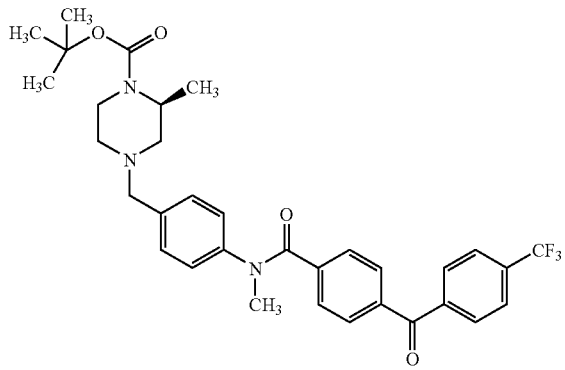

Step 1: 4-{[4-(Trifluoromethyl)phenyl]carbonyl}benzoic acid (200 mg, 0.68 mmol) was stirred in dioxane (5 mL) and thionyl chloride (0.496 mL, 6.8 mmol) added. The reaction mixture was heated at reflux for 1 h. Further thionyl chloride (0.496 mL, 6.8 mmol) was added and heating continued for 3 h. On cooling, the reaction mixture was concentrated in vacuo to give 4-{[4-(trifluoromethyl)phenyl]carbonyl}benzoyl chloride as an oily white liquid (0.286 g) which was used directly in step 2.

Step 2: The acid chloride from step 1 was taken up in DCM (2 mL) and added drop-wise to a mixture of 1,1-dimethylethyl (2S)-2-methyl-4-{[4-(methylamino)phenyl]methyl}-1-piperazinecarboxylate (D3) (0.170 g, 0.53 mmol) and triethylamine (0.11 mL) in DCM (2 mL). The reaction mixture was stirred at room temperature under argon overnight then diluted with water (20 mL) and DCM (20 mL). The aqueous layer was extracted with DCM (20 mL) and the combined organic layers were dried, concentrated and purified by column chromatography. Elution with 0-30% EtOAc/pentane gave the title compound as a colourless oil (0.244 g). MS (ES): MH+ 596.2.

Description 124

1,1-Dimethylethyl (2S)-4-({6-[({6-[(4-fluorophenyl)oxy]-3-pyridinyl}carbonyl)(methyl)amino]-3-pyridinyl}methyl)-2-methyl-1-piperazinecarboxylate (D124)

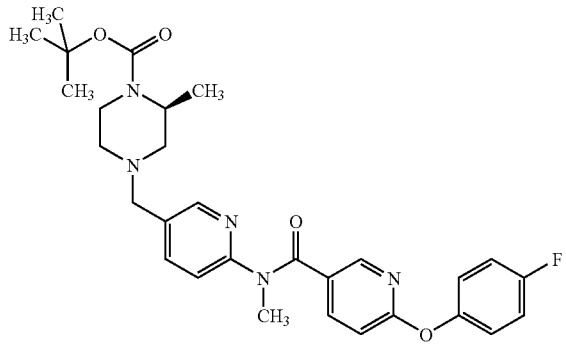

To 1,1-dimethylethyl (2S)-4-({6-[[(6-chloro-3-pyridinyl)carbonyl](methyl)amino]-3-pyridinyl}methyl)-2-methyl-1-piperazinecarboxylate (D106) (0.139 g, 0.303 mmol) in DMF (4 mL) under an argon atmosphere was added potassium carbonate (0.293 g, 0.212 mmol) and 4-fluorophenol (0.169 g, 1.51 mmol). The reaction mixture was stirred and heated at 130° C. for 5 h then concentrated in vacuo. The residue was re-dissolved in DCM/water. The organic layer was washed with 2M NaOH solution and brine then dried (Na$_2$SO$_4$) and concentrated to give the crude product which was purified by column chromatography. Elution with EtOAc/DCM gave the title compound as a colourless oil (0.054 g). MS (ES): MH+ 536.2.

Description 125

1,1-Dimethylethyl (2S)-4-({4-[({6-[(4-fluorophenyl)oxy]-2-pyridinyl}carbonyl)(methyl)amino]phenyl}methyl)-2-methyl-1-piperazinecarboxylate (D125)

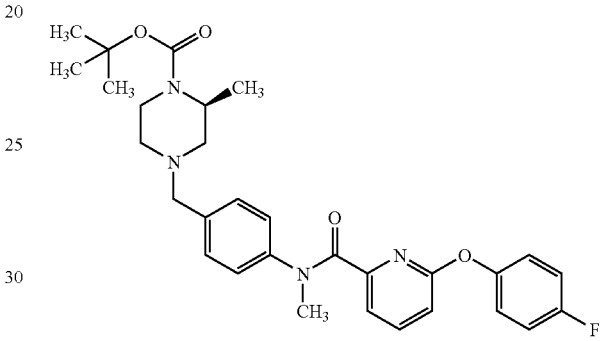

To sodium hydride (0.0174 g, 60% dispersion in mineral oil, 0.436 mmol) in DMF (4 mL) was added 4-fluorophenol (0.0488 g, 0.436 mmol) and the mixture stirred under an argon atmosphere for 20 minutes. 1,1-Dimethylethyl (2S)-4-({4-[[(6-chloro-2-pyridinyl)carbonyl](methyl)amino]phenyl}methyl)-2-methyl-1-piperazinecarboxylate (D107) (0.100 g, 0.218 mmol) was added and the reaction mixture was heated in a microwave at 190° C. for 1.5 h. The reaction mixture was concentrated and the residue partitioned between DCM and water. The aqueous layer was further extracted with DCM and the combined organics were dried over Na$_2$SO$_4$ and concentrated to give a yellow oil which was purified by column chromatography to give the title compound as a colourless oil (0.0539 g). MS (ES): MH+ 535.4.

Description 126

1,1-Dimethylethyl (2S)-4-({4-[({6-[(3-fluorophenyl)oxy]-2-pyridinyl}carbonyl) (methyl)amino]phenyl}methyl)-2-methyl-1-piperazinecarboxylate (D126)

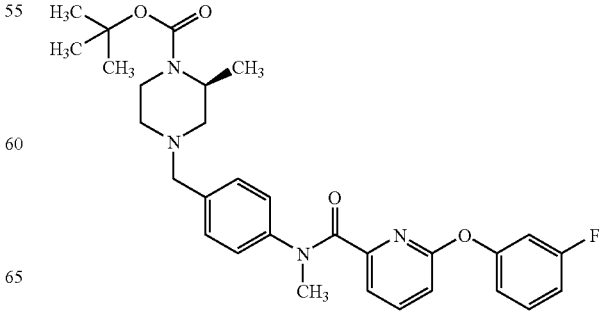

The title compound was prepared from 1,1-dimethylethyl (2S)-4-({4-[[(6-chloro-2-pyridinyl)carbonyl](methyl)amino]phenyl}methyl)-2-methyl-1-piperazinecarboxylate (D107) and 3-fluorophenol using a procedure similar to that described for D125 in Description 125 although the reaction time was 3.3 h. MS (ES): MH+ 535.4.

Description 127

1,1-Dimethylethyl (2S)-4-({4-[{[6-(4-fluoro-1-piperidinyl)-3-pyridinyl]carbonyl}(methyl)amino]phenyl}methyl)-2-methyl-1-piperazinecarboxylate (D127)

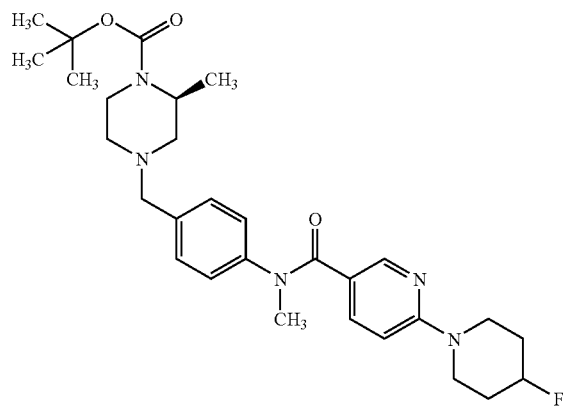

A mixture of 1,1-dimethylethyl (2S)-4-({4-[[(6-bromo-3-pyridinyl)carbonyl](methyl)amino]phenyl}methyl)-2-methyl-1-piperazinecarboxylate (D108) (0.050 g, 0.0993 mmol), 4-fluoropiperidine (0.055 g, 0.397 mmol) and triethylamine (0.069 mL, 0.497 mmol) in acetonitrile (4 mL) was heated at 85° C. overnight then in a microwave at 140° C. for 10 h. Further portions of 4-fluoropiperidine (5 eq.) and triethylamine (5 eq.) were added and the reaction heated at 170° C. for 2 h. The reaction mixture was concentrated and the residue dissolved in DCM/water. The aqueous layer was further extracted with DCM (×3) and the combined organics were dried (Na2SO4) and concentrated to give the title compound as a yellow oil (0.0538 g). MS (ES): MH+ 526.2.

Description 128

1,1-Dimethylethyl (2S)-4-({4-[{[6-(4,4-difluoro-1-piperidinyl)-3-pyridinyl]carbonyl}(methyl)amino]phenyl}methyl)-2-methyl-1-piperazinecarboxylate (D128)

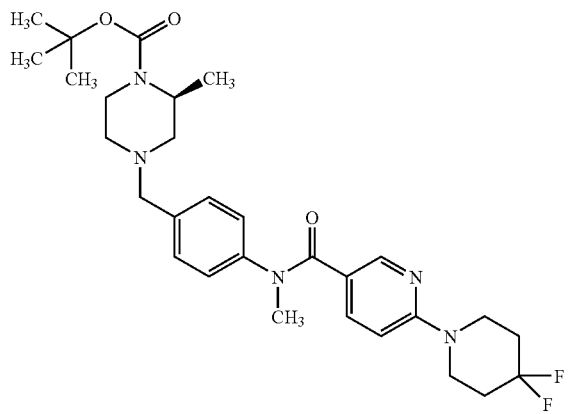

A mixture of 1,1-dimethylethyl (2S)-4-({4-[[(6-bromo-3-pyridinyl)carbonyl](methyl)amino]phenyl}methyl)-2-methyl-1-piperazinecarboxylate (D108) (0.050 g, 0.0993 mmol), 4,4-difluoropiperidine (0.141 g, 0.894 mmol) and triethylamine (0.138 mL, 0.993 mmol) in acetonitrile (4 mL) was heated in a microwave at 150° C. for 12 h. Further portions of 4,4-difluoropiperidine (4 eq.) and triethylamine (5 eq.) were added and the reaction heated at 150° C. for 1 h. The reaction mixture was concentrated and the residue dissolved in DCM/water. The aqueous layer was further extracted with DCM (×3) and the combined organics were dried (Na2SO4) and concentrated to give a yellow gum which was purified by column chromatography. Elution with 0-100% EtOAc/hexane gave a colourless gum which was a mixture (~9:1) of the title compound and unreacted D109 (0.0485 g). MS (ES): MH+ 544.2.

Description 129

1,1-Dimethylethyl (2S)-4-({4-[{[6-(3-fluorophenyl)-2-pyridinyl]carbonyl}(methyl)amino]phenyl}methyl)-2-methyl-1-piperazinecarboxylate (D129)

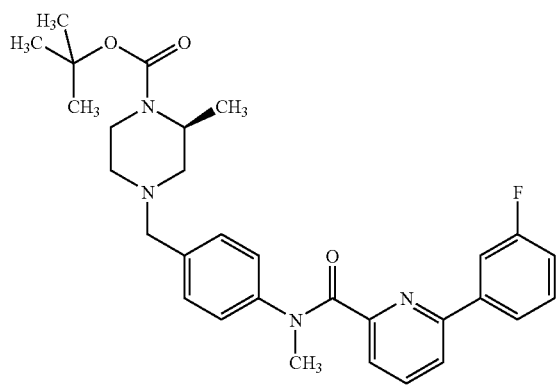

A mixture of 1,1-dimethylethyl (2S)-4-({4-[[(6-chloro-2-pyridinyl)carbonyl](methyl)amino]phenyl}methyl)-2-methyl-1-piperazinecarboxylate (D107) (0.0825 g, 0.179 mmol), 3-fluorobenzeneboronic acid (0.0302 g, 0.216 mmol), tetrakis-(triphenylphosphine)palladium (0) (0.0104 g, 0.009 mmol) and sodium carbonate (0.0762 g, 0.719 mmol) in a DME/water (4 mL, 1:1) was heated at 140° C. in a microwave for 10 minutes. The reaction mixture was diluted with DCM/water and the aqueous layer was further extracted with DCM (×3). The combined organics were dried and concentrated to give the crude product which was purified by column chromatography. Elution with 0-100% EtOAc/hexane gave the title compound as a colourless oil (0.0781 g). MS (ES): MH+ 519.3.

Tabulated compounds D130-D136 were prepared from the appropriate bromo-pyridine precursor as indicated and the appropriate boronic acid using methods similar to that described for D129 in Description 129.

| Desc'n | Bromo-pyridine Precursor | Structure | Name | Method Comment | MH+ |
|---|---|---|---|---|---|
| D130 | D72 | 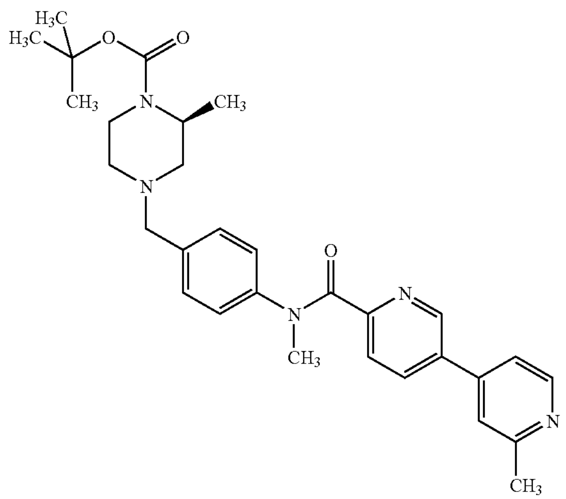 | 1,1-Dimethylethyl (2S)-2-methyl-4-[(4-{methyl[(2'-methyl-3,4'-bipyridin-6-yl)carbonyl]amino}phenyl)methyl]-1-piperazinecarboxylate | Similar to D103 although 2 eq. boronic acid used and reaction time was 20 minutes. | 516.2 |
| D131 | D72 | 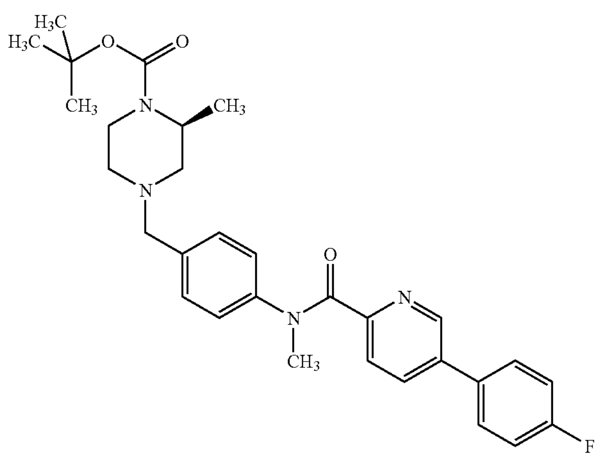 | 1,1-dimethylethyl (2S)-4-({4-[{[5-(4-fluorophenyl)-2-pyridinyl]carbonyl}(methyl)amino]phenyl}methyl)-2-methyl-1-piperazinecarboxylate | Similar to D103 although 1 eq. boronic acid used and reaction temperature/time was 150° C./5 minutes. | 519.2 |
| D132 | D72 | 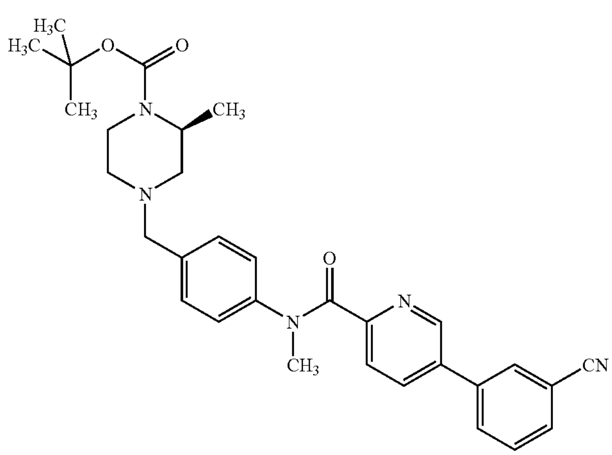 | 1,1-dimethylethyl (2S)-4-({4-[{[5-(3-cyanophenyl)-2-pyridinyl]carbonyl}(methyl)amino]phenyl}methyl)-2-methyl-1-piperazinecarboxylate | Similar to D103 although 1 eq. boronic acid used and reaction temperature/time was 150° C./5 minutes | 526.2 |

-continued

| Desc'n | Bromo-pyridine Precursor | Structure | Name | Method Comment | MH+ |
|---|---|---|---|---|---|
| D133 | D72 | 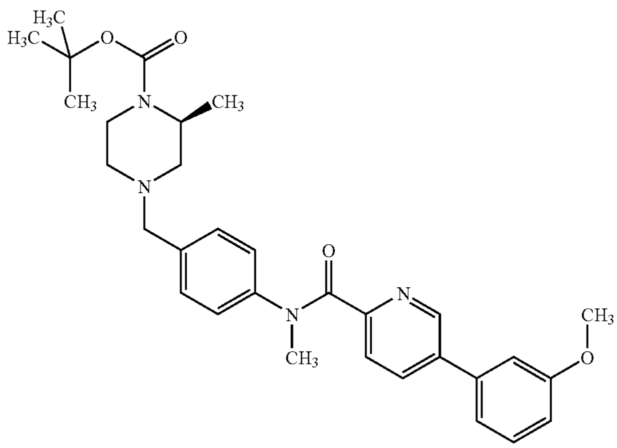 | 1,1-dimethylethyl (2S)-2-methyl-4-({4-[methyl({5-[3-(methyloxy)phenyl]-2-pyridinyl}carbonyl)amino]phenyl}methyl)-1-piperazinecarboxylate | Similar to D103 although 1 eq. boronic acid used and reaction temperature/time was 150° C./5 minutes. | 531.4 |
| D134 | D72 | 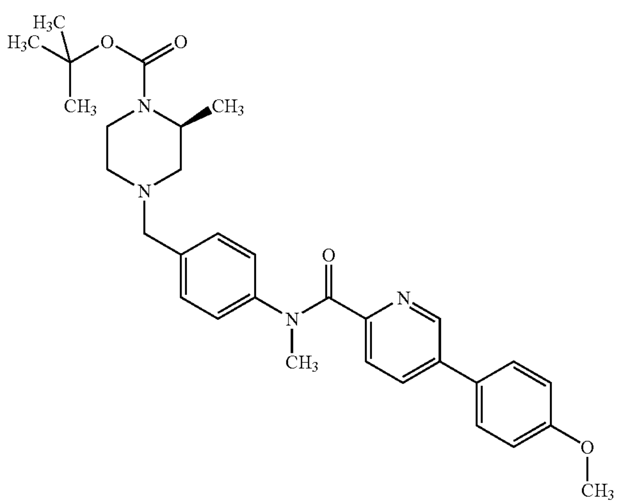 | 1,1-dimethylethyl (2S)-2-methyl-4-({4-[methyl({5-[4-(methyloxy)phenyl]-2-pyridinyl}carbonyl)amino]phenyl}methyl)-1-piperazinecarboxylate | Similar to D103 although 1 eq. boronic acid used and reaction temperature/time was 150° C./5 minutes. | 531.4 |
| D135 | D72 | 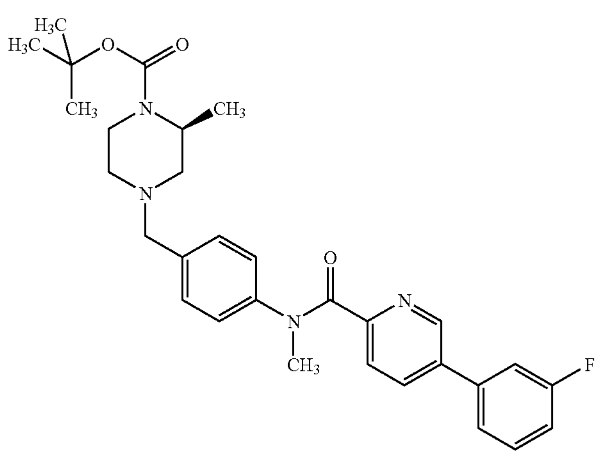 | 1,1-dimethylethyl (2S)-4-({4-[{[5-(3-fluorophenyl)-2-pyridinyl]carbonyl}(methyl)amino]phenyl}methyl)-2-methyl-1-piperazinecarboxylate | Similar to D103 although 1 eq. boronic acid used and reaction temperature/time was 150° C./5 minutes. | 519.3 |

-continued

| Desc'n | Bromo-pyridine Precursor | Structure | Name | Method Comment | MH+ |
|---|---|---|---|---|---|
| D136 | D108 | 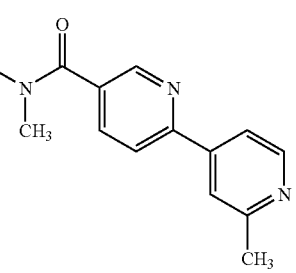 | 1,1-dimethylethyl (2S)-2-methyl-4-[(4-{methyl[(2'-methyl-2,4'-bipyridin-5-yl)carbonyl]amino}phenyl)methyl]-1-piperazinecarboxylate | Similar to D103 although 2 eq. boronic acid used and reaction time was 20 minutes. | 516.4 |

Description 137

1,1-Dimethylethyl (2S)-2-methyl-4-{[4-(methyl{[4-(2-pyridinyl)phenyl]carbonyl}amino)phenyl]methyl}-1-piperazinecarboxylate (D137)

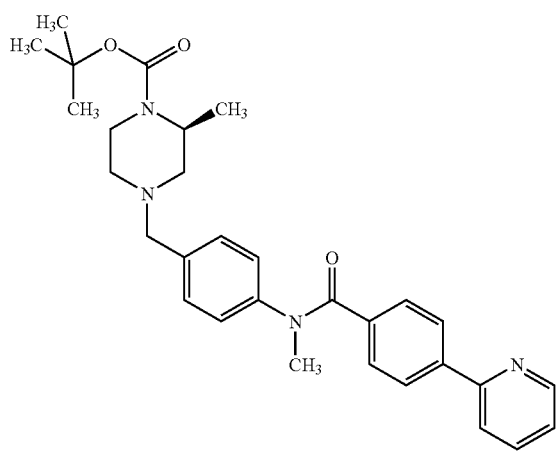

To 4-(2-pyridinyl)benzoic acid (0.0624 g, 0.313 mmol) in DMF (3 mL) was added N-benzyl-N'-cyclohexylcarbodiimide resin (0.294 g, 1.6 mmol/g, 0.47 mmol), 1-hydroxybenzotriazole (0.064 g, 0.47 mmol) and DCM (1 mL) and the mixture was shaken for 30 minutes. 1,1-Dimethylethyl (2S)-2-methyl-4-{[4-(methylamino)phenyl]methyl}-1-piperazine-carboxylate (D3) (100 mg, 0.313 mmol), DMF (3 mL) and DCM (1 mL) were then added and the mixture was shaken for ~2 days at room temperature The reaction mixture was filtered to remove the resin which was then washed with further DMF/DCM (3:1). The filtrate was concentrated to give the crude product which was purified by column chromatography. Elution with an ether/pentane gradient yielded the title compound (0.055 g). MS (ES): MH+ 501.2.

Tabulated compounds D138-D140 were prepared from dimethylethyl (2S)-2-methyl-4-{[4-(methylamino)phenyl]methyl}-1-piperazinecarboxylate (D3) and the appropriate carboxylic acid using methods similar to that described in for D137 in Description 137.

| Description | Structure | Name | MH+ |
|---|---|---|---|
| D138 | 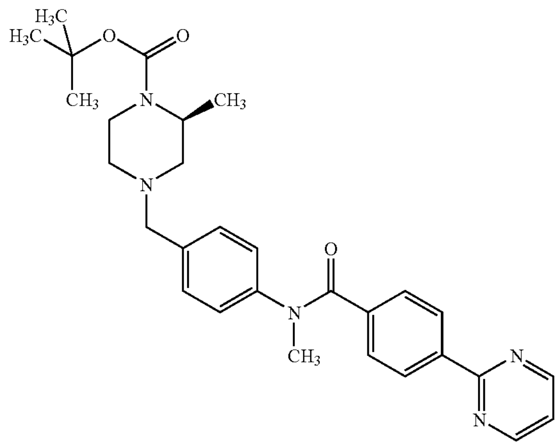 | 1,1-dimethylethyl (2S)-2-methyl-4-{[4-(methyl{[4-(2-pyrimidinyl)phenyl]carbonyl}amino)phenyl]methyl}-1-piperazinecarboxylate | 502.2 |
| D139 | 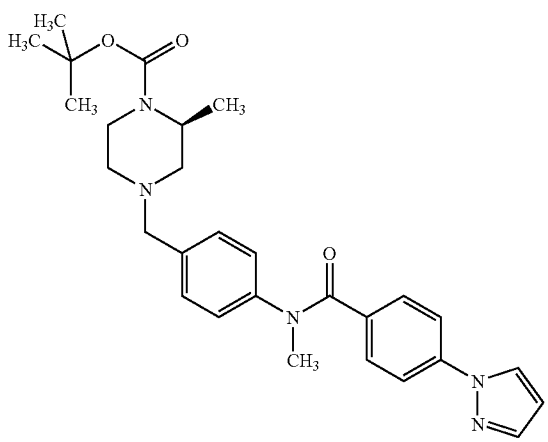 | 1,1-dimethylethyl (2S)-2-methyl-4-{[4-(methyl{[4-(1H-pyrazol-1-yl)phenyl]carbonyl}amino)phenyl]methyl}-1-piperazinecarboxylate | 490.4 |
| D140 | 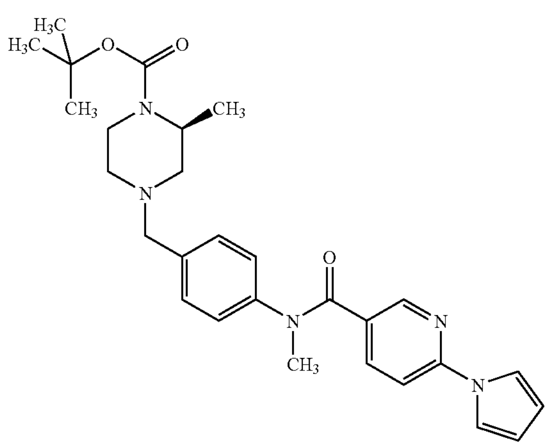 | 1,1-dimethylethyl (2S)-2-methyl-4-{[4-(methyl{[6-(1H-pyrrol-1-yl)-3-pyridinyl]carbonyl}amino)phenyl]methyl}-1-piperazinecarboxylate | 490.4 |

Description 141

1,1-Dimethylethyl (2S)-2-methyl-4-{[4-(methyl{[4-(3-methyl-1,2,4-oxadiazol-5-yl)phenyl]carbonyl}amino)phenyl]methyl}-1-piperazinecarboxylate (D141)

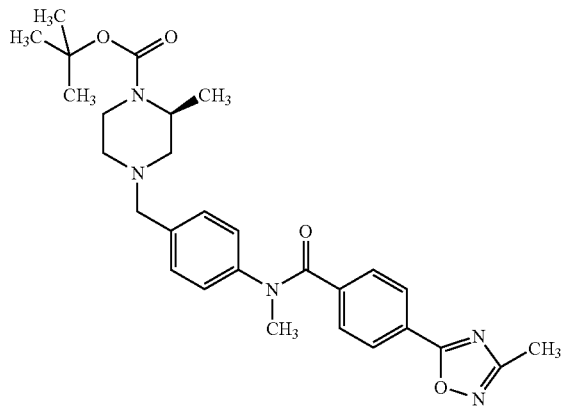

To 1,1-dimethylethyl (2S)-2-methyl-4-{[4-(methylamino)phenyl]methyl}-1-piperazinecarboxylate (D3) (100 mg, 0.313 mmol) in DMF (3 mL) was N-benzyl-N'-cyclohexylcarbodiimide resin (0.294 g, 1.6 mmol/g, 0.47 mmol), 1-hydroxybenzotriazole (0.064 g, 0.47 mmol) and DCM (1 mL). The mixture was stirred for 30 minutes and 4-(3-methyl-1,2,4-oxadiazol-5-yl)benzoic acid (0.064 g, 0.313 mmol), DCM (2 mL) and DMF (6 mL) were added. The reaction mixture was stirred for 22 h at room temperature. PS-trisamine resin (0.179 g, 0.626 mmol), PS-isocyanate resin (0.298 g, 0.626 mmol) and MP-carbonate resin (0.788 g, 2.35 mmol) were added and the mixture stirred for 2 h at room temperature. The mixture was filtered to remove the resins and the filtrate was concentrated to give the crude product which was purified by column chromatography. Elution with 10-60% EtOAc/pentane gave the title compound. MS (ES): MH+ 506.2.

EXAMPLE 1

6-(3-Fluorophenyl)-N-methyl-N-(4-{[(3S)-3-methyl-1-piperazinyl]methyl}phenyl)-3-pyridinecarboxamide (E1)

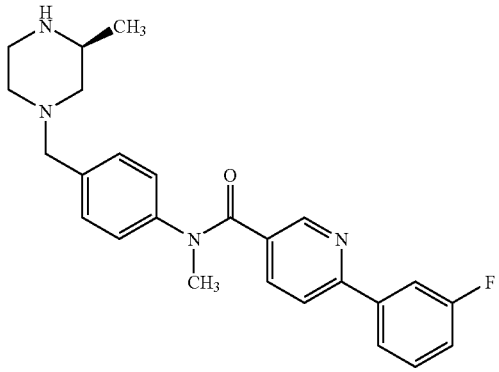

1,1-Dimethylethyl (2S)-4-({4-[{[6-(3-fluorophenyl)-3-pyridinyl]carbonyl}(methyl)amino]phenyl}methyl)-2-methyl-1-piperazinecarboxylate (D60) (0.127 g, 0.245 mmol) was stirred in DCM (10 mL) and TFA (2.5 mL) was added drop-wise. The reaction mixture was stirred for ~1 h, then concentrated in vacuo and re-diluted with DCM and water. The separated aqueous layer was basified to pH14 with concentrated NaOH solution, then extracted with DCM which was dried (Na$_2$SO$_4$) and concentrated to yield the title compound as a yellow oil (0.091 g). δ$_H$ (CDCl$_3$, 400 MHz) 8.52 (1H, d), 7.75 (1H, dd), 7.67 (2H, m), 7.54 (1H, d), 7.40 (1H, m), 7.25 (2H, d), 7.09 (1H, m), 7.03 (2H, d), 3.53 (3H, s), 3.41 (2H, s), 2.83 (3H, m), 2.66 (2H, d), 1.96 (1H, td), 1.62 (1H, m), 1.55 (br.s), 0.97 (3H, d), NH not observed. MS (ES): MH+ 419.2.

This whole was dissolved in MeOH and treated with 1M HCl in Et$_2$O (0.218 mL) to give the hydrochloride salt of the title compound as an off-white solid (0.092 g). MS (ES): MH+ 419.2.

EXAMPLE 2

6-[(4-Fluorophenyl)oxy]-N-methyl-N-(4-{[(3S)-3-methyl-1-piperazinyl]methyl}phenyl)-3-pyridinecarboxamide (E2)

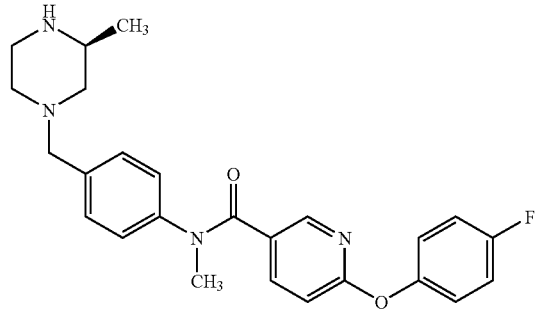

1,1-Dimethylethyl (2S)-4-({4-[({6-[(4-fluorophenyl)oxy]-3-pyridinyl}carbonyl)(methyl)amino]phenyl}methyl)-2-methyl-1-piperazinecarboxylate (D16) (0.518 g, 0.97 mmol) was dissolved in DCM (19.2 mL) and TFA (4.8 mL) added. The solution was stirred for 1.5 h then the solvent was removed in vacuo. The product was taken up in methanol and eluted through an SCX (10 g) column with 2M NH$_3$ in methanol solution. The solvent was removed to give a colourless oil which was purified by column chromatography. Elution with a 0-5% (2M NH$_3$ in methanol)/DCM gradient yielded the title compound as a colourless oil (0.379 g). δ$_H$ (CDCl$_3$, 400 MHz) 8.07 (1H, dd), 7.65 (1H, dd), 7.22 (2H, d), 7.04 (6H, m), 6.70 (1H, d), 3.48 (3H, s), 3.43 (2H, s), 3.13 (br.s), 2.95 (3H, m), 2.70 (2H, d), 2.04 (1H, m), 1.74 (1H, m), 1.05 (3H, d). MS (ES): MH+ 435.3.

This whole was dissolved in DCM and treated with 1M HCl in Et$_2$O (0.873 mL) to give the hydrochloride salt of the title compound as a pale cream solid (0.345 g). MS (ES): MH+ 435.2.

EXAMPLE 2

Alternative Method (A)

6-[(4-Fluorophenyl)oxy]-N-methyl-N-(4-{[(3S)-3-methyl-1-piperazinyl]methyl}phenyl)-3-pyridinecarboxamide (E2)

A solution of 1,1-dimethylethyl (2S)-4-({4-[({6-[(4-fluorophenyl)oxy]-3-pyridinyl}carbonyl)(methyl)amino]phenyl}methyl)-2-methyl-1-piperazinecarboxylate (D16) (32.39 g, 0.0606 mol) in DCM (150 mL) was cooled in an ice/water bath and TFA (80 mL) was added drop-wise over 10 minutes. The reaction mixture was stirred at room temperature overnight then concentrated to a yellow gum. The gum was dissolved in MeOH (100 mL) and loaded onto SCX resin (150 g, pre-washed with MeOH). Elution with MeOH (750 mL) gave unchanged TFA salt of the title compound, and elution with 2M $NH_3$ in MeOH (750 mL) gave title compound free base. The recovered TFA salt was treated in a similar manner to that described above using further SCX resin (100 g) to give a further batch of title compound free base. The two batches of the free base were combined in DCM and concentrated to give the title compound as a pale yellow gum (26.78 g). $\delta_H$ ($CDCl_3$, 400 MHz) 8.07 (1H, d), 7.65 (1H, dd), 7.22 (2H, d), 7.04 (6H, m), 6.70 (1H, d), 3.48 (3H, s), 3.42 (2H, s), 2.89 (3H, m), 2.68 (2H, d), 1.97 (1H, m), 1.64 (1H, t), 1.49 (1H bs), 1.00 (3H, d). MS (ES): $MH^+$ 435.1.

A solution of E2 free base (25.74 g, 0.0592 mol) was dissolved in MeOH (250 mL) at room temperature, flushed with argon was treated with 1M HCl in $Et_2O$ (59.2 mL). The solution was concentrated in vacuo to give a pale brown foam which was dried overnight at 60° C. in vacuo. 26.4 g of this material was dissolved in DCM (175 mL) and added dropwise over 30 minutes to vigorously stirred hexane (2.65 L) under an argon atmosphere. Stirring was discontinued and the precipitate was isolated by filtration under argon, washed with hexane (2×2 L), filtered under a gentle vacuum with an argon blanket and then dried in vacuo at 80° C. overnight. The resulting solid was dissolved in water (220 mL), freeze-dried over-weekend, ground to a powder and dried in vacuo at 80-82° C. overnight. The powder was re-dissolved in water (150 mL), freeze-dried overnight and then ground to a powder yielding the hydrochloride salt of the title compound as a cream solid (24.13 g)

EXAMPLE 2B

Method 1

6-[(4-Fluorophenyl)oxy]-N-methyl-N-(4-{[(3S)-3-methyl-1-piperazinyl]methyl}phenyl)-3-pyridinecarboxamide fumarate (E2B)

A solution of E2 free base (57.5 mg) in methyl iso-butylketone (0.5 mL) was added to fumaric acid (13.4 mg). Further methyl iso-butylketone (0.5 mL) was added and the mixture was heated with a hot air gun. The resulting yellow gum was scratched with a spatula and a small amount of white solid appeared throughout the gum. The sample was placed on a shaker block and temperature cycled (0-40° C. in 1 h blocks) over the weekend. To the resulting yellow gum in a colourless solution was added 1,4-dioxane (0.5 mL) and the mixture was heated to dissolve the gum. On cooling a gum formed and the sample was temperature cycled as before. After a period of ~6 weeks a white solid slurry had formed. The mixture was placed back in the shaker block and temperature cycled as before, overnight. The mixture was then left to equilibrate to room temperature and the white solid was collected by filtration. After drying at 40° C. under vacuum overnight the title compound was obtained as a white, mainly crystalline powder (38.7 mg). M.pt. onset ~150° C.

EXAMPLE 2B

Method 2

6-[(4-Fluorophenyl)oxy]-N-methyl-N-(4-{[(3S)-3-methyl-1-piperazinyl]methyl}phenyl)-3-pyridinecarboxamide fumarate (E2B)

A mixture of E2 free base (413.7 mg) and fumaric acid (107.4 mg) in methyl iso-butylketone (8 mL) and 1,4-dioxane (4 mL) was heated with a hot air gun giving a yellow solution. On cooling, a white gummy precipitate formed so the mixture was re-heated to dissolve the gum and then seeded with the previously obtained fumarate salt from Method 1. On cooling, a gum formed so further 1,4-dioxane (2 mL) was added and the mixture heated to dissolve the gum. Further seeds were added at ~60° C. and the mixture was temperature cycled (0-40° C. in 1 h blocks but starting at 40° C.) over the weekend. To the resulting 'milk-like' slurry was added further 1,4-dioxane (1.5 mL), the sides of the vessel were scratched and the mixture was then temperature cycled as before. After 9 days, the slurry was filtered and the filter cake was de-liquored over ~90 minutes to give a white solid which was dried at 40° C. under vacuum. After 20 h the title compound was obtained as white, mainly crystalline, powder (377.2 mg).

Thermal Analysis

The DSC thermogram of the product was obtained using a TA Q1000 calorimeter, serial number 1000-0126. The sample was weighed into an aluminium pan, a pan lid placed on top and lightly crimped without sealing the pan. The experiment was conducted using a heating rate of 10° C. $min^{-1}$. Melt onset 141° C.

X-Ray Powder Diffraction (XRPD)

The XRPD data were acquired on a PANalytical X'Pert Pro powder diffractometer, model PW3040/60, serial number DY1850 using an XCelerator detector. The acquisition conditions were: radiation: Cu Kα, generator tension: 40 kV, generator current: 45 mA, start angle: 2.0.°2.θ, end angle: 40.0°2θ, step size: 0.0167°2θ, time per step: 31.75 seconds. The sample was prepared by mounting a few milligrams of sample on a Si wafer (zero background) plates, resulting in a thin layer of powder. Characteristic XRPD angles and d-spacings are recorded in the table below.

Peak positions were measured using Highscore software.

| Characteristic XRPD peak positions 2θ/° | d-spacing/Å |
| --- | --- |
| 4.5 | 19.5 |
| 8.9 | 10.0 |
| 9.8 | 9.0 |
| 12.2 | 7.3 |
| 13.0 | 6.8 |
| 14.6 | 6.1 |
| 16.0 | 5.6 |
| 16.7 | 5.3 |
| 17.7 | 5.0 |
| 18.9 | 4.7 |
| 20.2 | 4.4 |
| 21.1 | 4.2 |
| 22.1 | 4.0 |
| 23.5 | 3.8 |
| 24.1 | 3.7 |
| 25.2 | 3.5 |
| 26.3 | 3.4 |
| 27.0 | 3.3 |

EXAMPLE 2B

Method 3

6-[(4-Fluorophenyl)oxy]-N-methyl-N-(4-{[(3S)-3-methyl-1-piperazinyl]methyl}phenyl)-3-pyridinecarboxamide fumarate (E2B)

A mixture of E2 free base (201.9 mg) and fumaric acid (53.9 mg) in EtOAc (2 mL) was stirred at room temperature. After 5 minutes, a milky gelatinous precipitate started to form so further EtOAc (2 mL) was added together with seed crystals of the previously obtained fumarate salt from Method 2. After 1 h, the precipitate became very thick and gelatinous so further EtOAc (2 ml) and seed crystals were added. The mixture was stirred at room temperature for 0.5 h, then warmed to 40° C. for 0.5 h. Further EtOAc (5 mL) was added and stirring was continued at 40° C. for 10 minutes then at 60° C. for 2 h. The mixture was cooled to 50° C. for 1 h then to 40° C. for 1 h then to room temperature overnight. The solid was filtered off under argon, washed with EtOAc, semi-dried under argon and then dried at 60° C. under vacuum to give the title compound (164 mg).

EXAMPLE 2B

Method 4

6-[(4-Fluorophenyl)oxy]-N-methyl-N-(4-{[(3S)-3-methyl-1-piperazinyl]methyl}phenyl)-3-pyridinecarboxamide fumarate (E2B)

A partial suspension/solution of finely ground fumaric acid (267 mg) in EtOAc (10 mL) was stirred and heated at 60° C. This was added portion-wise to a solution of E2 free base (0.9997 g) in EtOAc (20 ml) heated at 70° C. Any initial turbidity/gum rapidly disappeared but as addition continued the solution stayed slightly turbid. At this point the solution was seeded with the previously obtained fumarate salt from Method 3 and within a few minutes a heavy crystalline precipitate started to form. Addition of the fumaric acid suspension/solution continued over ~3 h. The reaction mixture was stirred at 70° C. for a further one hour then slowly allowed to cool to room temperature overnight with stirring. The solid was collected by filtration, washed with EtOAc, dried under argon then further dried at 60° C., under vacuum, overnight to give the title compound (1.077 g). $\delta_H$ (CD$_3$OD, 400 MHz) 7.95 (1H, d), 7.74 (1H, dd), 7.31 (2H, d), 7.17 (2H, d), 7.14 (2H, t), 7.05 (2H, dd), 6.78 (1H, d), 6.68 (2H, s), 3.56 (2H, s), 3.46 (3H, s), 3.30 (2H+MeOH, m), 3.11 (1H, m), 2.89 (2H, m), 2.32 (1H, m), 2.10 (1H, dd), 1.25 (3H, d) (NH not observed).

Thermal Analysis

The DSC thermogram of the product was obtained using a TA Q1000 calorimeter, serial number Q1000-0264. The sample was weighed into an aluminium pan, a pan lid placed on top and lightly crimped without sealing the pan. The experiment was conducted using a heating rate of 10° C. min$^{-1}$. Melt onset 153° C.

X-Ray Powder Diffraction (XRPD)

XRPD data for Example 2B: Method 4 were acquired on a PANalytical X'Pert MPD powder diffractometer, model PW3040/60, serial number DY667 using an XCelerator detector. The acquisition conditions were: radiation: Cu Kα, generator tension: 40 kV, generator current: 45 mA, start angle: 2. °θ, end angle: 40.0°2θ, step size: 0.0167°2 θ, time per step: 48.26 seconds. The sample was prepared by mounting a few milligrams of sample on a Si wafer (zero background) plates, resulting in a thin layer of powder. Characteristic XRPD angles and d-spacings are recorded in the table below. Peak positions were measured using Highscore software.

| Characteristic XRPD peak posisitions 2θ/° | d-spacing/Å |
|---|---|
| 9.0 | 9.9 |
| 9.7 | 9.1 |
| 12.2 | 7.2 |
| 13.7 | 6.5 |
| 15.4 | 5.7 |
| 15.8 | 5.6 |
| 16.1 | 5.5 |
| 16.7 | 5.3 |
| 17.1 | 5.2 |
| 18.0 | 4.9 |
| 18.3 | 4.9 |
| 19.1 | 4.6 |
| 19.4 | 4.6 |
| 19.7 | 4.5 |
| 20.3 | 4.4 |
| 20.9 | 4.3 |
| 22.5 | 4.0 |
| 22.9 | 3.9 |
| 25.2 | 3.5 |
| 25.6 | 3.5 |

EXAMPLE 2B

Method 5

6-[(4-Fluorophenyl)oxy]-N-methyl-N-(4-{[(3S)-3-methyl-1-piperazinyl]methyl}phenyl)-3-pyridinecarboxamide fumarate (E2B)

A suspension of finely ground fumaric acid (13.84 g) in EtOAc (500 mL) was stirred and heated at 70° C. This was added portion-wise to a stirred solution of E2 free base (57.80 g) in EtOAc (1 L) heated at 70° C. When ~80-100 mL of the fumaric acid suspension had been added, the solution was seeded with previously obtained fumarate salt (40 mg) (prepared using a method similar to that described in Example 2B, Method 4). To the resulting faintly turbid solution was added further fumaric acid suspension (~50 mL) giving a cloudy solution. On addition of further seeds (40 mg), crystallization started. Addition of the remaining fumaric acid suspension in 8-10 mL portions continued over ~4 h. Further EtOAc (~30 mL) was used to aid transfer of the final solid residues of fumaric acid to the reaction vessel. The reaction mixture was stirred at 70° C. for a further 4 h then slowly allowed to cool to room temperature overnight with stirring. The crystalline solid was collected by filtration, washed with EtOAc and dried under argon; then further dried under vacuum at 60° C. overnight to give the title compound (60.8 g).

$\delta_H$ (CD$_3$OD, 400 MHz) 7.95 (1H, d), 7.74 (1H, dd), 7.31 (2H, d), 7.17 (2H, d), 7.13 (2H, t), 7.05 (2H, dd), 6.78 (1H, d), 6.68 (2H, s), 3.56 (2H, s), 3.46 (3H, s), 3.30 (2H+MeOH, m), 3.11 (1H, m), 2.89 (2H, m), 2.32 (1H, m), 2.10 (1H, dd), 1.25 (3H, d) (NH not observed).

$\delta_H$ (DMSO-d$_6$, 400 MHz) 7.97 (1H, d), 7.65 (1H, dd), 7.16-7.25 (6H, m), 7.10 (2H, dd), 6.87 (1H, d), 6.46 (2H, s), 3.45 (2H, s), 3.36 (3H, s), 3.08 (2H, m), 2.85 (1H, m), 2.68 (2H, m), 2.16 (1H, m), 1.93 (1H, m), 1.09 (3H, d) (NH not observed). MS (ES): MH$^+$ 435.3

EXAMPLE 3

1-(4-Fluorophenyl)-N-methyl-N-(4-{[(3S)-3-methyl-1-piperazinyl]methyl}phenyl)-4-piperidinecarboxamide (E3)

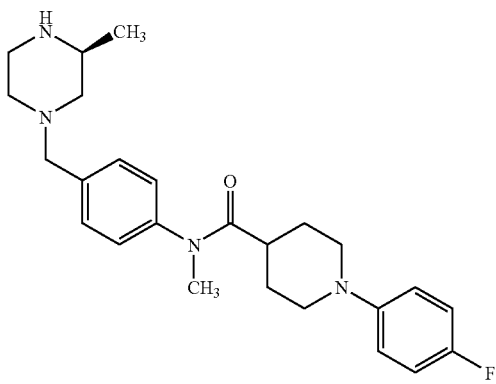

To 1,1-dimethylethyl (2S)-4-({4-[{[1-(4-fluorophenyl)-4-piperidinyl]carbonyl}(methyl)amino]phenyl}methyl)-2-methyl-1-piperazinecarboxylate (D59) (0.19 g, 0.36 mmol) in DCM (5 mL), cooled in an ice bath, was added TFA (1.5 mL) and the reaction mixture was then stirred for 3 h at room temperature. The solvent was removed and the crude product was eluted through an SCX cartridge with methanol then 2M $NH_3$ in methanol to give a yellow oil which was further purified by column chromatography. Elution with 0-5% (2M $NH_3$ in methanol)/DCM yielded the title compound as a yellow oil (0.13 g). $\delta_H$ (MeOD, 250 MHz) 7.48 (2H, d), 7.30 (2H, d), 7.13 (2H, d), 6.84 (2H, d), 3.59 (4H, m), 3.23 (3H, s), 3.18 (2H, d), 3.01 (1H, m), 2.90 (2H, t), 2.31 (4H, m), 2.02 (1H, m), 1.85 (2H, m), 1.70 (2H, d), 1.17 (3H, d) [NH not observed]. MS (ES): $MH^+$ 425.2.

This whole was dissolved in DCM and treated with 1M HCl in $Et_2O$ (0.337 mL) to give the hydrochloride salt of the title compound as a white solid (0.1 g). MS (ES): $MH^+$ 425.1

The following tabulated examples E4-E37 were prepared from the appropriate Boc-protected intermediate as indicated in the table, using methods similar to those described for Example 1, 2 or 3.

| Example No. | Prepared from Boc intermediate: | Structure | Name | Method Comment | MH+ |
|---|---|---|---|---|---|
| E4 | D61 | 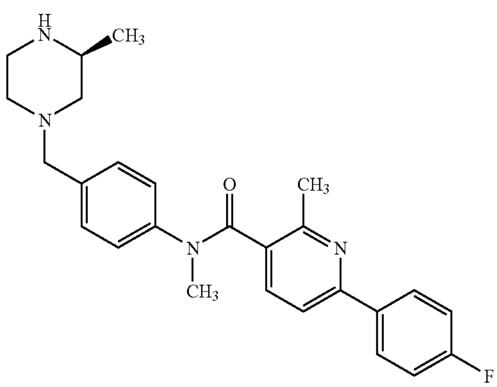 | 6-(4-fluorophenyl)-N,2-dimethyl-N-(4-{[(3S)-3-methyl-1-piperazinyl]methyl}phenyl)-3-pyridinecarboxamide | Similar method to E1 | 433.2 |
| E5 | D17 | 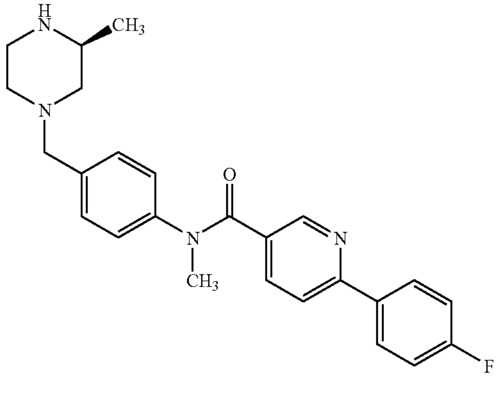 | 6-(4-fluorophenyl)-N-methyl-N-(4-{[(3S)-3-methyl-1-piperazinyl]methyl}phenyl)-3-pyridinecarboxamide | Similar method to E1 with column chromatography | 419.1 |

-continued

| Example No. | Prepared from Boc intermediate: | Structure | Name | Method Comment | MH+ |
|---|---|---|---|---|---|
| E6 | D18 | 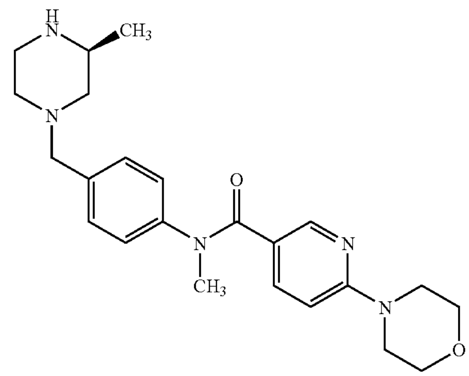 | N-methyl-N-(4-{[(3S)-3-methyl-1-piperazinyl]methyl}phenyl)-6-(4-morpholinyl)-3-pyridinecarboxamide | Similar method to E1 | 410.3 |
| E7 | D19 | 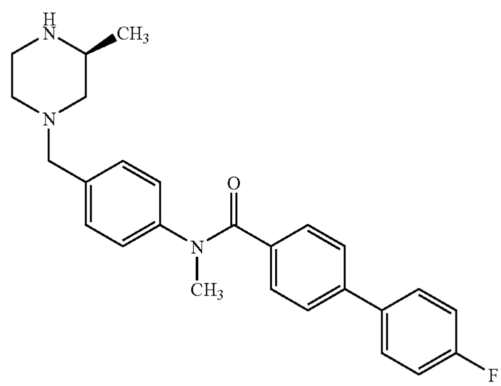 | 4'-fluoro-N-methyl-N-(4-{[(3S)-3-methyl-1-piperazinyl]methyl}phenyl)-4-biphenylcarboxamide | Similar method to E1 | 418.3 |
| E8 | D20 | 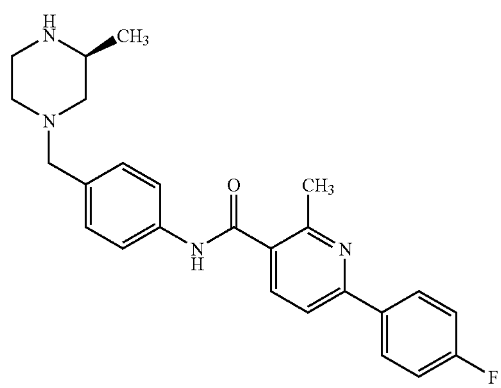 | 6-(4-fluorophenyl)-2-methyl-N-(4-{[(3S)-3-methyl-1-piperazinyl]methyl}phenyl)-3-pyridinecarboxamide | Similar method to E1 with reaction time of ~2.3 h | 419.3 |
| E9 | D21 | 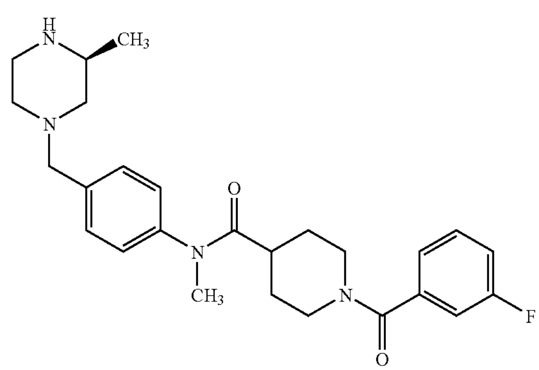 | 1-[(3-fluorophenyl)carbonyl]-N-methyl-N-(4-{[(3S)-3-methyl-1-piperazinyl]methyl}phenyl)-4-piperidinecarboxamide | Similar method to E1 | 453.2 |

-continued

| Example No. | Prepared from Boc intermediate: | Structure | Name | Method Comment | MH+ |
|---|---|---|---|---|---|
| E10 | D22 | 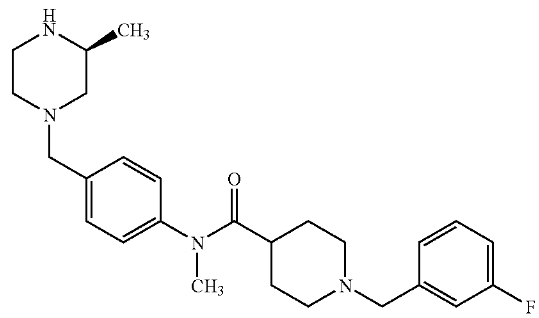 | 1-[(3-fluorophenyl)methyl]-N-methyl-N-(4-{[(3S)-3-methyl-1-piperazinyl]methyl}phenyl)-4-piperidinecarboxamide | Similar method to E1 with column chromatography | 439.3 |
| E11 | D23 | 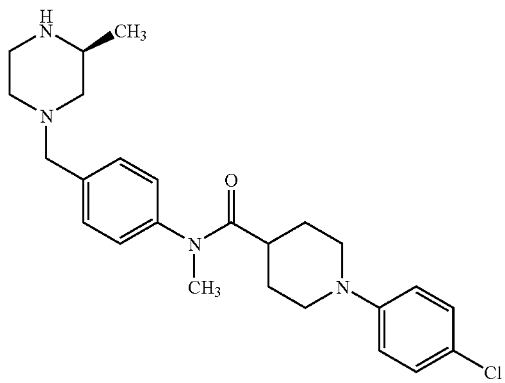 | 1-(4-chlorophenyl)-N-methyl-N-(4-{[(3S)-3-methyl-1-piperazinyl]methyl}phenyl)-4-piperidinecarboxamide | Similar method to E3 but no column chromatography | 441.1 |
| E12 | D24 | 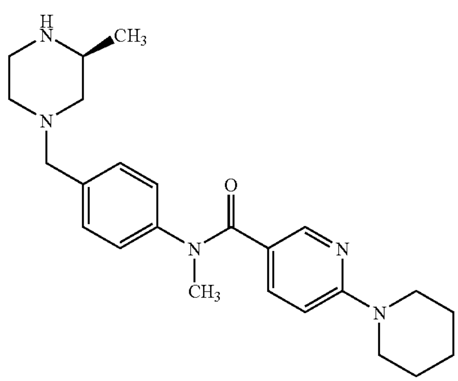 | N-methyl-N-(4-{[(3S)-3-methyl-1-piperazinyl]methyl}phenyl)-6-(1-piperidinyl)-3-pyridinecarboxamide | Similar method to E1 with reaction time of 3.5 h and column chromatography | 408.3 |
| E13 | D25 | 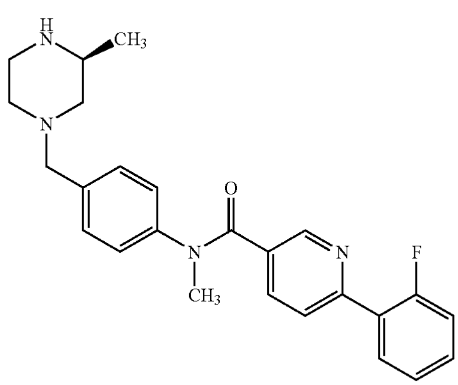 | 6-(2-fluorophenyl)-N-methyl-N-(4-{[(3S)-3-methyl-1-piperazinyl]methyl}phenyl)-3-pyridinecarboxamide | Similar method to E1 | 419.2 |

-continued

| Example No. | Prepared from Boc intermediate: | Structure | Name | Method Comment | MH+ |
|---|---|---|---|---|---|
| E14 | D26 | 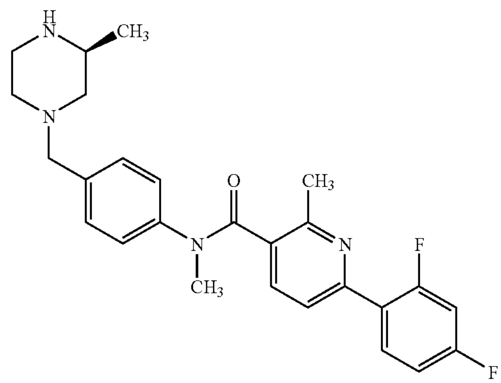 | 6-(2,4-difluorophenyl)-N,2-dimethyl-N-(4-{[(3S)-3-methyl-1-piperazinyl]methyl}phenyl)-3-pyridinecarboxamide | Similar method to E1 with column chromatography | 451.2 |
| E15 | D27 | 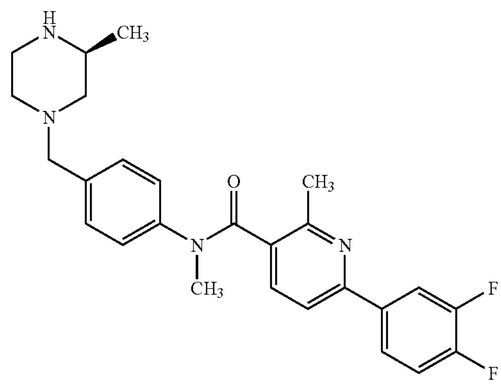 | 6-(3,4-difluorophenyl)-N,2-dimethyl-N-(4-{[(3S)-3-methyl-1-piperazinyl]methyl}phenyl)-3-pyridinecarboxamide | Similar method to E1 with column chromatography | 451.2 |
| E16 | D28 | 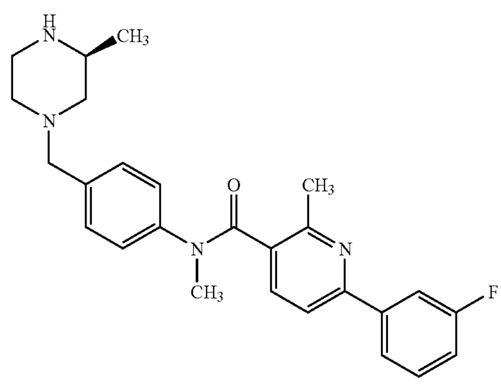 | 6-(3-fluorophenyl)-N,2-dimethyl-N-(4-{[(3S)-3-methyl-1-piperazinyl]methyl}phenyl)-3-pyridinecarboxamide | Similar method to E1 with column chromatography | 433.2 |
| E17 | D29 | 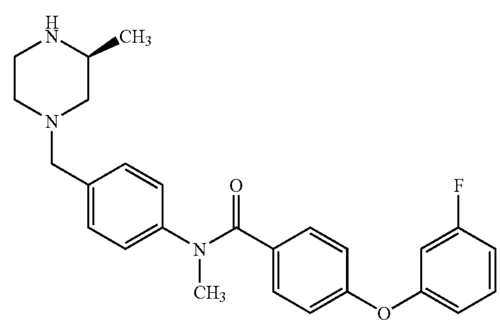 | 4-[(3-fluorophenyl)oxy]-N-methyl-N-(4-{[(3S)-3-methyl-1-piperazinyl]methyl}phenyl)benzamide | Similar method to E3 with reaction time of 2 h and no column chromatography | 434.1 |

-continued

| Example No. | Prepared from Boc intermediate: | Structure | Name | Method Comment | MH+ |
|---|---|---|---|---|---|
| E18 | D30 | 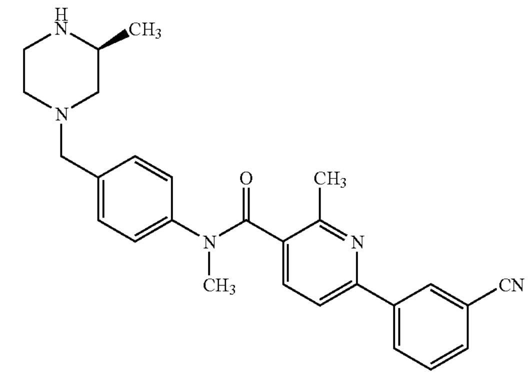 | 6-(3-cyanophenyl)-N,2-dimethyl-N-(4-{[(3S)-3-methyl-1-piperazinyl]methyl}phenyl)-3-pyridinecarboxamide | Similar method to E1 with column chromatography | 440.3 |
| E19 | D31 | 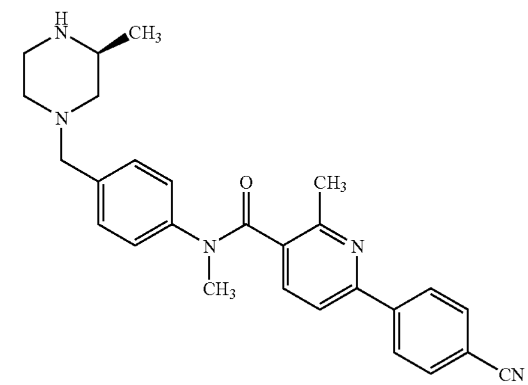 | 6-(4-cyanophenyl)-N,2-dimethyl-N-(4-{[(3S)-3-methyl-1-piperazinyl]methyl}phenyl)-3-pyridinecarboxamide | Similar method to E1 with column chromatography | 440.3 |
| E20 | D32 | 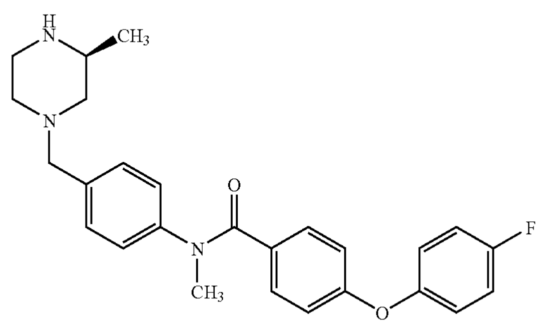 | 4-[(4-fluorophenyl)oxy]-N-methyl-N-(4-{[(3S)-3-methyl-1-piperazinyl]methyl}phenyl)benzamide | Similar method to E3 with reaction time of 3.5 h and no column chromatography | 434.1 |
| E21 | D15 | 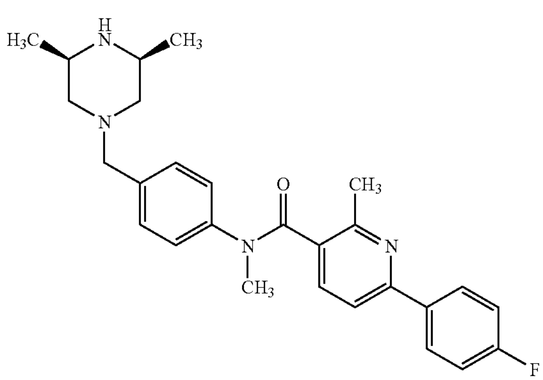 | N-(4-{[(3R,5S)-3,5-dimethyl-1-piperazinyl]methyl}phenyl)-6-(4-fluorophenyl)-N,2-dimethyl-3-pyridinecarboxamide | Similar method to E2 | 447.3 |

-continued

| Example No. | Prepared from Boc intermediate: | Structure | Name | Method Comment | MH+ |
|---|---|---|---|---|---|
| E22 | D33 | 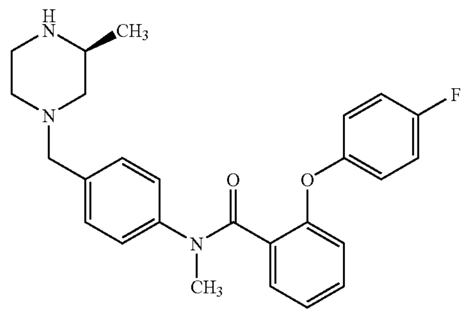 | 2-[(4-fluorophenyl)oxy]-N-methyl-N-(4-{[(3S)-3-methyl-1-piperazinyl]methyl}phenyl)benzamide | Similar method to E3 with reaction time of 3.5 h | 434.1 |
| E23 | D34 | 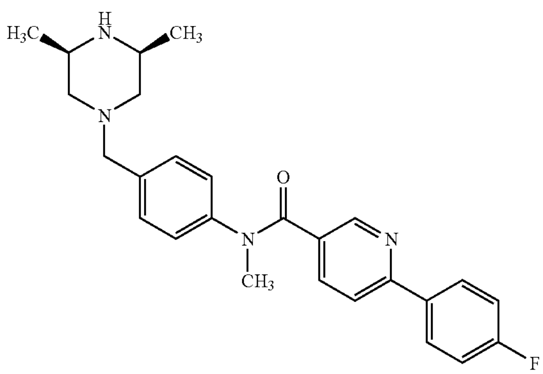 | N-(4-{[(3R,5S)-3,5-dimethyl-1-piperazinyl]methyl}phenyl)-6-(4-fluorophenyl)-N-methyl-3-pyridinecarboxamide | Similar method to E2 with reaction time of 2 h | 433.2 |
| E24 | D35 | 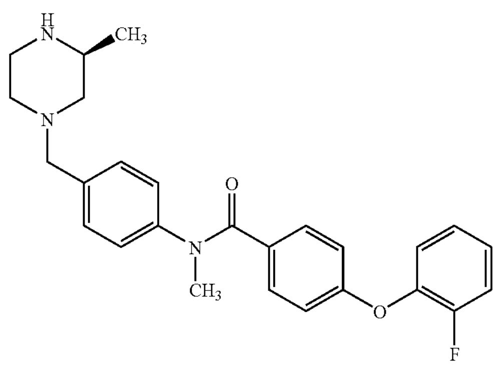 | 4-[(2-fluorophenyl)oxy]-N-methyl-N-(4-{[(3S)-3-methyl-1-piperazinyl]methyl}phenyl)benzamide | Similar method to E3 with reaction time of 5 h and no column chromatography | 434.2 |
| E25 | D36 | 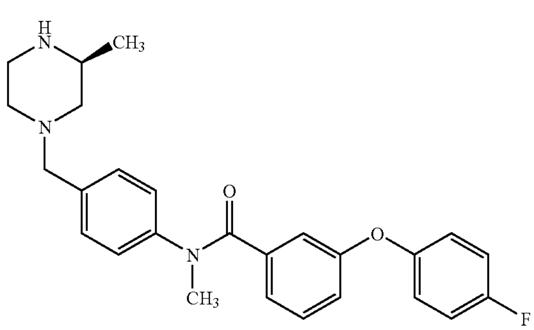 | 3-[(4-fluorophenyl)oxy]-N-methyl-N-(4-{[(3S)-3-methyl-1-piperazinyl]methyl}phenyl)benzamide | Similar method to E3 with reaction time of 5 h and no column chromatography | 434.2 |

-continued

| Example No. | Prepared from Boc intermediate: | Structure | Name | Method Comment | MH+ |
|---|---|---|---|---|---|
| E26 | D37 | 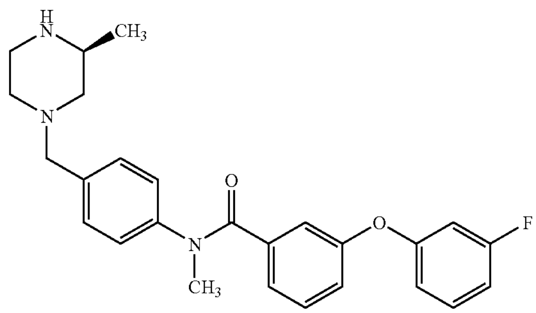 | 3-[(3-fluorophenyl)oxy]-N-methyl-N-(4-{[(3S)-3-methyl-1-piperazinyl]methyl}phenyl)benzamide | Similar method to E3 with reaction time of 1.5 h and no column chromatography | 434.2 |
| E27 | D58 | 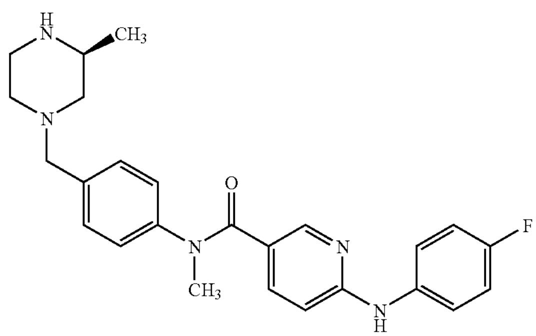 | 6-[(4-fluorophenyl)amino]-N-methyl-N-(4-{[(3S)-3-methyl-1-piperazinyl]methyl}phenyl)-3-pyridinecarboxamide | Similar method to E2 but no column chromatography | 434.2 |
| E28 | D38 | 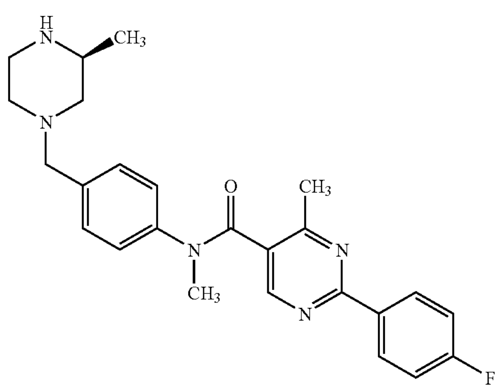 | 2-(4-fluorophenyl)-N,4-dimethyl-N-(4-{[(3S)-3-methyl-1-piperazinyl]methyl}phenyl)-5-pyrimidinecarboxamide | Similar method to E1 with reaction time of 1.5 h and column chromatography | 434.3 |
| E29 | D39 | 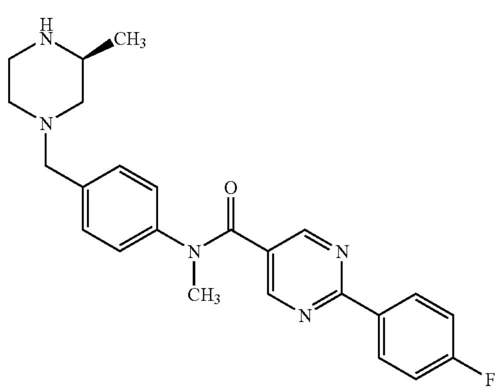 | 2-(4-fluorophenyl)-N-methyl-N-(4-{[(3S)-3-methyl-1-piperazinyl]methyl}phenyl)-5-pyrimidinecarboxamide | Similar method to E1 with reaction time of 1.5 h | 420.3 |

-continued

| Example No. | Prepared from Boc intermediate: | Structure | Name | Method Comment | MH+ |
|---|---|---|---|---|---|
| E30 | D40 | 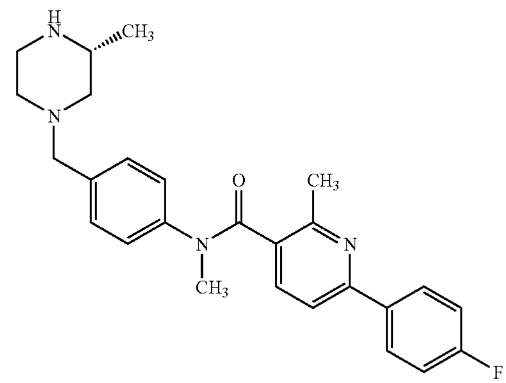 | 6-(4-fluorophenyl)-N,2-dimethyl-N-(4-{[(3R)-3-methyl-1-piperazinyl]methyl}phenyl)-3-pyridinecarboxamide | Similar method to E2 | 433.2 |
| E31 | D41 | 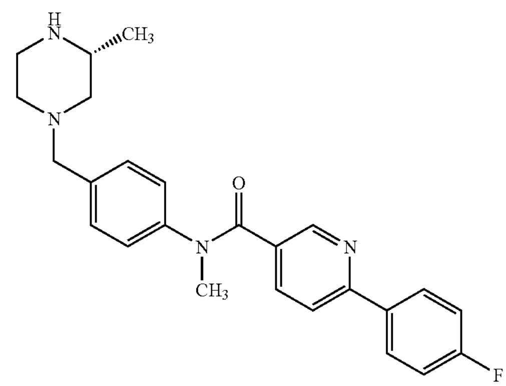 | 6-(4-fluorophenyl)-N-methyl-N-(4-{[(3R)-3-methyl-1-piperazinyl]methyl}phenyl)-3-pyridinecarboxamide | Similar method to E2 with purification by MDAP | 419.2 |
| E32 | D42 | 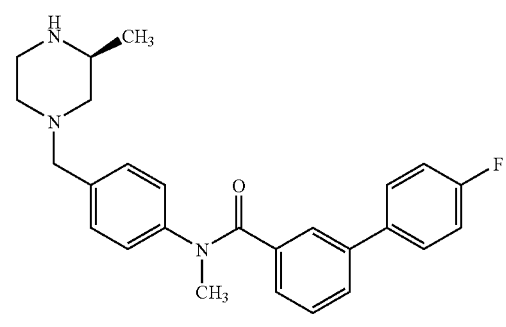 | 4'-fluoro-N-methyl-N-(4-{[(3S)-3-methyl-1-piperazinyl]methyl}phenyl)-3-biphenylcarboxamide | Similar method to E1 with column chromatography | 418.2 |
| E33 | D43 | 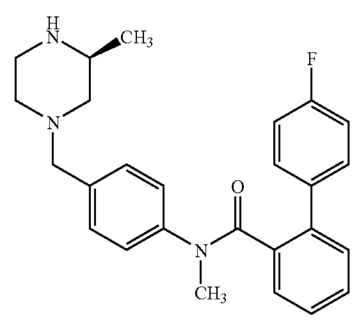 | 4'-fluoro-N-methyl-N-(4-{[(3S)-3-methyl-1-piperazinyl]methyl}phenyl)-2-biphenylcarboxamide | Similar method to E1 with column chromatography | 418 |

-continued

| Example No. | Prepared from Boc intermediate: | Structure | Name | Method Comment | MH+ |
|---|---|---|---|---|---|
| E34 | D45 | 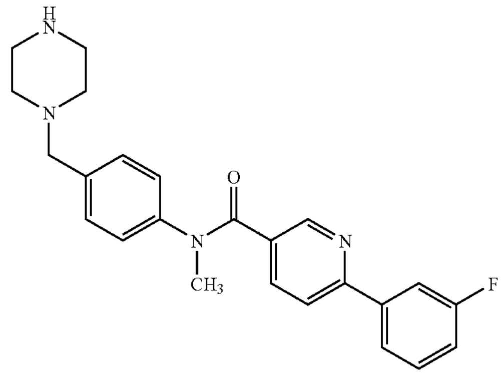 | 6-(3-fluorophenyl)-N-methyl-N-[4-(1-piperazinylmethyl)phenyl]-3-pyridinecarboxamide | Similar method to E2 but no column chromatography | 405.2 |
| E35 | D56 | 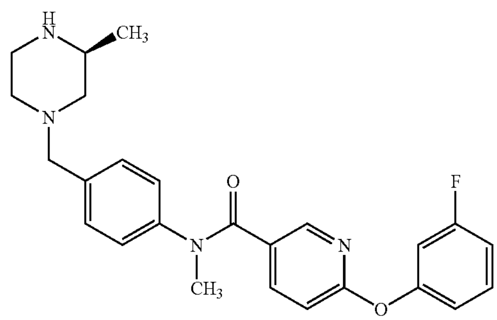 | 6-[(3-fluorophenyl)oxy]-N-methyl-N-(4-{[(3S)-3-methyl-1-piperazinyl]methyl}phenyl)-3-pyridinecarboxamide | Similar method to E2 with reaction time of 1 h and no column chromatography | 435.2 |
| E36 | D55 | 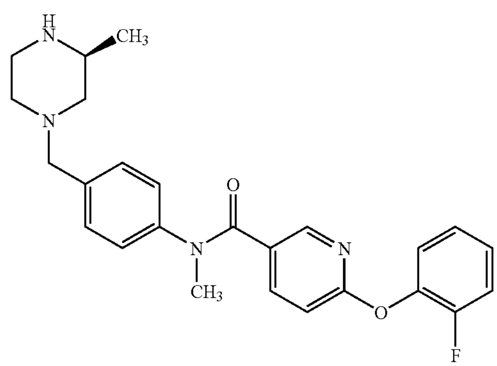 | 6-[(2-fluorophenyl)oxy]-N-methyl-N-(4-{[(3S)-3-methyl-1-piperazinyl]methyl}phenyl)-3-pyridinecarboxamide | Similar method to E2 but no column chromatography | 435.2 |
| E37 | D46 | 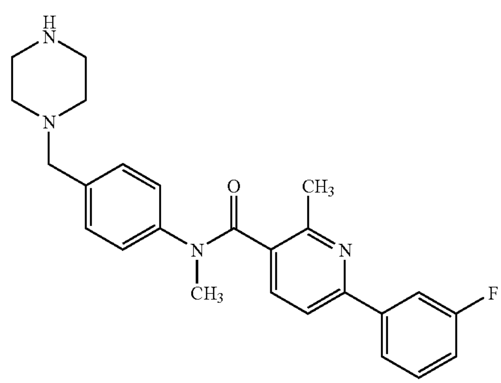 | 6-(3-fluorophenyl)-N,2-dimethyl-N-[4-(1-piperazinylmethyl)phenyl]-3-pyridinecarboxamide | Similar method to E2 but no column chromatography | 419.2 |

EXAMPLE 38 AND EXAMPLE 39

6-(2-Cyanophenyl)-N,2-dimethyl-N-(4-{[(3S)-3-methyl-1-piperazinyl]methyl}phenyl)-3-pyridinecarboxamide (E38)

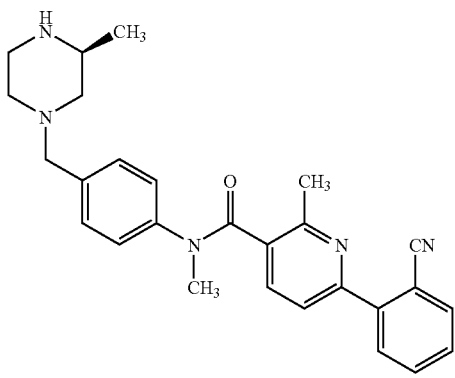

and

6-[2-(Aminocarbonyl)phenyl]-N,2-dimethyl-N-(4-{[(3S)-3-methyl-1-piperazinyl]methyl}phenyl)-3-pyridinecarboxamide (E39)

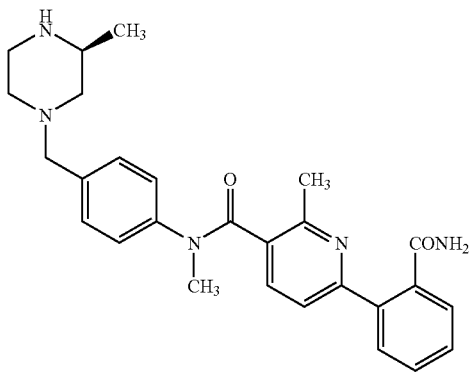

1,1-Dimethylethyl (2S)-4-({4-[{[6-(2-cyanophenyl)-2-methyl-3-pyridinyl]carbonyl}(methyl)amino]phenyl}methyl)-2-methyl-1-piperazinecarboxylate (D44) (0.309 g, 0.573 mmol) was stirred in DCM (20 mL) and TFA (5 mL) was added drop-wise. The reaction mixture was stirred for ~1 h, then concentrated in vacuo and re-diluted with DCM and water. The separated aqueous layer was basified to pH14 with concentrated NaOH solution, then extracted with DCM which was dried (Na$_2$SO$_4$) and concentrated to give the crude product which was purified by column chromatography. Elution with 0-10% MeOH/DCM yielded E38 as a pink oil (0.219 g). MS (ES): MH$^+$ 440.3.

This whole was taken up in MeOH and 1M HCl in Et$_2$O (0.598 mL) added. The solvent was removed to give a crude product mixture which was purified by MDAP to yield the crude formate salts of the title compounds E38 and E39. E38 formate salt was passed through an SCX cartridge eluting with methanol then 2M NH$_3$ in methanol yielding E38 free base (0.051 g) as a white solid. δ$_H$ (CDCl$_3$, 400 MHz) 7.75 (2H, m), 7.64 (1H, m), 7.43 (3H, m), 7.16 (2H, d), 6.98 (2H, d), 3.65 (3H, s), 3.36 (2H, s), 2.83 (3H, m), 2.63 (5H, m), 1.91 (1H, m), 1.59 (1H, m), 1.35 (br.s) 0.95 (3H, d). MS (ES): MH$^+$ 440.3.

E39 formate salt was passed through an SCX cartridge eluting with methanol then 2M NH$_3$ in methanol yielding crude E39 free base (0.026 g) as a colourless oil which was further purified by column chromatography. Elution with 0-10% (2M NH$_3$ in methanol)/DCM yielded E39 free base as a colourless oil (0.024 g). δ$_H$ (MeOH, 400 MHz) 7.50 (5H, br.d), 7.23 (3H, m), 7.16 (2H, m), 3.51 (3H, s), 3.14 (2H, s), 3.35 (3H, s), 2.82 (3H, m), 2.64 (2H, m), 2.51 (3H, s), 1.96 (1H, m), 1.56 (1H, m), 0.95 (3H, d). MS (ES): MH$^+$ 458.1.

E39 free base was dissolved in MeOH and treated with 1M HCl in Et$_2$O (0.058 mL) to give the hydrochloride salt of E39 as a light yellow solid (0.011 g). MS (ES): MH$^+$ 458.1.

EXAMPLE 40

6-(2-Cyanophenyl)-N-methyl-N-(4-{[(3S)-3-methyl-1-piperazinyl]methyl}phenyl)-3-pyridinecarboxamide (E40)

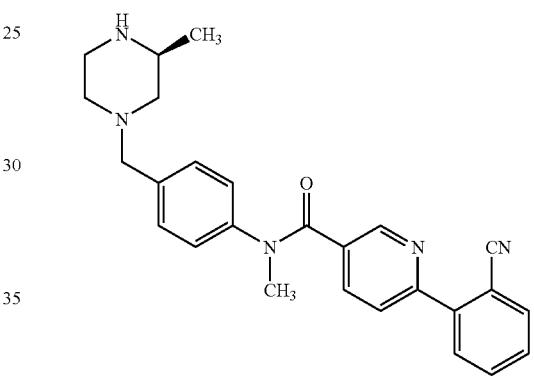

1,1-Dimethylethyl (2S)-4-({4-[{[6-(2-cyanophenyl)-3-pyridinyl]carbonyl}(methyl)amino]phenyl}methyl)-2-methyl-1-piperazinecarboxylate (D49) (0.091 g, 0.173 mmol) was stirred in DCM (10 mL) and TFA (2.5 mL) was added drop-wise. The reaction mixture was stirred for ~1 h, then concentrated in vacuo and re-diluted with DCM and water. The separated aqueous layer was basified to pH14 with concentrated NaOH solution, then extracted with DCM which was dried (Na$_2$SO$_4$) and concentrated to give the crude product which was purified by column chromatography. Elution with 0-10% MeOH/DCM yielded the title compound as a colourless oil (0.054 g). δ$_H$ (CDCl$_3$, 400 MHz) 8.59 (1H, s), 7.83 (1H, dd), 7.78 (2H, m), 7.67 (1H, m), 7.50 (1H, m), 7.23 (2H, d), 7.05 (2H, d), 3.54 (3H, s), 3.45 (2H, s), 2.89-3.02 (3H, m), 2.71 (2H, m), 2.09 (1H, t), 1.79 (1H, t), 1.75 (br.s) 1.07 (3H, d). MS (ES): MH$^+$ 426.2.

The title compound (0.054 g) was dissolved in MeOH (0.54 mL). A portion of this solution (0.20 mL) was treated with 1M HCl in Et$_2$O but this resulted in partial decomposition to the corresponding 2-primary amide compound. The remaining MeOH solution (0.34 mL) was re-concentrated and dried in vacuo to give the title compound as an off-white solid.

The following tabulated examples E41-E53 were prepared from the appropriate Boc-protected intermediate as indicated in the table, using methods similar to those described for Example 1, 2 or 3.

| Example No. | Prepared from Boc intermediate: | Structure | Name | Method Comment | MH+ |
|---|---|---|---|---|---|
| E41 | D47 | 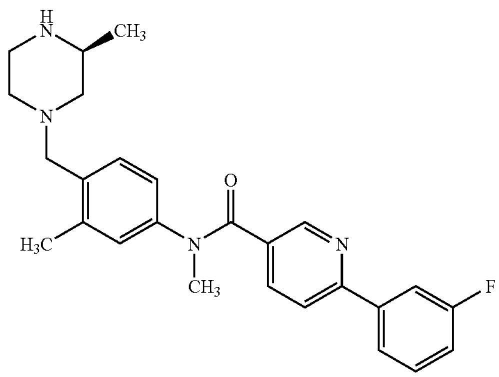 | 6-(3-fluorophenyl)-N-methyl-N-(3-methyl-4-{[(3S)-3-methyl-1-piperazinyl]methyl}phenyl)-3-pyridinecarboxamide | Similar method to E1 with reaction time of 1.5 h | 433.2 |
| E42 | D48 | 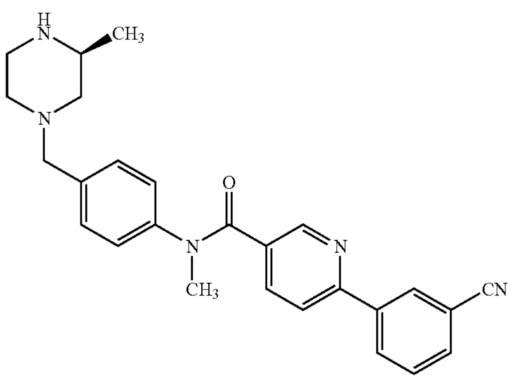 | 6-(3-cyanophenyl)-N-methyl-N-(4-{[(3S)-3-methyl-1-piperazinyl]methyl}phenyl)-3-pyridinecarboxamide | Similar method to E1 with column chromatography | 426.3 |
| E43 | D57 | 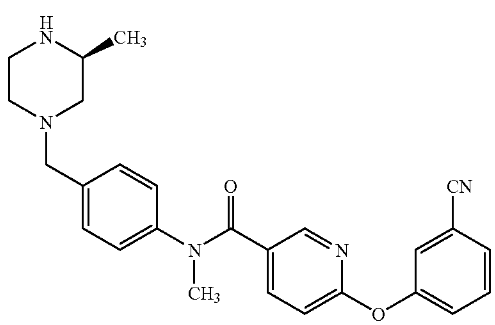 | 6-[(3-cyanophenyl)oxy]-N-methyl-N-(4-{[(3S)-3-methyl-1-piperazinyl]methyl}phenyl)-3-pyridinecarboxamide | Similar method to E2 with reaction time of 2 h and aq. work-up using DCM/sat. aq. NaHCO$_3$ solution followed by column chromatography and MDAP purification. | 442.2 |
| E44 | D50 | 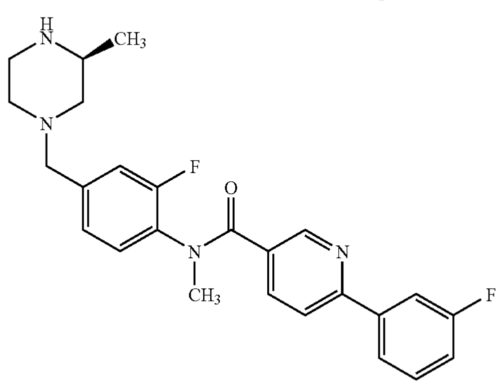 | N-(2-fluoro-4-{[(3S)-3-methyl-1-piperazinyl]methyl}phenyl)-6-(3-fluorophenyl)-N-methyl-3-pyridinecarboxamide | Similar method to E1 with reaction time of 2-3 h and aq. work-up using DCM/2 M NaOH. Salt formation in EtOAc. | 437.1 |

| Example No. | Prepared from Boc intermediate: | Structure | Name | Method Comment | MH+ |
|---|---|---|---|---|---|
| E45 | D73 | 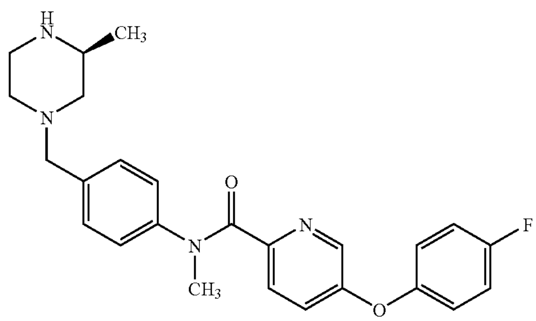 | 5-[(4-fluorophenyl)oxy]-N-methyl-N-(4-{[(3S)-3-methyl-1-piperazinyl]methyl}phenyl)-2-pyridinecarboxamide | Similar method to E2 with reaction time of 2 h and aq. work-up using DCM/sat. aq. NaHCO$_3$ solution followed by MDAP purification. | 435.2 |
| E46 | D74 | 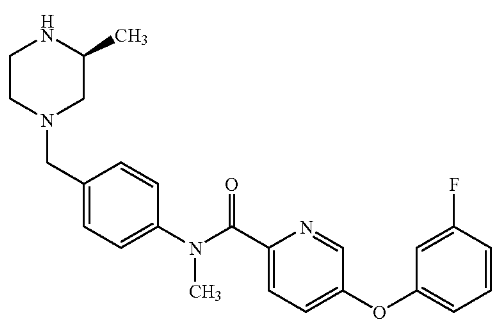 | 5-[(3-fluorophenyl)oxy]-N-methyl-N-(4-{[(3S)-3-methyl-1-piperazinyl]methyl}phenyl)-2-pyridinecarboxamide | Similar method to E2 with reaction time of 2 h and aq. work-up using DCM/sat. aq. NaHCO$_3$ solution followed by MDAP purification. | 435.2 |
| E47 | D69 | 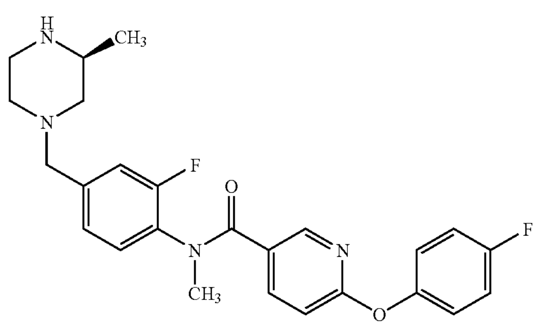 | N-(2-fluoro-4-{[(3S)-3-methyl-1-piperazinyl]methyl}phenyl)-6-[(4-fluorophenyl)oxy]-N-methyl-3-pyridinecarboxamide | Similar method to E1 with aq. work-up using DCM and 2 M NaOH. Salt formation in EtOAc. | 453.2 |
| E48 | D75 | 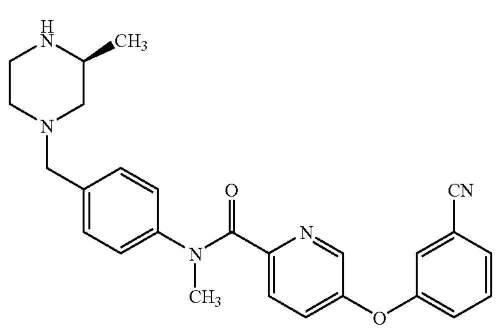 | 5-[(3-cyanophenyl)oxy]-N-methyl-N-(4-{[(3S)-3-methyl-1-piperazinyl]methyl}phenyl)-2-pyridinecarboxamide | Similar method to E2 with reaction time of 2 h and aq. work-up using DCM/sat. aq. NaHCO$_3$ solution followed by column chromatograph | 442.2 |

-continued

| Example No. | Prepared from Boc intermediate: | Structure | Name | Method Comment | MH+ |
|---|---|---|---|---|---|
| E49 | D76 | 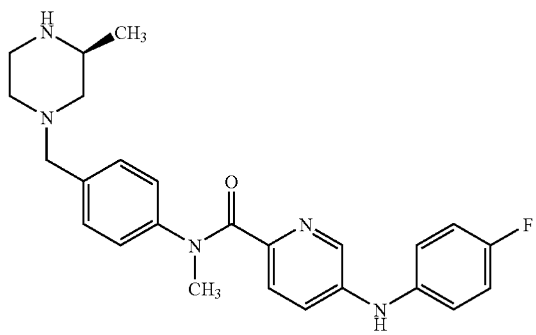 | 5-[(4-fluorophenyl)amino]-N-methyl-N-(4-{[(3S)-3-methyl-1-piperazinyl]methyl}phenyl)-2-pyridinecarboxamide | Similar method to E2 with aq. work-up using DCM and sat. aq. NaHCO₃ solution followed by column chromatography. | 434.2 |
| E50 | D51 | 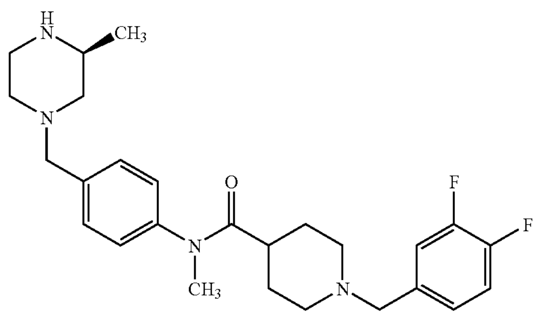 | 1-[(3,4-difluorophenyl)methyl]-N-methyl-N-(4-{[(3S)-3-methyl-1-piperazinyl]methyl}phenyl)-4-piperidinecarboxamide | Similar method to E1 with column chromatography followed by chromatography using Biotage KP-NH ™ column* | 457.2 |
| E51 | D52 | 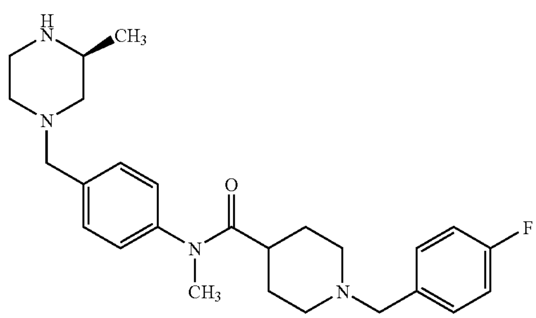 | 1-[(4-fluorophenyl)methyl]-N-methyl-N-(4-{[(3S)-3-methyl-1-piperazinyl]methyl}phenyl)-4-piperidinecarboxamide | Similar method to E1 with chromatography using Biotage KP-NH ™ column | 439.2 |
| E52 | D53 | 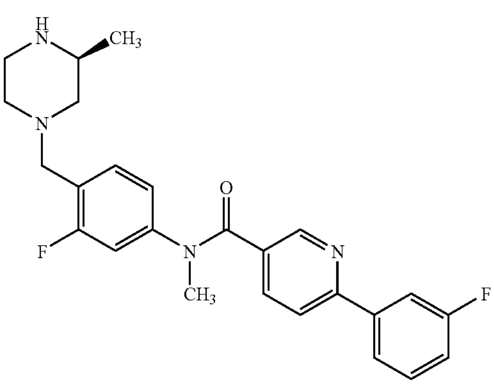 | N-(3-fluoro-4-{[(3S)-3-methyl-1-piperazinyl]methyl}phenyl)-6-(3-fluorophenyl)-N-methyl-3-pyridinecarboxamide | Similar method to E1 with reaction time of 4 h and aq. work-up using DCM/2 M NaOH. Salt formation in DCM. | 437.1 |

| Example No. | Prepared from Boc intermediate: | Structure | Name | Method Comment | MH+ |
|---|---|---|---|---|---|
| E53 | D71 | 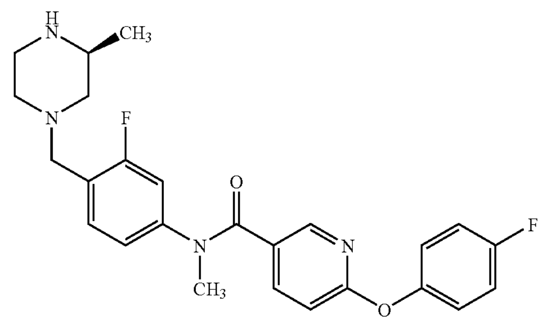 | N-(3-fluoro-4-{[(3S)-3-methyl-1-piperazinyl]methyl}phenyl)-6-[(4-fluorophenyl)oxy]-N-methyl-3-pyridinecarboxamide | Similar method to E1 with reaction time of 4 h and aq. work-up using DCM/2 M NaOH. Salt formation in DCM. | 453.1 |
| E54 | D111 | 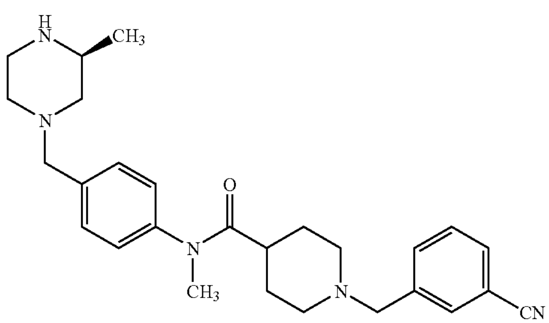 | 1-[(3-cyanophenyl)methyl]-N-methyl-N-(4-{[(3S)-3-methyl-1-piperazinyl]methyl}phenyl)-4-piperidinecarboxamide | Similar method to E1 with reaction time of 0.5 h | 446.4 |
| E55 | D112 | 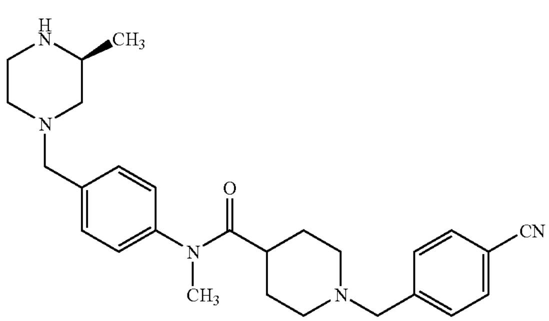 | 1-[(4-cyanophenyl)methyl]-N-methyl-N-(4-{[(3S)-3-methyl-1-piperazinyl]methyl}phenyl)-4-piperidinecarboxamide | Similar method to E1 with reaction time of 0.5 h | 446.4 |
| E56 | D113 | 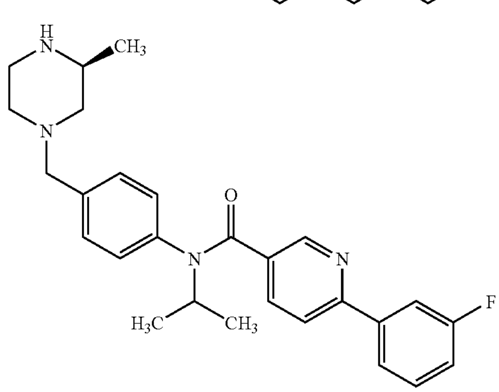 | 6-(3-fluorophenyl)-N-(1-methylethyl)-N-(4-{[(3S)-3-methyl-1-piperazinyl]methyl}phenyl)-3-pyridinecarboxamide | Similar method to E1 with reaction time of 2 h | 447.3 |

| Example No. | Prepared from Boc intermediate: | Structure | Name | Method Comment | MH+ |
|---|---|---|---|---|---|
| E57 | D114 | 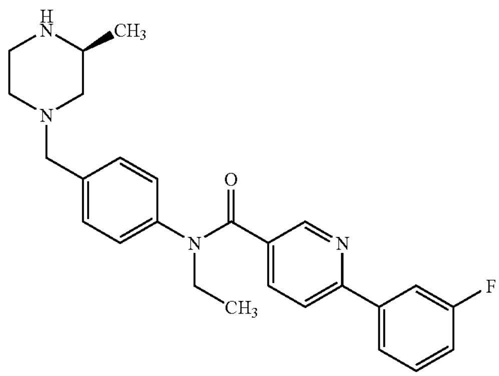 | N-ethyl-6-(3-fluorophenyl)-N-(4-{[(3S)-3-methyl-1-piperazinyl]methyl}phenyl)-3-pyridinecarboxamide | Similar method to E1 with reaction time of 3 h | 433.2 |
| E58 | D115 | 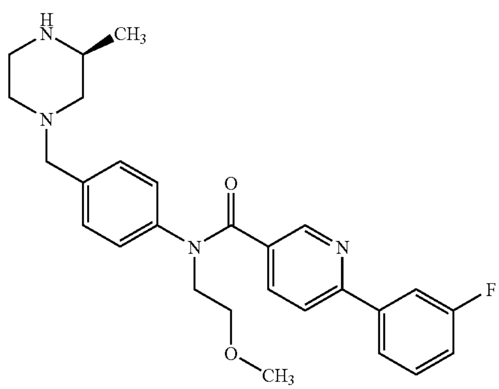 | 6-(3-fluorophenyl)-N-[2-(methyloxy)ethyl]-N-(4-{[(3S)-3-methyl-1-piperazinyl]methyl}phenyl)-3-pyridinecarboxamide | Similar method to E1 with chromatography using Biotage KP-NH ™ column | 463.3 |
| E59 | D116 | 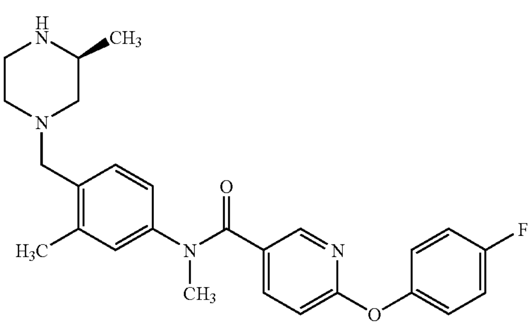 | 6-[(4-fluorophenyl)oxy]-N-methyl-N-(3-methyl-4-{[(3S)-3-methyl-1-piperazinyl]methyl}phenyl)-3-pyridinecarboxamide | Similar method to E1 with reaction time of 0.5 h and column chromatography | 449.3 |
| E60 | D117 | 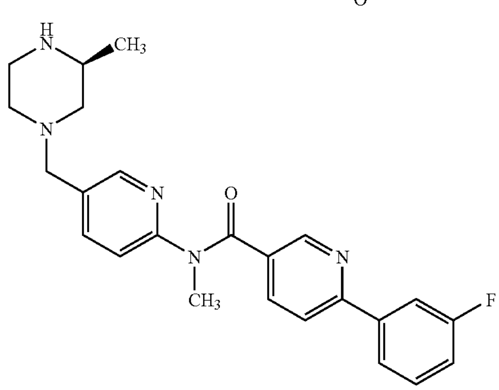 | 6-(3-fluorophenyl)-N-methyl-N-(5-{[(3S)-3-methyl-1-piperazinyl]methyl}-2-pyridinyl)-3-pyridinecarboxamide | Similar method to E1 with column chromatography | 420.2 |

-continued

| Example No. | Prepared from Boc intermediate: | Structure | Name | Method Comment | MH+ |
|---|---|---|---|---|---|
| E61 | D124 | 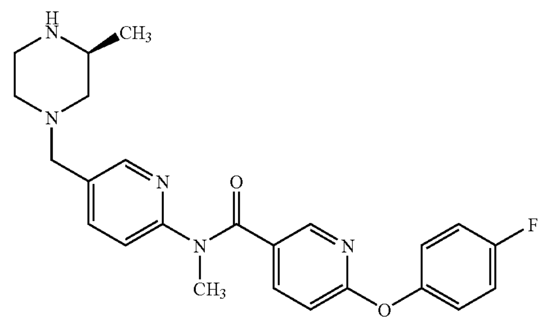 | 6-[(4-fluorophenyl)oxy]-N-methyl-N-(5-{[(3S)-3-methyl-1-piperazinyl]methyl}-2-pyridinyl)-3-pyridinecarboxamide | Similar method to E1 with reaction time of 0.5 h and column chromatography | 436.2 |
| E62 | D125 | 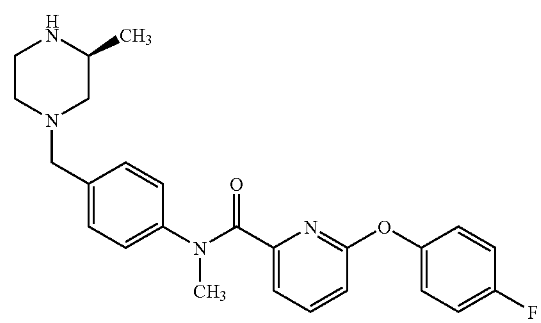 | 6-[(4-fluorophenyl)oxy]-N-methyl-N-(4-{[(3S)-3-methyl-1-piperazinyl]methyl}phenyl)-2-pyridinecarboxamide | Similar method to E1 with reaction time of 2 h and column chromatography. Salt formation in DCM/MeOH | 435.2 |
| E63 | D127 | 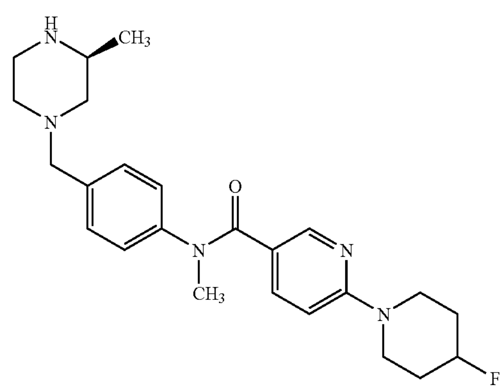 | 6-(4-fluoro-1-piperidinyl)-N-methyl-N-(4-{[(3S)-3-methyl-1-piperazinyl]methyl}phenyl)-3-pyridinecarboxamide | Similar method to E1 with reaction time of 2 h and column chromatography. Salt formation in DCM/MeOH | 426.2 |
| E64 | D129 | 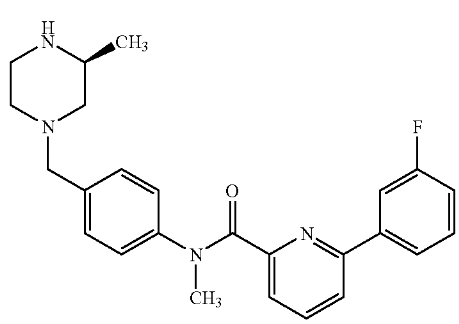 | 6-(3-fluorophenyl)-N-methyl-N-(4-{[(3S)-3-methyl-1-piperazinyl]methyl}phenyl)-2-pyridinecarboxamide | Similar method to E1 with reaction time of 2 h. Salt formation in DCM/MeOH | 419.2 |

-continued

| Example No. | Prepared from Boc intermediate: | Structure | Name | Method Comment | MH+ |
|---|---|---|---|---|---|
| E65 | D141 | 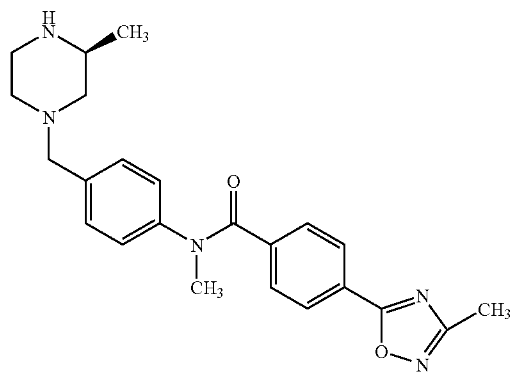 | N-methyl-4-(3-methyl-1,2,4-oxadiazol-5-yl)-N-(4-{[(3S)-3-methyl-1-piperazinyl]methyl}phenyl)benzamide | Similar method to E1 with reaction time of 3 h. Salt formation in DCM/MeOH | 406.3 |
| E66 | D121 | 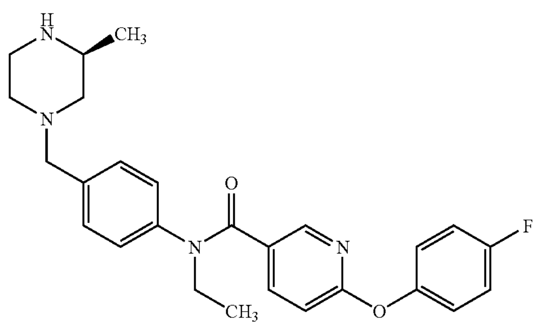 | N-ethyl-6-[(4-fluorophenyl)oxy]-N-(4-{[(3S)-3-methyl-1-piperazinyl]methyl}phenyl)-3-pyridinecarboxamide | Similar method to E1 with reaction time of 1.5 h. Salt formation in DCM. | 449.4 |
| E67 | D122 | 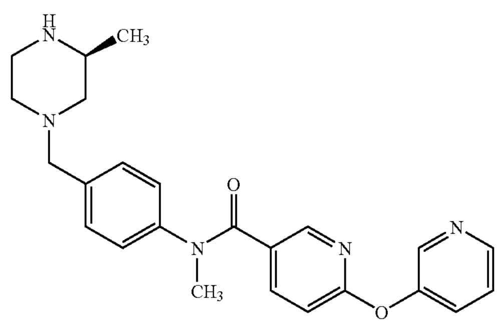 | N-methyl-N-(4-{[(3S)-3-methyl-1-piperazinyl]methyl}phenyl)-6-(3-pyridinyloxy)-3-pyridinecarboxamide | Similar method to E1 with SCX purification. Salt formation in DCM/MeOH | 418.1 |
| E68 | D126 | 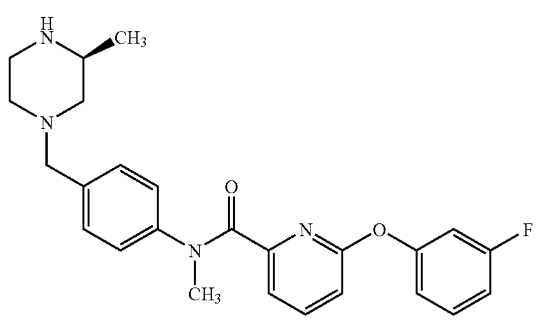 | 6-[(3-fluorophenyl)oxy]-N-methyl-N-(4-{[(3S)-3-methyl-1-pipeerazinyl]methyl}phenyl)-2-pyridinecarboxamide | Similar method to E1 with reaction time of 2 h, SCX and column chromatography. Salt formation in DCM/MeOH | 435.2 |

| Example No. | Prepared from Boc intermediate: | Structure | Name | Method Comment | MH+ |
|---|---|---|---|---|---|
| E69 | D128 | 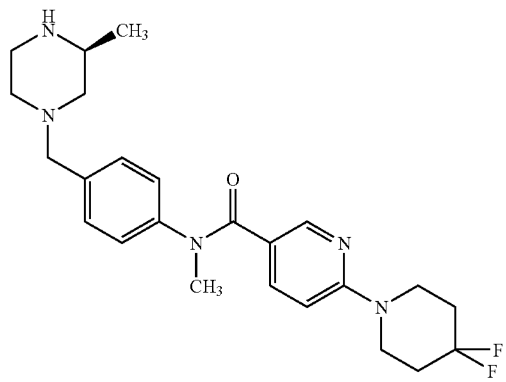 | 6-(4,4-difluoro-1-piperidinyl)-N-methyl-N-(4-{[(3S)-3-methyl-1-piperazinyl]methyl}phenyl)-3-pyridinecarboxamide | Similar method to E1 with reaction time of 2 h and MDAP purification. Salt formation in DCM/MeOH | 444.1 |
| E70 | D109 | 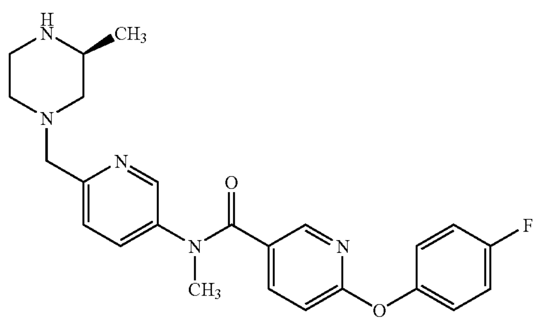 | 6-[(4-fluorophenyl)oxy]-N-methyl-N-(6-{[(3S)-3-methyl-1-piperazinyl]methyl}-3-pyridinyl)-3-pyridinecarboxamide | Similar method to E2 with reaction time of 2 h. | 436.3 |
| E71 | D131 | 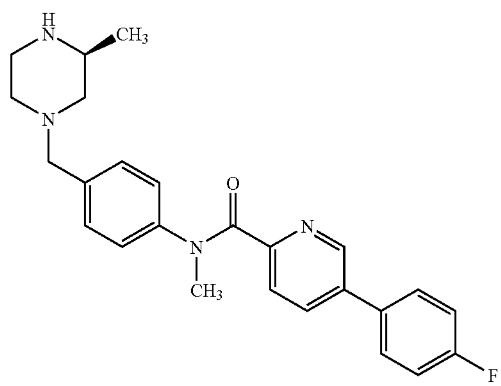 | 5-(4-fluorophenyl)-N-methyl-N-(4-{[(3S)-3-methyl-1-piperazinyl]methyl}phenyl)-2-pyridinecarboxamide | Similar method to E2 with reaction time of 2 h. | 419.3 |
| E72 | D132 | 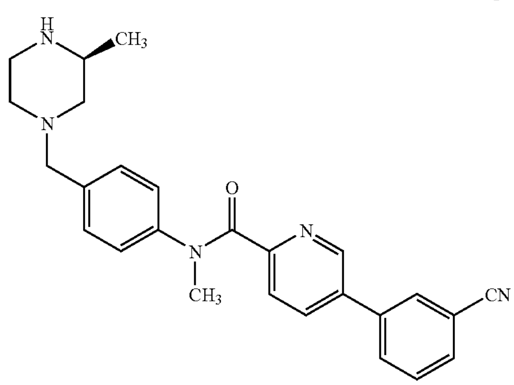 | 5-(3-cyanophenyl)-N-methyl-N-(4-{[(3S)-3-methyl-1-piperazinyl]methyl}phenyl)-2-pyridinecarboxamide | Similar method to E2. | 426.2 |

| Example No. | Prepared from Boc intermediate: | Structure | Name | Method Comment | MH+ |
|---|---|---|---|---|---|
| E73 | D133 | 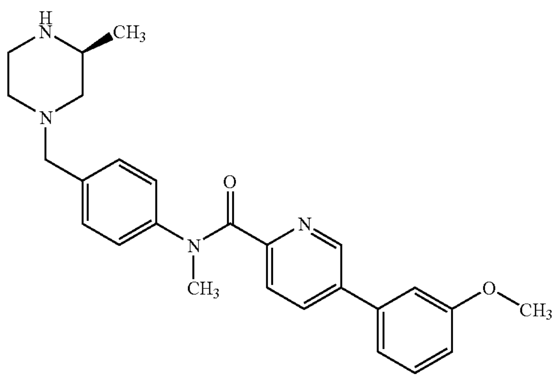 | N-methyl-5-[3-(methyloxy)phenyl]-N-(4-{[(3S)-3-methyl-1-piperazinyl]methyl}phenyl)-2-pyridinecarboxamide | Similar method to E2 with reaction time of 2 h. | 431.2 |
| E74 | D134 | 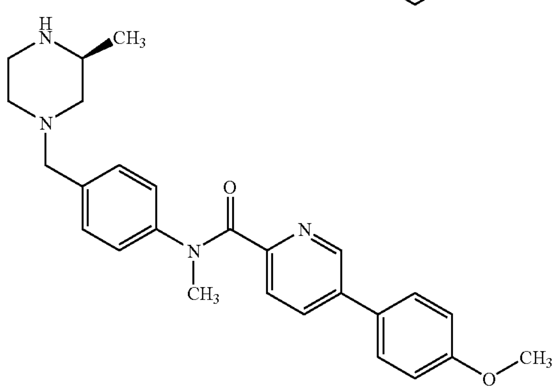 | N-methyl-5-[4-(methyloxy)phenyl]-N-(4-{[(3S)-3-methyl-1-piperazinyl]methyl}phenyl)-2-pyridinecarboxamide | Similar method to E2 with reaction time of 2 h. | 431.2 |
| E75 | D135 | 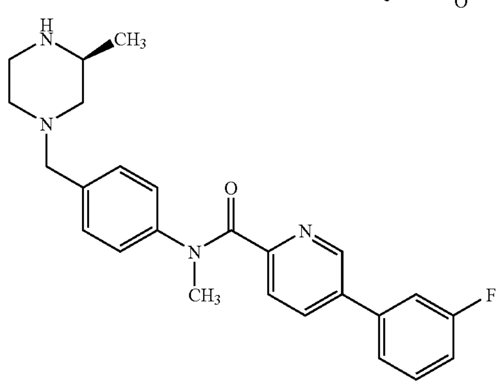 | 5-(3-fluorophenyl)-N-methyl-N-(4-{[(3S)-3-methyl-1-piperazinyl]methyl}phenyl)-2-pyridinecarboxamide | Similar method to E2 with reaction time of 2 h and no column chromatography. | 419.2 |
| E76 | D110 | 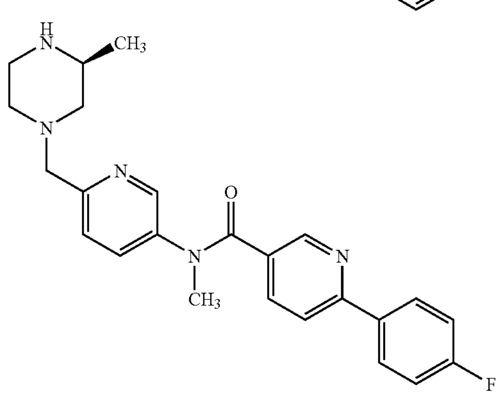 | 6-(4-fluorophenyl)-N-methyl-N-(6-{[(3S)-3-methyl-1-piperazinyl]methyl}-3-pyridinyl)-3-pyridinecarboxamide | Similar method to E2 with reaction time of 3 h and MDAP purification instead of column chromatography | 420.3 |

EXAMPLE 77

6-[(4-Fluorophenyl)oxy]-N-methyl-N-(4-methyl-5-{[(3S)-3-methyl-1-piperazinyl]methyl}-2-pyridinyl)-3-pyridinecarboxamide (E77)

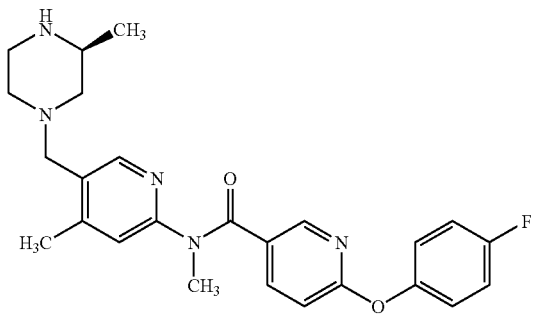

1,1-Dimethylethyl (2S)-4-({6-[({6-[(4-fluorophenyl)oxy]-3-pyridinyl}carbonyl)(methyl)amino]-4-methyl-3-pyridinyl}methyl)-2-methyl-1-piperazinecarboxylate (D118) (26 mg, 0.047 mmol) was dissolved in dry DCM (4 mL). TFA (1 mL) was added and the reaction mixture was stirred at room temperature, under argon. The reaction mixture was concentrated, re-dissolved in methanol (2 mL) and loaded on to a 1 g SCX cartridge. Elution with methanol (20 mL) followed by 2M $NH_3$ in methanol (20 mL) gave a colourless oil. The product was further purified by MDAP. The resulting oil was dissolved in methanol (1 mL) and loaded on to a 1 g SCX cartridge and eluted with methanol (20 mL), followed by 2M $NH_3$ in methanol (20 mL) to give the title compound as a colourless oil (15 mg). MS (ES): $MH^+$ 450.1.

This whole was dissolved in MeOH (1 mL) and treated with 1M HCl in $Et_2O$ (0.037 mL) to give the hydrochloride salt of the title compound as a white solid (13.6 mg). MS (ES): $MH^+$ 450.3.

EXAMPLE 78

N,2'-Dimethyl-N-(4-{[(3S)-3-methyl-1-piperazinyl]methyl}phenyl)-3,4'-bipyridine-6-carboxamide (E78)

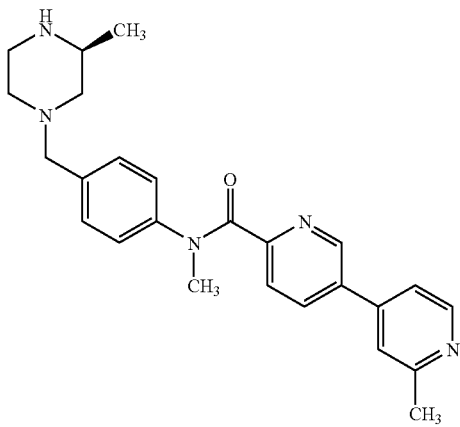

The title compound was prepared from 1,1-dimethylethyl (2S)-2-methyl-4-[(4-{methyl[(2'-methyl-3,4'-bipyridin-6-yl)carbonyl]amino}phenyl)methyl]-1-piperazinecarboxylate (D130) using a procedure similar to that described for E1 in Example 1 although hydrochloride salt preparation was carried out in DCM/MeOH (1:1). $\delta_H$ (MeOD, 400 MHz) 8.96 (1H, br.m), 8.76 (1H, d), 8.39 (1H, br.m), 8.33 (1H, s), 8.23 (1H, d), 7.81 (1H, br.d), 7.58 (2H, br.s), 7.36 (2H, br.s), 3.86 (1H, br.s), 3.58-3.71 (4H, m), 3.54 (3H, s), 3.44 (1H, m), 3.34 (2H, s), 3.30 (1H, m), 2.85 (3H, s), 1.40 (3H, d), NH not observed. MS ($ES^+$): 316.1, no molecular ion ($MH^+$) observed.

EXAMPLE 79

6-[(4-Fluorophenyl)oxy]-N-[2-(methyloxy)ethyl]-N-(4-{[(3S)-3-methyl-1-piperazinyl]methyl}phenyl)-3-pyridinecarboxamide (E79)

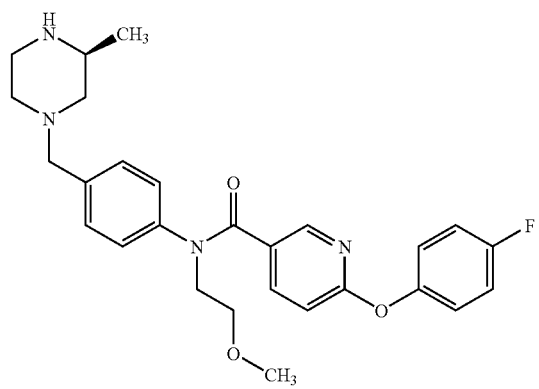

1,1-Dimethylethyl (2S)-4-[(4-{({6-[(4-fluorophenyl)oxy]-3-pyridinyl}carbonyl)[2-(methyloxy)ethyl]amino}phenyl)methyl]-2-methyl-1-piperazine carboxylate (D119) (0.077 g, 0.13 mmol) was dissolved in 4M HCl in dioxane (5 mL). A few drops of water were added and the reaction was stirred for 2 h. The solvent was removed in vacuo and the resulting yellow oil was dissolved in MeOH and loaded onto an SCX cartridge which was eluted with DCM, MeOH and 2M $NH_3$ in MeOH. The ammoniacal fractions were combined and concentrated to give the title compound as a yellow oil (0.0667 g). MS (ES): $MH^+$ 479.4.

This whole was dissolved in DCM/MeOH (1:1, 2 mL) and treated with 1M HCl in $Et_2O$ (0.15 mL). After standing for 10 minutes, the solvents were removed to give the hydrochloride salt of the title compound (0.053 g) as a pale yellow solid. MS (ES): $MH^+$ 479.4.

The following tabulated examples E80-E85 were prepared from the appropriate Boc-protected intermediate as indicated in the table, using methods similar to those described for Example 79.

| Example No. | Prepared from Boc intermediate | Structure | Name | Method Comment | MH+ |
|---|---|---|---|---|---|
| E80 | D120 | 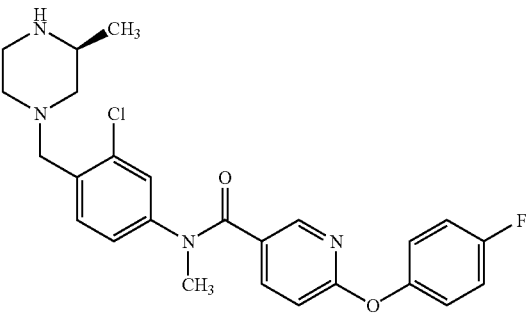 | N-(3-chloro-4-{[(3S)-3-methyl-1-piperazinyl]methyl}phenyl)-6-[(4-fluorophenyl)oxy]-N-methyl-3-pyridinecarboxamide | Similar method to E79 with column chromatography | 469/471 |
| E81 | D136 | 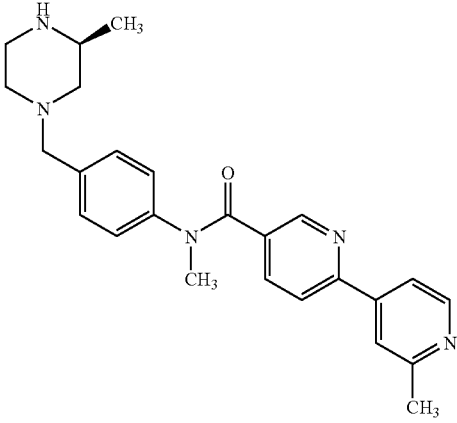 | N,2'-Dimethyl-N-(4-{[(3S)-3-methyl-1-piperazinyl]methyl}phenyl)-2,4'-bipyridine-5-carboxamide | Similar method to E79 | 416.3 |
| E82 | D137 | 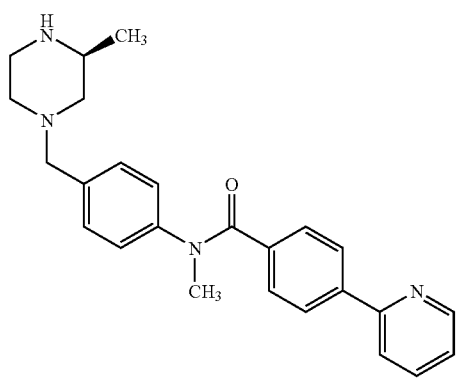 | N-methyl-N-(4-{[(3S)-3-methyl-1-piperazinyl]methyl}phenyl)-4-(2-pyridinyl)benzamide | Similar method to E79 with reaction time of overnight and MDAP purification. Salt formation in MeOH | 401.3 |

-continued

| Example No. | Prepared from Boc intermediate | Structure | Name | Method Comment | MH+ |
|---|---|---|---|---|---|
| E83 | D138 | 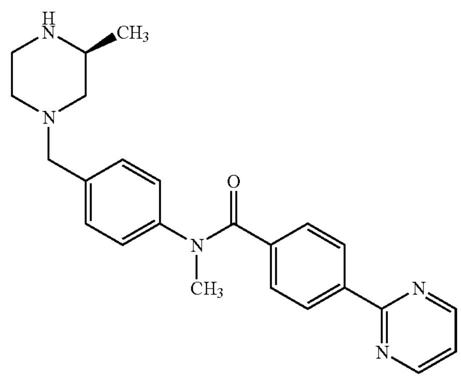 | N-methyl-N-(4-{[(3S)-3-methyl-1-piperazinyl]methyl}phenyl)-4-(2-pyrimidinyl)benzamide | Similar method to E79 with reaction time of overnight and MDAP purification. Salt formation in MeOH | 402.1 |
| E84 | D139 | 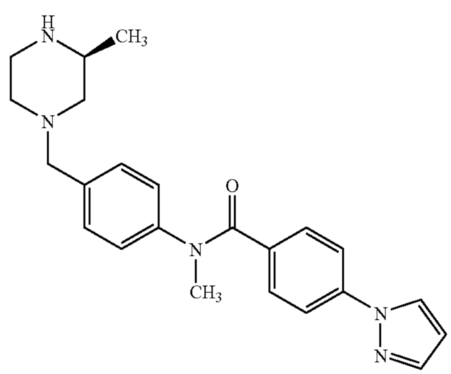 | N-methyl-N-(4-{[(3S)-3-methyl-1-piperazinyl]methyl}phenyl)-4-(1H-pyrazol-1-yl)benzamide | Similar method to E79 with reaction time of overnight. Salt formation in MeOH | 390.3 |
| E85 | D140 | 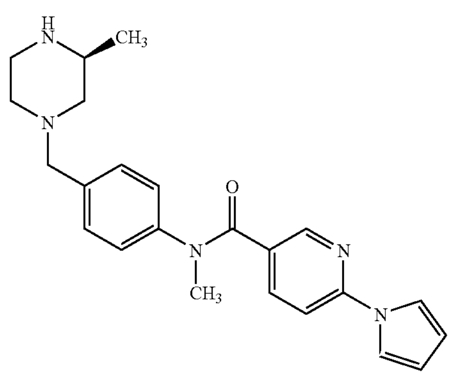 | N-methyl-N-(4-{[(3S)-3-methyl-1-piperazinyl]methyl}phenyl)-6-(1H-pyrrol-1-yl)-3-pyridinecarboxamide | Similar method to E79 with reaction time of overnight. Salt formation in MeOH | 390.3 |

EXAMPLE 86

N-Methyl-N-(4-{[(3S)-3-methyl-1-piperazinyl]methyl}phenyl)-4-{[4-(trifluoromethyl)phenyl]carbonyl}benzamide (E86)

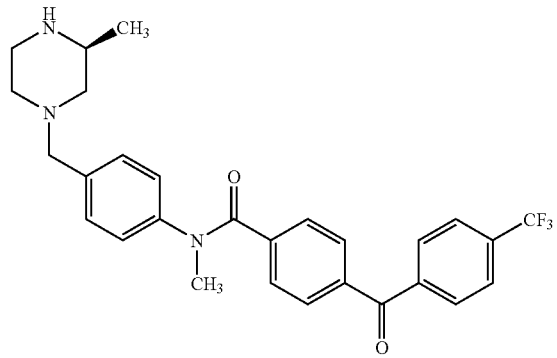

1,1-Dimethylethyl (2S)-2-methyl-4-[(4-{methyl[(4-{[4-(trifluoromethyl)phenyl]carbonyl}phenyl)carbonyl]amino}phenyl)methyl]-1-piperazinecarboxylate (D123) (0.244 g, 0.41 mmol) was dissolved in 4M HCl in dioxane (5 mL) and the reaction was stirred for 2 h. The solvent was removed in vacuo to give the dihydrochloride salt of the title compound as an off-white solid (0.203 g) which was further dried in vacuo. MS (ES): MH$^+$ 496.1.

The following tabulated examples E87-E93 were prepared using methods similar to those described for Examples E1, E2, E3 or E79.

| Example No. | Structure | Name | MH+ |
|---|---|---|---|
| E87 | 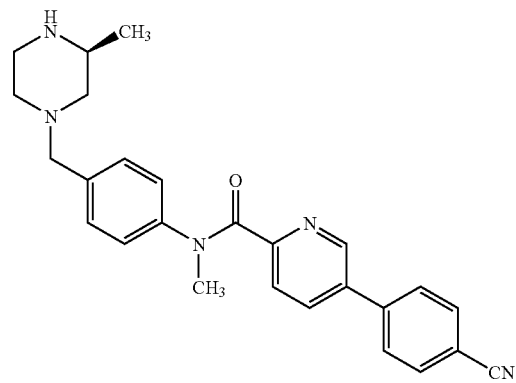 | 5-(4-cyanophenyl)-N-methyl-N-(4-{[(3S)-3-methyl-1-piperazinyl]methyl}phenyl)-2-pyridinecarboxamide | 426.1 |
| E88 | 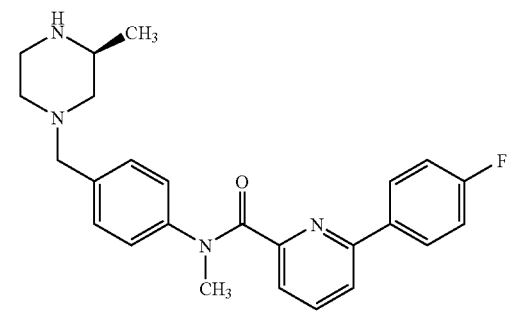 | 6-(4-fluorophenyl)-N-methyl-N-(4-{[(3S)-3-methyl-1-piperazinyl]methyl}phenyl)-2-pyridinecarboxamide | 419.1 |

-continued

| Example No. | Structure | Name | MH+ |
|---|---|---|---|
| E89 | 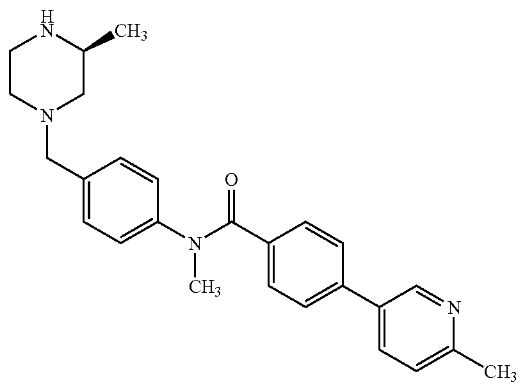 | N-methyl-N-(4-{[(3S)-3-methyl-1-piperazinyl]methyl}phenyl)-4-(6-methyl-3-pyridinyl)benzamide | 415.2 |
| E90 | 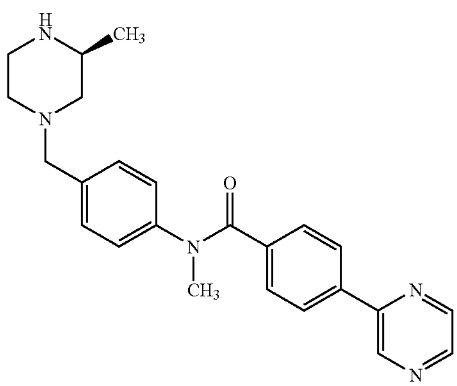 | N-methyl-N-(4-{[(3S)-3-methyl-1-piperazinyl]methyl}phenyl)-4-(2-pyrazinyl)benzamide | 402.1 |
| E91 | 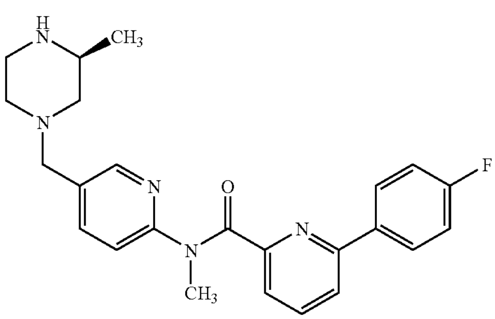 | 6-(4-fluorophenyl)-N-methyl-N-(5-{[(3S)-3-methyl-1-piperazinyl]methyl}-2-2-pyridinyl)-2-pyridinecarboxamide | 420.3 |
| E92 | 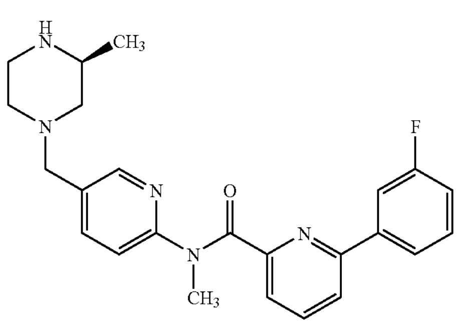 | 6-(3-fluorophenyl)-N-methyl-N-(5-{[(3S)-3-methyl-1-piperazinyl]methyl}-2-pyridinyl)-2-pyridinecarboxamide | 420.3 |

| Example No. | Structure | Name | MH+ |
|---|---|---|---|
| E93 | 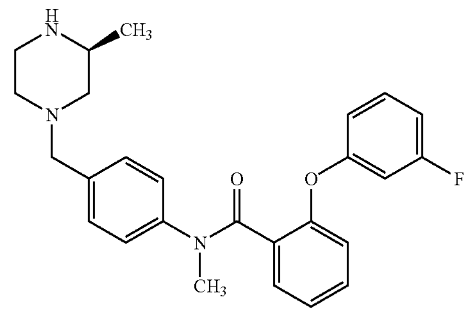 | 2-[(3-fluorophenyl)oxy]-N-methyl-N-(4-{[(3S)-3-methyl-1-piperazinyl]methyl}phenyl)benzamide | 434.2 |

GPR38 FLIPR Functional Agonist Assay Protocol 24 hours prior to assay, CHO-K1 cells stably expressing the GPR38 receptor were seeded (10,000 cells/well) into poly-D-lysine coated 384-well black-wall, clear-bottom microtitre plates (Greiner). On the day of assay, media was aspirated from cell plates using a cell washer (leaving 10 ul of media). Cells were immediately loaded with loading buffer [Tyrodes (Elga water+145 mM NaCl+5 mM KCl+20 mM HEPES+10 mM glucose+1 mM MgCl$_2$)+1.5 mM CaCl$_2$+ 0.714 mg/mL Probenicid (predissolved in 1 M NaOH)+0.25 mM brilliant black+2 uM Fluo 4 dye], and incubated at 37.5° C. for 1 hour.

Plates were then assayed on a FLuorometric Imaging Plate Reader (FLIPR, Molecular Devices).

Master compound plates were prepared in 100% DMSO. A top concentration of 3 mM was used (giving 12 µM final concentration in assay) and this was serially diluted 1 in 4. 1 ul from the master plate was transferred to a daughter plate, to which 50 µl of compound dilution buffer (Tyrodes+1 mg/mL BSA+1.5 mM CaCl$_2$) was added. In the FLIPR, 10 ul of test compound was added to the cells and changes in fluorescence measured over a 1 minute timeframe. Maximum change in fluorescence over baseline was used to determine agonist response and concentration response curves were constructed, using a 4-parameter logistic equation.

In alternative protocols the loading buffer was HBSS {Elga water+137 mM NaCl+5 mM KCl+0.41 mMa KH2PO4(anhyd)+20 mM HEPES+5 mM glucose+0.81 mM MgSO$_4$(anhyd)+1.3 mM CaCl2+4.16 mM NaHCO3}+0.25 mM brilliant black+2 uM Fluo 4 dye and the CHO-K1 cells thawed from frozen aliquots and seeded 24 hours prior to the assay.

Examples 1 to 86 of the invention have a pEC50≧6.0 in one or more of the FLIPR assays described above.

What is claimed is:

1. A compound which is: 6-[(4-fluorophenyl)oxy]-N-methyl-N-(4-{[(3S)-3-methyl-1-piperazinyl]methyl}phenyl)-3-pyridinecarboxamide or a salt thereof.

2. A compound which is: 6-[(4-fluorophenyl)oxy]-N-methyl-N-(4{[(3S)-3-methyl-1-piperazinyl]methyl}phenyl)-3-pyridinecarboxamide or a pharmaceutically acceptable salt thereof.

3. A pharmaceutical composition comprising the compound according to claim 2 and a pharmaceutically acceptable carrier.

4. A pharmaceutical composition according to claim 3 wherein the composition is for oral administration.

5. A pharmaceutical composition of claim 3 wherein the composition is for parenteral administration.

6. A compound which is 6-[(4-fluorophenyl)oxy]-N-methyl-N-(4-{[(3S)-3-methyl-1-piperazinyl]methyl}phenyl)-3-pyridinecarboxamide fumarate.

7. A pharmaceutical composition comprising the compound according to claim 6 and a pharmaceutically acceptable carrier.

8. A pharmaceutical composition according to claim 7 wherein the composition is for oral administration.

9. A pharmaceutical composition according to claim 7 wherein the composition is for parenteral administration.

10. A compound which is 6-[(4-fluorophenyl)oxy]-N-methyl-N-(4-{[(3S)-3-methyl-1-piperazinyl]methyl}phenyl)-3-pyridinecarboxamide fumarate having characteristic XRPD peaks at 4.5, 8.9, 9.8, 12.2, 13.0, 14.6, 16.0, 16.7, 17.7, 18.9, 20.2, 21.1, 22.1, 23.5, 24.1, 25.2, 26.3 and 27.0 degrees 2 theta.

11. A pharmaceutical composition comprising the compound according to claim 10 and a pharmaceutically acceptable carrier.

12. A pharmaceutical composition according to claim 11 wherein the composition is for oral administration.

13. A pharmaceutical composition according to claim 11 wherein the composition is for parenteral administration.

14. A compound which is 6-[(4-fluorophenyl)oxy]-N-methyl-N-(4-{[(3S)-3-methyl-1-piperazinyl]methyl}phenyl)-3-pyridinecarboxamide fumarate having a DSC with a melt onset of 141° C.

15. A pharmaceutical composition comprising the compound according to claim 14 and a pharmaceutically acceptable carrier.

16. A pharmaceutical composition according to claim 15 wherein the composition is for oral administration.

17. A pharmaceutical composition according to claim 15 wherein the composition is for parenteral administration.

18. A compound which is 6-[(4-fluorophenyl)oxy]-N-methyl-N-(4-{[(3S)-3-methyl-1-piperazinyl]methyl}phenyl)-3-pyridinecarboxamide fumarate having characteristic XRPD peaks at 9.0, 9.7, 12.2, 13.7, 15.4, 15.8, 16.1, 16.7, 17.1, 18.0, 18.3, 19.1, 19.4, 19.7, 20.3, 20.9, 22.5, 22.9, 25.2 and 25.6 degrees 2 theta.

19. A pharmaceutical composition comprising the compound according to claim 18 and a pharmaceutically acceptable carrier.

20. A pharmaceutical composition according to claim 19 wherein the composition is for oral administration.

21. A pharmaceutical composition according to claim 19 wherein the composition is for parenteral administration.

22. A compound which is 6-[(4-fluorophenyl)oxy]-N-methyl-N-(4-{[(3S)-3-methyl-1-piperazinyl]methyl}phenyl)-3-pyridinecarboxamide fumarate having a DSC with a melt onset of 153° C.

23. A pharmaceutical composition comprising the compound according to claim 22 and a pharmaceutically acceptable carrier.

24. A pharmaceutical composition according to claim 23 wherein the composition is for oral administration.

25. A pharmaceutical composition according to claim 23 wherein the composition is for parenteral administration.

26. A compound according to claim 1 which is 6-[(4-fluorophenyl)oxy]-N-methyl-N-(4-{[(3S)-3-methyl-1piperazinyl]methyl}phenyl)-3-pyridinecarboxamide hydrochloride.

27. A pharmaceutical composition comprising the compound according to claim 26 and a pharmaceutically acceptable carrier.

28. A method of treatment of gastric stasis in an enterally fed patient, wherein said patient is a human, comprising administering to said human a therapeutically effective amount of the compound according to claim 1.

29. A method of treatment of gastric stasis in an enterally fed patient, wherein said patient is a human, comprising administering to said human a therapeutically effective amount of the compound according to claim 2.

30. A method of treatment of gastric stasis in an enterally fed patient, wherein said patient is a human, comprising administering to said human a therapeutically effective amount of the compound according to claim 6.

31. A method of treatment of gastric stasis in an enterally fed patient, wherein said patient is a human, comprising administering to said human a therapeutically effective amount of the compound according to claim 10.

32. A method of treatment of gastric stasis in an enterally fed patient, wherein said patient is a human, comprising administering to said human a therapeutically effective amount of the compound according to claim 14.

33. A method of treatment of gastric stasis in an enterally fed patient, wherein said patient is a human, comprising administering to said human a therapeutically effective amount of the compound according to claim 18.

34. A method of treatment of gastric stasis in an enterally fed patient, wherein said patient is a human, comprising administering to said human a therapeutically effective amount of the compound according to claim 22.

35. A method of treatment of gastric stasis in an enterally fed patient, wherein said patient is a human, comprising administering to said human a therapeutically effective amount of the compound according to claim 26.

* * * * *